(12) United States Patent
Bates et al.

(10) Patent No.: US 10,696,661 B2
(45) Date of Patent: *Jun. 30, 2020

(54) COMPOUNDS

(71) Applicant: Exonate Limited, Cambridge, Cambridgeshire (GB)

(72) Inventors: David Bates, Nottingham (GB); Jonathan Morris, Sydney (AU); Hamish Toop, Sydney (AU); Jennifer Batson, Nottingham (GB); Andrew David Morley, Macclesfield (GB)

(73) Assignee: Exonate Limited, Cambridge, Cambridgesh (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/768,648

(22) PCT Filed: Oct. 14, 2016

(86) PCT No.: PCT/GB2016/053199
§ 371 (c)(1),
(2) Date: Apr. 16, 2018

(87) PCT Pub. No.: WO2017/064512
PCT Pub. Date: Apr. 20, 2017

(65) Prior Publication Data
US 2019/0062317 A1    Feb. 28, 2019

(30) Foreign Application Priority Data

Oct. 16, 2015  (GB) .................................. 1518365.0

(51) Int. Cl.
| C07D 405/14 | (2006.01) |
| A61K 31/496 | (2006.01) |
| C07D 413/14 | (2006.01) |
| C07D 401/12 | (2006.01) |
| C07D 405/12 | (2006.01) |
| C07D 413/12 | (2006.01) |
| C07D 417/12 | (2006.01) |
| C07D 417/14 | (2006.01) |
| C07D 307/68 | (2006.01) |
| C07D 307/52 | (2006.01) |
| C07D 261/18 | (2006.01) |
| C07D 263/48 | (2006.01) |
| A61K 31/497 | (2006.01) |
| A61K 31/506 | (2006.01) |
| A61K 9/00 | (2006.01) |
| C07D 407/12 | (2006.01) |

(52) U.S. Cl.
CPC .......... *C07D 405/14* (2013.01); *A61K 9/0048* (2013.01); *A61K 31/496* (2013.01); *A61K 31/497* (2013.01); *A61K 31/506* (2013.01); *C07D 261/18* (2013.01); *C07D 263/48* (2013.01); *C07D 307/52* (2013.01); *C07D 307/68* (2013.01); *C07D 401/12* (2013.01); *C07D 405/12* (2013.01); *C07D 407/12* (2013.01); *C07D 413/12* (2013.01); *C07D 413/14* (2013.01); *C07D 417/12* (2013.01); *C07D 417/14* (2013.01)

(58) Field of Classification Search
CPC ............................ C07D 405/14; A61K 31/496
See application file for complete search history.

(56) References Cited

U.S. PATENT DOCUMENTS

| 2009/0286766 A1* | 11/2009 | Sugasawa ............ | C07D 263/34 514/210.18 |
| 2012/0328691 A1* | 12/2012 | Shipps, Jr. ........... | C07D 277/56 424/450 |

FOREIGN PATENT DOCUMENTS

| EP | 2009005 | 12/2008 |
| WO | 2008054702 | 5/2008 |
| WO | 2014060763 | 4/2014 |
| WO | 2015159103 | 10/2015 |

OTHER PUBLICATIONS

Sugasawa et al, CA Plus DN 147:502346, p. 1-6, highlighted compound on p. 6. (Year: 2007).*
International Search Report and Written Opinion in corresponding PCT Application Serial No. PCT/GB2016/053199, dated Jan. 24, 2017.
Bressler, et al., Age-Related Eye Dis Study, G. (2004) 'Ocular risk factors for developing neovascular AMD in the fellow eyes of patients with unilateral neovascular AMD', Investigative Ophthalmology & Visual Science, 45, U924-U924 (abstract attached).
Ferris, III et al., (1984) 'Age-related macular degeneration and blindness due to neovascular maculopathy', Archives of Ophthalmology, 102(11), 1640-1642.
Patz, et al., (1977) 'Diseases of macula—diagnosis and management of choroidal neovascularization', Transactions American Academy of Ophthalmology and Otolaryngology, 83(3), 468-475 (abstract attached).
Fine, et al., (2000) 'Drug therapy: Age-related macular degeneration', New England Journal of Medicine, 342(7), 483-492.

(Continued)

Primary Examiner — Karen Cheng
(74) Attorney, Agent, or Firm — Hovey Williams LLP

(57) ABSTRACT

Anti-angiogenic treatments, for example treatment of ocular neovascularization or cancer, treatments of hyperpermeability disorders, treatments of neuropathic and neurodegenerative disorders, pain treatments, methods of treating or preventing fibrosis and compounds for use in such methods are described.

21 Claims, 9 Drawing Sheets
Specification includes a Sequence Listing.

(56) References Cited

OTHER PUBLICATIONS

Campochiaro, et al., (2006) 'Adenoviral vector-delivered pigment epithelium-derived factor for neovascular age-related macular degeneration: Results of a phase I clinical trial', Human Gene Therapy, 17(2), 167-176.
Dvorak, et al., (1995) 'Vascular-permeability factor vascular endothelial growth-factor, microvascular hyperpermeability, and angiogenesis', American Journal of Pathology, 146(5), 1029-1039.
Spilsbury, et al., (2000) 'Overexpression of vascular endothelial growth factor (VEGF) in the retinal pigment epithelium leads to the development of choroidal neovascularization', American Journal of Pathology, 157(1), 135-144.
Anderson, et al., (2002) 'Perspective—A role for local inflammation in the formation of drusen in the aging eye', American Journal of Ophthalmology, 134(3), 411-431.
Das, et al., (2003) 'Angiopoietin/Tek interactions regulate MMP-9 expression and retinal neovascularization', Laboratory Investigation, 83(11), 1637-1645.
Leung, et al., (1989) 'Vascular endothelial growth-factor is a secreted angiogenic mitogen', Science, 246(4935), 1306-1309.
Jingjing, et al., (1999) 'Human Muller cells express VEGF183, a novel spliced variant of vascular endothelial growth factor', Iovs, 40(3), 752-759.
Houck, et al., (1991) 'The vascular endothelial growth-factor family—identification of a 4th molecular-species and characterization of alternative splicing of ma', Molecular Endocrinology, 5(12), 1806-1814.
Mineur, et al., (2007) 'Newly identified biologically active and proteolysis-resistant VEGF-A isoform VEGF111 is induced by genotoxic agents', Journal of Cell Biology, 179(6), 1261-1273.
Tischer, et al., (1989) 'Vascular endothelial growth-factor—a new member of the platelet-derived growth-factor gene family', Biochemical and Biophysical Research Communications, 165(3), 1198-1206.
Neufeld, et al., (1999) 'Vascular endothelial growth factor (VEGF) and its receptors', Faseb Journal, 13(1), 9-22.
Bates, et al., (2002) 'VEGF(165)b, an inhibitory splice variant of vascular endothelial growth factor, is down-regulated in renal cell carcinoma', Cancer Research, 62(14), 4123-4131.
Woolard, et al., (2004) 'VEGF(165)b, an inhibitory vascular endothelial growth factor splice variant: Mechanism of action, in vivo effect on angiogenesis and endogenous protein expression', Cancer Research, 64(21), 7822-7835.
Perrin, et al., (2005) 'Diabetic retinopathy is associated with a switch in splicing from anti-to pro-angiogenic isoforms of vascular endothelial growth factor', Diabetologia, 48(11), 2422-2427.
Varey, et al., (2008) 'VEGF(165)b, an antiangiogenic VEGF-A isoform, binds and inhibits bevacizumab treatment in experimental colorectal carcinoma: balance of pro- and antiangiogenic VEGF-A isoforms has implications for therapy', British Journal of Cancer, 98(8), 1366-1379.
Pritchard-Jones, et al., (2007) 'Expression of VEGF(xxx)b, the inhibitory isoforms of VEGF, in malignant melanoma', British Journal of Cancer, 97(2), 223-230.
Hua, et al., (2010) 'Recombinant Human VEGF(165)b Inhibits Experimental Choroidal Neovascularization', Investigative Ophthalmology & Visual Science, 51(8), 4282-4288.
Magnussen, et al., (2010) 'VEGF-A(165)b Is Cytoprotective and Antiangiogenic in the Retina', Investigative Ophthalmology & Visual Science, 51(8), 4273-4281.
Rosenfeld, et al., (2006) 'Ranibizumab: Phase III clinical trial results', Ophthalmology clinics of North America, 19(3), 361-72.
Brown, et al., (2006) 'Ranibizumab versus verteporfin for neovascular age-related macular degeneration', New England Journal of Medicine, 355(14), 1432-1444.
Brown, et al., (2009) 'Ranibizumab versus Verteporfin Photodynamic Therapy for Neovascular Age-Related Macular Degeneration: Two-Year Results of the ANCHOR Study', Ophthalmology, 116(1), 57-65.

Schmidt-Erfurth, et al., (2011) 'Efficacy and Safety of Monthly versus Quarterly Ranibizumab Treatment in Neovascular Age-related Macular Degeneration: The EXCITE Study', Ophthalmology, 118(5).
Good, et al., (2010) 'The role of endothelin in the pathophysiology of glaucoma', Expert Opinion on Therapeutic Targets, 14(6), 647-654.
Jager, et al., (2004) 'Risks of intravitreous injection: A comprehensive review', Retina—the Journal of Retinal and Vitreous Diseases, 24(5), 676-698.
Amin, et al., (2011) 'WT1 Mutants Reveal SRPK1 to Be a Downstream Angiogenesis Target by Altering VEGF Splicing', Cancer Cell, 20(6), 768-780.
Sanford, et al., (2005a) 'Reversible phosphorylation differentially affects nuclear and cytoplasmic functons of splicing factor 2/alternative splicing factor', Proceedings of the National Academy of Sciences of the United States of America, 102(42), 15042-15047.
Nowak, et al., (2008) 'Expression of pro- and anti-angiogenic isoforms of VEGF is differentially regulated by splicing and growth factors', Journal of Cell Science, 121(20), 3487-3495.
Doukas, et al., (2008) 'Topical administration of a multi-targeted kinase inhibitor suppresses choroidal neovascularization and retinal edema', Journal of Cellular Physiology, 216(1), 29-37.
Fukuhara, et al., (2006) 'Utilization of host SR protein kinases and RNA-splicing machinery during viral replication', Proceedings of the National Academy of Sciences of the United States of America, 103(30), 11329-11333.
Rennel, et al., (2011) 'A Human Neutralizing Antibody Specific to Ang-2 Inhibits Ocular Angiogenesis', Microcirculation, 18(7).
Aubol, et al., (2003) 'Processive phosphorylation of alternative splicing factor/splicing factor Z', Proceedings of the National Academy of Sciences of the United States of America, 100(22), 12601-12606.
Velazquez-Dones, et al., (2005) 'Mass spectrometric and kinetic analysis of ASF/SF2 phosphorylation by SRPK1 and Clk/Sty', Journal of Biological Chemistry, 280(50), 41761-41768.
Ngo, et al., (2005) 'Interplay between SRPK and Clk/Sty kinases in phosphorylation of the splicing factor ASF/SF2 is regulated by a docking motif in ASF/SF2', Molecular Cell, 20(1), 77-89.
Xu, et al., (2011) 'The evolution of alternative splicing exons in vascular endothelial growth factor A', Gene, 487(2).
Caires, et al., (2012) 'VEGFA Family Isoforms Regulate Spermatogonial Stem Cell Homeostasis in Vivo', Endocrinology, 153(2).
Zhao et al., (2011) 'Expression of pro- and anti-angiogenic isoforms of VEGF in the mouse model of oxygen-induced retinopathy', Experimental Eye Research, 93(6), 921-926.
McFee, et al., (2012) 'The balance of proangiogenic and antiangiogenic VEGFA isoforms regulate follicle development', Cell and Tissue Research, 349(3).
Ishida, et al., (2003) 'VEGF(164)-mediated inflammation is required for pathological, but not physiological, ischemia-induced retinal neovascularization', Journal of Experimental Medicine, 198(3), 483-489.
Geroski, et al., (2000) 'Drug delivery for posterior segment eye disease', Investigative Ophthalmology & Visual Science, 41(5), 961-964.
Keyt, et al., (1996) 'Identification of vascular endothelial growth factor determinants for binding KDR and FLT-1 receptors—Generation of receptor-selective VEGF variants by site-directed mutagenesis', Journal of Biological Chemistry, 271(10), 5638-5646.
Stalmans, et al., (2002) 'Arteriolar and venular patterning in retinas of mice selectively expressing VEGF isoforms', Journal of Clinical Investigation, 109(3).
Gammons, et al., (2013) SRPK1 Inhibition Modulates VEGF Splicing to Reduce Pathological Neovascularization in a Rat Model of Retinopathy of Prematurity Invest. Ophthalmol. Vis. Sci. vol. 54(8) 5797-5806.
Gammons, et al., (2013) Topical Antiangiogenic SRPK1 Inhibitors Reduce Choroidal Neovascularization in Rodent Models of Exudative AMD Invest. Ophthalmol. Vis. Sci. 54(9) 6052-6062.

(56) References Cited

OTHER PUBLICATIONS

Carter, et al., (2015) The carboxyl terminus of VRGF-A is a potential target for anti-angiogenic therapy. Angiogenesis 18(1), 23-30.

Database Registry [online] Chemical Abstracts Service, Columbus, Ohio, US; Aug. 24, 2006 (Aug. 24, 2006), Interbioscreen Ltd, XP002765201, retrieved from STN Database accession No. 904009-64-9.

Database Registry [online] Chemical Abstracts Service, Columbus, Ohio, US; Aug. 22, 2006 (Aug. 22, 2006), Interbioscreen Ltd, XP002765202, retrieved from STN Database accession No. 903189-06-0.

Database Registry [online] Chemical Abstracts Service, Columbus, Ohio, US; Aug. 23, 2006 (Aug. 23, 2006), Interbioscreen Ltd, XP002766035, retrieved from STN Database accession No. 903867-80-1.

\* cited by examiner

SEQUENCE LISTING

```
<160> NUMBER OF SEQ ID NOS: 6

<210> SEQ ID NO 1
<211> LENGTH: 29
<212> TYPE: PRT
<213> ORGANISM: Artificial Sequence
<220> FEATURE:
<223> OTHER INFORMATION: Known peptide for assay

<400> SEQUENCE: 1

Arg Ser Pro Ser Tyr Gly Arg Ser Arg Ser Arg Ser Arg Ser
1               5                   10                  15

Arg Ser Arg Ser Arg Ser Asn Ser Arg Ser Arg Ser Tyr
            20                  25

<210> SEQ ID NO 2
<211> LENGTH: 21
<212> TYPE: DNA
<213> ORGANISM: Artificial Sequence
<220> FEATURE:
<223> OTHER INFORMATION: PCR Primer

<400> SEQUENCE: 2
aaggcgaggc agcttgagtt a                                            21

<210> SEQ ID NO 3
<211> LENGTH: 26
<212> TYPE: DNA
<213> ORGANISM: Artificial Sequence
<220> FEATURE:
<223> OTHER INFORMATION: PCR Primer

<400> SEQUENCE: 3
tctgtatcag tctttcctgg tgagag                                       26
```

```
<210> SEQ ID NO 4
<211> LENGTH: 20
<212> TYPE: DNA
<213> ORGANISM: Artificial Sequence
<220> FEATURE:
<223> OTHER INFORMATION: PCR Primer

<400> SEQUENCE: 4
gagcaagaca agaaaatccc                                              20

<210> SEQ ID NO 5
<211> LENGTH: 19
<212> TYPE: DNA
<213> ORGANISM: Artificial Sequence
<220> FEATURE:
<223> OTHER INFORMATION: PCR Primer

<400> SEQUENCE: 5
cctcggcttg tcacatctg                                               19

<210> SEQ ID NO 6
<211> LENGTH: 20
<212> TYPE: DNA
<213> ORGANISM: Artificial Sequence
<220> FEATURE:
<223> OTHER INFORMATION: PCR Primer

<400> SEQUENCE: 6
gtgagagatc tgcaagtacg                                              20
```

COMPOUNDS

RELATED APPLICATIONS

This application is the U.S. National Stage of International Patent Application No. PCT/GB2016/053199, filed Oct. 14, 2016, which is hereby incorporated by reference in its entirety, and which claims priority to GB Patent Application No. 1518365.0, filed Oct. 16, 2015.

SEQUENCE LISTING

The sequences listed in the accompanying Sequence Listing are presented in accordance with 37 C.F.R. 1.822. The Sequence Listing is submitted as an ASCII computer readable text file, which is incorporated by reference herein.

FIELD OF THE INVENTION

The present invention relates to anti-angiogenic treatments and compounds for use in anti-angiogenic treatments, particularly of conditions characterised by neovascularisation such as, for example, age-related macular degeneration and cancer.

The present invention also relates to treatments of hyperpermeability disorders and compounds for use in treating hyperpermeability disorders.

The present invention also relates to treatments of neuropathic and neurodegenerative disorders and compounds for use in treating neuropathic and neurodegenerative disorders, such as, for example, Alzheimer's disease.

The present invention also relates to pain treatments, and compounds for use in treating pain.

The present invention also relates to methods of treating or preventing fibrosis, for example idiopathic pulmonary fibrosis, and compounds for use in such methods.

BACKGROUND TO THE INVENTION

Age-related macular degeneration (AMD), a disease causing vision loss that affects the central area of the macula, is the leading cause of blindness in people over 50 years of age (Bressler, 2004). Exudative AMD is the most severe form of AMD (Ferris et al., 1984) primarily arising from the choroidal circulation beneath the macula and characterized by choroidal neovascularization (CNV). CNV, the abnormal growth of new vessels from the choroid into the retinal pigmented epithelium (RPE) (Patz et al., 1977), is thought to lead to visual loss due to the leakage of blood and serous fluid beneath the RPE that eventually leads to loss of photoreceptors, retinal detachment and dense macular scarring (Fine et al., 2000; Campochiaro et al., 2006). Vascular endothelial growth factor (VEGF), a key factor in angiogenesis and vascular leakage (Dvorak et al., 1995) is up-regulated during the progression of CNV (D'Amore, 1994; Spilsbury et al., 2000; Anderson et al., 2002; Das et al., 2003) and has become the lead therapeutic target for the treatment of exudative-AMD.

VEGF is a complex gene that is alternatively spliced to form a family of multiple isoforms (Leung et al., 1989; Jingjing et al., 1999), each isoform differing in biological property, activity and function (Houck et al., 1991). Most cells commonly express isoforms $VEGF_{121}$, $VEGF_{165}$, and $VEGF_{189}$, whereas $VEGF_{145}$ and $VEGF_{206}$ are comparatively rare. The majority of VEGF isoforms contain exons 1-5 (the exception being $VEGF_{111}$ (Mineur et al., 2007)) but differing portions of exons 6 and 7 that encode heparin sulfate (HS) binding domains.

In 2002 differential splicing of the eighth exon was demonstrated from a proximal splice site (PSS) to a distal splice site (DSS) 66 bases downstream (Bates et al., 2002; Woolard et al., 2004). Alternative splicing in this region generated a second family of isoforms ($VEGF_{xxx}b$), noted for their anti-angiogenic properties (Perrin et al., 2005). WO 03/012105, the contents of which are incorporated herein by reference in its entirety describes the alternatively spliced isoforms, and their therapeutic significance.

During pathological angiogenesis pro-angiogenic isoforms are selectively upregulated (Bates et al., 2002; Varey et al., 2008; Pritchard-Jones et al., 2007), suggesting $VEGF_{xxx}$ and $VEGF_{xxx}b$ may have separate regulatory pathways. These anti-angiogenic isoforms, such as $VEGF_{165}b$ and $VEGF_{121}b$ have been shown to be potently anti-angiogenic in animal models of retinal and choroidal neovascularisation, following intra-ocular injection (Hua et al 2008), and result in both endothelial and retinal epithelial cell cytoprotection (Magnussen et al 2010).

The first therapy to be FDA approved for the treatment of neovascular AMD in December 2004 was a $VEGF_{165}$, $VEGF_{189}$ and $VEGF_{206}$ specific aptamer, Pegaptanib Sodium (Macugen). During clinical trials pegaptinib dose-dependently reduced the risk of severe visual acuity loss and slowed the progression of neovascular AMD, but did not result in significant improvement in vision. In 2006 Ranibizumab (Lucentis), a novel humanized anti-VEGF antibody fragment, was FDA approved for the treatment of neovascular AMD. Its approval was based on the results of three clinical trials where, approximately 95% of patients treated monthly with Lucentis (0.5 mg) maintained visual acuity (defined as the loss of <15 letters) and ≤40% improved vision (defined as the gain of ≥15 letters) at one year compared with 11% in the sham control treated group (Rosenfeld et al., 2006; Brown et al., 2006; Brown et al., 2009). Current treatment regimes require Lucentis administration by intra-ocular injection as often as monthly (Brown et al., 2009; Schmidt-Erfuth et al., 2011). Such intraocular injections result in increased intraocular pressure (Good et al., 2010) and a risk, albeit minor, of endopthalmitis and other severe adverse effects (Jager et al., 2004). Furthermore, bevicizumab (Avastin), an anti-VEGF antibody from which Lucentis was derived, was shown to bind $VEGF_{165}b$ with equal potency to $VEGF_{165}$, thus targeting both pro and anti-angiogenic VEGF isoforms (Varey et al 2008).

As both the anti-angiogenic and angiogenic isoforms of VEGF are derived from the same gene, the control of isoform family is a result of the control of alternative splicing. We have recently identified some of the pathways that control the splicing of VEGF at the proximal splice site, implicating the RNA binding protein SRSF1 (Nowak et al., 2008; Amin et al., 2011) and its kinase SRPK1 (Sanford et al., 2005) as key requirements for the decision by cells to use the proximal splice site, and hence generate pro-angiogenic isoforms of VEGF (Nowak et al., 2008; Nowak et al., 2010). Knockdown of SRPK1 potently reduced VEGF mediated angiogenesis in vivo in tumours and inhibition of SRPK1 and 2 reduced angiogenesis in vivo (Amin et al., 2011).

WO 2008/110777, WO 2009/106855, WO 2010/058227, and WO 2011/148200, the disclosures of which are incorporated herein by reference, describe therapeutic and other physiological uses of agents which direct expression in favour of the $VEGF_{xxx}b$ isoforms. SRPK inhibitors can in principle constitute such agents.

WO 2005/063293 describes a class of SRPK inhibitors including SRPIN340 and derivatives and analogues thereof.

WO 2014/060763 describes SRPK inhibitors targeting SRPK1 specifically for use as anti-angiogenic agents, neuroprotective agents, agents for use in treating or preventing hyperpermeability disorders, as agents for treating pain, and as agents for reducing the risk of, or treatment of, pre-eclampsia.

The development of agents for directing expression of $VEGF_{xxx}b$ isoforms represents a new era not only in the treatment of, for example, neovascular AMD, but all other diseases in which $VEGF_{xxx}b$ is implicated.

The present invention is based in part on new small molecule inhibitors targeting SRPK1 specifically for use as anti-angiogenic agents, neuroprotective agents, agents for use in treating or preventing hyperpermeability disorders, as agents for treating pain, and as agents for treating or preventing fibrosis.

The present invention is also based at least in part on the surprising finding that these low molecular weight compounds could be used topically to inhibit CNV progression.

SUMMARY OF THE INVENTION

In a first aspect the invention provides a compound of Formula (I):

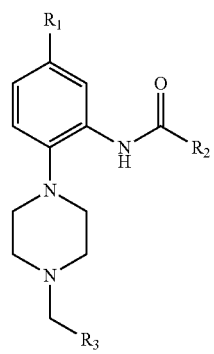

(I)

or a pharmaceutically acceptable salt, solvate, hydrate or prodrug thereof; wherein:

$R_1$ is $CF_3$, hydrogen, methyl, $CHF_2$, Cl, or cyclopropyl; and either $R_2$ is methyl, a 5- or 6-membered aromatic heterocycle, phenyl, or a condensed aromatic heterocycle, each of which may optionally have one or more substituent; and $R_3$ is a 5-membered aromatic heterocycle which may optionally have one or more substituent; or $R_2$ is methyl, a 6-membered aromatic heterocycle, phenyl, or a condensed aromatic heterocycle, each of which may optionally have one or more substituent; and $R_3$ is a condensed aromatic heterocycle, which may optionally have one or more substituent; for use in the treatment or prevention of ocular neovascularisation.

The invention also provides a compound of Formula (Ia):

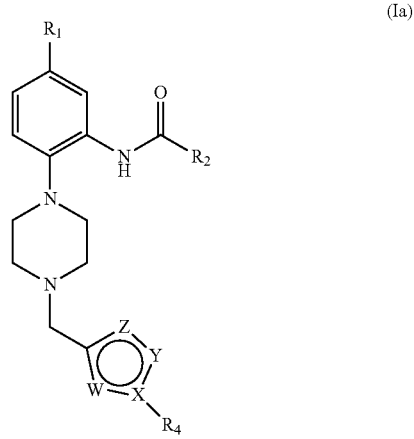

(Ia)

or a pharmaceutically acceptable salt, solvate, hydrate or prodrug thereof; wherein:

$R_1$ is $CF_3$, hydrogen, methyl, $CHF_2$, Cl, or cyclopropyl;

$R_2$ is methyl, a 5- or 6-membered aromatic heterocycle, phenyl or a condensed aromatic heterocycle, each of which may optionally have one or more substituent;

$R_4$ is hydrogen, or a $C_{1-6}$ alkyl group which may optionally have one or more substituent;

W is CH, O, N or S;

X is C or N;

Y is CH, O, N or S; and

Z is CH, N or S;

for use in the treatment or prevention of ocular neovascularisation.

For the avoidance of doubt,

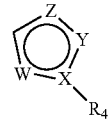

refers to a 5-membered aromatic heterocycle, with any substitution pattern for positions W, X, Y and Z within the bounds defined as above as long as the 5-membered heterocycle remains aromatic and of neutral charge, and each atom has a full valency, with hydrogen completing the valency for any carbon atom whose substituents are not otherwise specified. It will be understood that this definition applies only to the neutral compounds of Formula (Ia) and that corresponding salts may create positive charges on this 5-membered aromatic heterocycle.

The first aspect of the invention also provides respective methods of treatment or prevention of ocular neovascularisation by administration of a compound of Formula (I) or Formula (Ia) to a subject in need of such treatment, and respective uses of a compound of Formula (I) or Formula (Ia) in the preparation of a medicament for treatment or prevention of ocular neovascularisation, for example as a topical treatment.

These compounds of Formula (I) or Formula (Ia) and their pharmaceutically acceptable salts, solvates, hydrates or prodrugs are new and as compounds per se (as well as their use in treatments described herein) they constitute a further aspect of the present invention.

Thus, in a second aspect the invention provides a compound of Formula (I) or a pharmaceutically acceptable salt, solvate, hydrate or prodrug thereof.

The invention also provides a compound of Formula (Ia) or a pharmaceutically acceptable salt, solvate, hydrate or prodrug thereof.

It is surprising and not expected from the prior art that the compounds used in the present invention enable effective treatment or prevention of ocular neovascularisation or topical treatment or prevention of ocular neovascularisation.

Pharmaceutical compositions comprising the novel compounds and the use of the novel compounds and pharmaceutical compositions comprising them in anti-angiogenic treatments (including the treatment and prevention of disorders and diseases characterised by abnormal or excessive angiogenesis), treatments of hyperpermeability disorders, treatments of neuropathic and neurodegenerative disorders, treatment of non-inflammatory pain and methods of treating or preventing fibrosis constitute further aspects of the present invention.

Thus, the present invention also provides (i) methods of treating or preventing disorders and diseases characterized by abnormal or excessive angiogenesis as defined herein; (ii) methods of treating or preventing hyperpermeability disorders as defined herein; (iii) methods of treating or preventing neuropathic and neurodegenerative disorders as defined herein; (iv) methods of treating or preventing non-inflammatory pain; and (v) methods of treating or preventing fibrosis, comprising administering a compound of Formula (I) or Formula (Ia) to a patient in need thereof.

The specific compounds of Formula (I) or Formula (Ia), and preferred or exemplified sub-classes of compounds of Formula (I) or Formula (Ia) as discussed below may be particularly mentioned for use in the present invention.

Examples of the compound of Formula (I) or Formula (Ia) that may be mentioned include those in which $R_1$ is $CF_3$ or Cl.

Particularly mentioned compounds are those in which $R_2$ is a 5- or 6-membered aromatic heterocycle, for example an oxygen-containing 5- or 6-membered heteroaryl group or a nitrogen-containing 5- or 6-membered heteroaryl group, for example a furanyl group, a pyrrolyl group, an oxazolyl group, an isoxazolyl group, a triazolyl group, an oxadiazolyl group, a pyrazolyl group, a thiazolyl group, an imidazolyl group, or a pyridinyl group, each of which may optionally have one or more substituent. In some examples, $R_2$ is a furan-2-yl group or a pyridin-2-yl group, each of which may optionally have one or more substituent, for example a furan-2-yl group with a tetrahydropyranyl substituent or a pyridinyl substituent. In some examples, $R_2$ may be a furan-2-yl group with a 2-pyridyl substituent.

In some examples, $R_2$ is a condensed aromatic heterocycle, which may optionally have one or more substituent. For example, $R_2$ may be an indolyl group, an isoindolyl group, a benzoxazolyl group, a benzimidazolyl group, a coumarinyl group, a quinolyl group or an isoquinolyl group.

In some examples, $R_2$ is selected from the group consisting of:

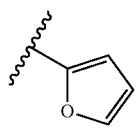 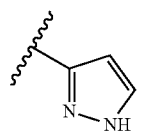 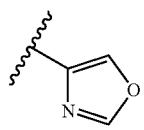

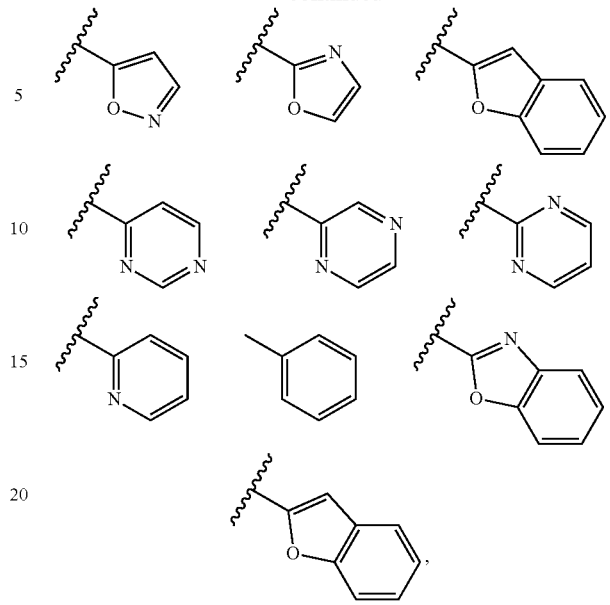

each of which may optionally have one or more substituent.

Particularly mentioned compounds of Formula (I) are those in which $R_3$ of Formula (I) is a 5-membered aromatic heterocycle, for example an oxygen-containing 5-membered heteroaryl group or a nitrogen-containing 5-membered heteroaryl group, each of which may comprise one or more additional heteroatoms. For example, $R_3$ of Formula (I) may be a furanyl group, a pyrrolyl group, an oxazolyl group, an isoxazolyl group, a triazolyl group, an oxadiazolyl group, a pyrazolyl group, a thiazolyl group, or an imidazolyl group, each of which may optionally have one or more substituent.

Particularly mentioned compounds of Formula (I) are those represented by Formula (Ia). In particular, compounds of Formula (Ia) include those in which Z=CH or N. Other particularly mentioned compounds of Formula (Ia) are those in which X=C. Other particularly mentioned compounds of Formula (Ia) are those in which X=N. It will be understood that when any of W, X, Y or Z is C or CH, that at least one other of the remaining positions will comprise O, N or S in order to maintain the heteroatomic nature of the cycle. For example, particularly mentioned compounds are those of Formula (Ia) in which W, X, Y and Z are selected such that the 5-membered aromatic heterocycle is selected from the group consisting of:

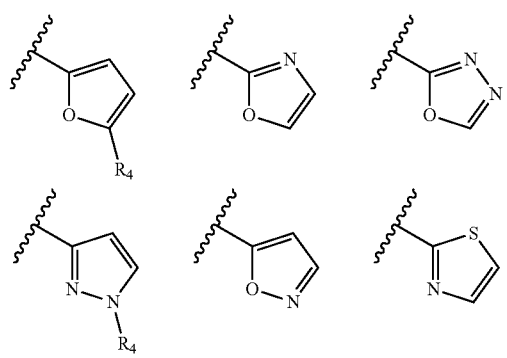

-continued

Of these compounds, R₄ may be hydrogen or a methyl group, which optionally may have a substituent. For example, R₄ may be a methyl group substituted with a phenyl group or 5- or 6-membered aromatic heterocycle as described herein.

Particularly mentioned compounds are those of Formula (Ia) in which $R_1$ is $CF_3$ or Cl; $R_2$ is a 5- or 6-membered aromatic heterocycle; $R_4$ is hydrogen or methyl and Z═CH or N.

Particularly mentioned compounds of Formula (I) are those in which:

$R_1$ is $CF_3$, hydrogen, methyl, $CHF_2$, Cl, or cyclopropyl;

$R_2$ is methyl, a 6-membered aromatic heterocycle, phenyl, or a condensed aromatic heterocycle, each of which may optionally have one or more substituent; and $R_3$ is a condensed aromatic heterocycle, which may optionally have one or more substituent.

Of these, particularly mentioned compounds of Formula (I) are those in which $R_2$ is a nitrogen-containing 6-membered aromatic heterocycle, for example a 2-, 3- or 4-pyridyl group and $R_3$ is an indolyl group, an isoindolyl group, a benzoxazolyl group, a benzimidazolyl group, a coumarinyl group, a quinolyl group or an isoquinolyl group.

Particularly mentioned compounds of Formula (I) are those in which $R_2$ is a 2-pyridyl group and $R_3$ is an indolyl group, an isoindolyl group, a benzoxazolyl group, a benzimidazolyl group, a coumarinyl group, a quinolyl group or an isoquinolyl group.

In one example, the compound of Formula (I) is not N-(2-(4-((1H-indol-3-yl)methyl)piperazin-1-yl)-5-(trifluoromethyl)-phenyl)-5-(pyridin-4-yl)furan-2-carboxamide.

Particular compounds which may be mentioned include:

N-(2-(4-(furan-2-ylmethyl)piperazin-1-yl)-5-(trifluoromethyl)phenyl)-5-(pyridin-4-yl)furan-2-carboxamide;

N-(2-(4-((5-methyl-1,3,4-oxadiazol-2-yl)methyl)piperazin-1-yl)-5-(trifluoromethyl)phenyl)-5-(pyridin-4-yl)furan-2-carboxamide;

N-(2-(4-((1-benzyl-1H-1,2,3-triazol-4-yl)methyl)piperazin-1-yl)-5-(trifluoromethyl)phenyl)-5-methylfuran-2-carboxamide;

5-methyl-N-(2-(4-((5-methylfuran-2-yl)methyl)piperazin-1-yl)-5-(trifluoromethyl)phenyl)furan-2-carboxamide;

5-methyl-N-(2-(4-((furan-2-ylmethyl)piperazin-1-yl)-5-(trifluoromethyl)phenyl)furan-2-carboxamide;

N-(2-(4-((1H-pyrazol-3-yl)methyl)piperazin-1-yl)-5-(trifluoromethyl)-phenyl)furan-2-carboxamide;

N-(2-(4-((1-methyl-1H-pyrazol-3-yl)methyl)piperazin-1-yl)-5-(trifluoromethyl)phenyl)furan-2-carboxamide;

N-(2-(4-(thiazol-4-ylmethyl)piperazin-1-yl)-5-(trifluoromethyl)-phenyl)furan-2-carboxamide N-(2-(4-((1H-imidazol-4-yl)methyl)piperazin-1-yl)-5-(trifluoromethyl)-phenyl)-5-(pyridin-4-yl)furan-2-carboxamide;

N-(2-(4-(thiazol-5-ylmethyl)piperazin-1-yl)-5-(trifluoromethyl)-phenyl)furan-2-carboxamide N-(2-(4-((1H-pyrazol-3-yl)methyl)piperazin-1-yl)-5-(trifluoromethyl)-phenyl)-5-(tetrahydro-2H-pyran-4-yl)furan-2-carboxamide;

N-(2-(4-((5-methylfuran-2-yl)methyl)piperazin-1-yl)-5-(trifluoromethyl)-phenyl)-5-(pyridin-4-yl)furan-2-carboxamide;

N-(2-(4-(oxazol-2-ylmethyl)piperazin-1-yl)-5-(trifluoromethyl)phenyl)-5-(pyridin-4-yl)furan-2-carboxamide;

N-(2-(4-(oxazol-4-ylmethyl)piperazin-1-yl)-5-(trifluoromethyl)phenyl)-5-(pyridin-4-yl)furan-2-carboxamide;

N-(2-(4-(oxazol-5-ylmethyl)piperazin-1-yl)-5-(trifluoromethyl)phenyl)-5-(pyridin-4-yl)furan-2-carboxamide;

5-(tetrahydro-2H-pyran-4-yl)-N-(2-(4-(thiazol-4-ylmethyl)piperazin-1-yl)-5-(trifluoromethyl)phenyl)furan-2-carboxamide;

N-(2-(4-(thiazol-2-ylmethyl)piperazin-1-yl)-5-(trifluoromethyl)-phenyl)furan-2-carboxamide 5-(pyridin-4-yl)-N-(2-(4-(thiazol-2-ylmethyl)piperazin-1-yl)-5-(trifluoromethyl)phenyl)furan-2-carboxamide;

5-(pyridin-4-yl)-N-(2-(4-(thiazol-4-ylmethyl)piperazin-1-yl)-5-(trifluoromethyl)phenyl)furan-2-carboxamide;

5-(pyridin-4-yl)-N-(2-(4-(thiazol-2-ylmethyl)piperazin-1-yl)-5-(trifluoromethyl)phenyl)furan-2-carboxamide;

N-(2-(4-((1H-pyrazol-3-yl)methyl)piperazin-1-yl)-5-(trifluoromethyl)-phenyl)-5-(pyridin-4-yl)furan-2-carboxamide;

N-(2-(4-((1-methyl-1H-pyrazol-3-yl)methyl)piperazin-1-yl)-5-(trifluoromethyl)phenyl)-5-(pyridin-4-yl)furan-2-carboxamide;

N-(5-chloro-2-(4-(furan-2-ylmethyl)piperazin-1-yl)phenyl)-5-(pyridin-4-yl)furan-2-carboxamide;

N-(5-chloro-2-(4-(oxazol-4-ylmethyl)piperazin-1-yl)phenyl)-5-(pyridin-4-yl)furan-2-carboxamide;

N-(2-(4-(furan-2-ylmethyl)piperazin-1-yl)-5-(trifluoromethyl)phenyl)-picolinamide;

N-(5-chloro-2-(4-(furan-2-ylmethyl)piperazin-1-yl)phenyl)picolinamide;

N-(2-(4-(thiazol-2-ylmethyl)piperazin-1-yl)-5-(trifluoromethyl)phenyl)-picolinamide;

N-(2-(4-(thiazol-4-ylmethyl)piperazin-1-yl)-5-(trifluoromethyl)phenyl)-picolinamide;

N-(2-(4-(thiazol-5-ylmethyl)piperazin-1-yl)-5-(trifluoromethyl)phenyl)-picolinamide;

N-(2-(4-((1H-pyrazol-3-yl)methyl)piperazin-1-yl)-5-(trifluoromethyl)-phenyl)picolinamide;

N-(2-(4-((1-methyl-1H-pyrazol-3-yl)methyl)piperazin-1-yl)-5-(trifluoromethyl)phenyl)picolinamide;

N-(2-(4-(furan-2-ylmethyl)piperazin-1-yl)-5-(trifluoromethyl)phenyl)-isonicotinamide;

N-(2-(4-(oxazol-4-ylmethyl)piperazin-1-yl)-5-(trifluoromethyl)phenyl)-picolinamide;

N-(2-(4-(furan-2-ylmethyl)piperazin-1-yl)-5-(trifluoromethyl)phenyl)acetamide;

N-(2-(4-(furan-3-ylmethyl)piperazin-1-yl)-5-(trifluoromethyl)phenyl)picolinamide;

N-(2-(4-((5-methylfuran-2-yl)methyl)piperazin-1-yl)-5-(trifluoromethyl)phenyl)-picolinamide;

N-(2-(4-(1H-imidazol-4-ylmethyl)piperazin-1-yl)-5-(trifluoromethyl)phenyl)-picolinamide;

N-(2-(4-((1H-imidazol-4-yl)methyl)piperazin-1-yl)-5-(trifluoromethyl)phenyl)-5-(pyridin-4-yl)furan-2-carboxamide;
N-(2-(4-(furan-3-ylmethyl)piperazin-1-yl)-5-(trifluoromethyl)phenyl)-5-(tetrahydro-2H-pyran-4-yl)furan-2-carboxamide;
N-(2-(4-((5-methylfuran-2-yl)methyl)piperazin-1-yl)-5-(trifluoromethyl)phenyl)-5-(tetrahydro-2H-pyran-4-yl)furan-2-carboxamide;
N-(2-(4-(furan-3-ylmethyl)piperazin-1-yl)-5-(trifluoromethyl)phenyl)-5-methylfuran-2-carboxamide;
5-methyl-N-(2-(4-((5-methylfuran-2-yl)methyl)piperazin-1-yl)-5-(trifluoromethyl)phenyl)furan-2-carboxamide;
N-(2-(4-(furan-3-ylmethyl)piperazin-1-yl)-5-(trifluoromethyl)phenyl)furan-2-carboxamide;
N-(2-(4-((5-methylfuran-2-yl)methyl)piperazin-1-yl)-5-(trifluoromethyl)phenyl)furan-2-carboxamide;
N-(2-(4-((1H-indol-3-yl)methyl)piperazin-1-yl)-5-(trifluoromethyl)phenyl)picolinamide;
N-(2-(4-((5-methyl-1,3,4-oxadiazol-2-yl)methyl)piperazin-1-yl)-5-(trifluoromethyl)phenyl)furan-2-carboxamide;
N-(2-(4-(oxazol-4-ylmethyl)piperazin-1-yl)-5-(trifluoromethyl)-phenyl)furan-2-carboxamide;
N-(2-(4-(oxazol-4-ylmethyl)piperazin-1-yl)-5-(trifluoromethyl)phenyl)oxazole-2-carboxamide;
N-(2-(4-(oxazol-4-ylmethyl)piperazin-1-yl)-5-(trifluoromethyl)phenyl)isoxazole-5-carboxamide;
N-(2-(4-(oxazol-4-ylmethyl)piperazin-1-yl)-5-(trifluoromethyl)-phenyl)benzofuran-2-carboxamide;
N-(2-(4-(oxazol-4-ylmethyl)piperazin-1-yl)-5-(trifluoromethyl)phenyl)pyrazine-2-carboxamide;
N-(2-(4-(oxazol-4-ylmethyl)piperazin-1-yl)-5-(trifluoromethyl)phenyl)-1H-pyrazole-3-carboxamide;
N-(2-(4-(oxazol-4-ylmethyl)piperazin-1-yl)-5-(trifluoromethyl)phenyl)pyrimidine-2-carboxamide;
N-(2-(4-(oxazol-4-ylmethyl)piperazin-1-yl)-5-(trifluoromethyl)phenyl)benzo[d]oxazole-2-carboxamide;
N-(2-(4-(oxazol-4-ylmethyl)piperazin-1-yl)-5-(trifluoromethyl)phenyl)pyrimidine-4-carboxamide;
N-(2-(4-(oxazol-4-ylmethyl)piperazin-1-yl)-5-(trifluoromethyl)phenyl)oxazole-4-carboxamide;
N-(2-(4-(oxazol-4-ylmethyl)piperazin-1-yl)-5-(trifluoromethyl)phenyl)-6-(tetrahydro-2H-pyran-4-yl)picolinamide;
N-(2-(4-(oxazol-4-ylmethyl)piperazin-1-yl)-5-(trifluoromethyl)phenyl)-5-(tetrahydro-2H-pyran-4-yl)picolinamide;
N-(2-(4-(furan-3-ylmethyl)piperazin-1-yl)-5-(trifluoromethyl)phenyl)-5-(pyridin-4-yl)furan-2-carboxamide;
N-(2-(4-((1H-pyrazol-4-yl)methyl)piperazin-1-yl)-5-(trifluoromethyl)phenyl)-5-(pyridin-4-yl)furan-2-carboxamide;
N-(2-(4-(isoxazol-5-ylmethyl)piperazin-1-yl)-5-(trifluoromethyl)phenyl)picolinamide;
N-(2-(4-(isoxazol-5-ylmethyl)piperazin-1-yl)-5-(trifluoromethyl)phenyl)furan-2-carboxamide;
N-(2-(4-(isoxazol-5-ylmethyl)piperazin-1-yl)-5-(trifluoromethyl)phenyl)-5-(tetrahydro-2H-pyran-4-yl)furan-2-carboxamide;
N-(2-(4-(isoxazol-4-ylmethyl)piperazin-1-yl)-5-(trifluoromethyl)phenyl)-5-(tetrahydro-2H-pyran-4-yl)furan-2-carboxamide;
N-(2-(4-(isoxazol-4-ylmethyl)piperazin-1-yl)-5-(trifluoromethyl)phenyl)furan-2-carboxamide;
N-(2-(4-(isoxazol-4-ylmethyl)piperazin-1-yl)-5-(trifluoromethyl)phenyl)-picolinamide;
N-(2-(4-(isoxazol-4-ylmethyl)piperazin-1-yl)-5-(trifluoromethyl)phenyl)-5-(pyridin-4-yl)furan-2-carboxamide;
N-(2-(4-(isoxazol-5-ylmethyl)piperazin-1-yl)-5-(trifluoromethyl)phenyl)-5-(pyridin-4-yl)furan-2-carboxamide;
5-(tetrahydro-2H-pyran-4-yl)-N-(2-(4-(thiazol-5-ylmethyl)piperazin-1-yl)-5-(trifluoromethyl)phenyl)furan-2-carboxamide;
N-(2-(4-(oxazol-4-ylmethyl)piperazin-1-yl)-5-(trifluoromethyl)phenyl)benzamide;
N-(2-(4-(furan-3-ylmethyl)piperazin-1-yl)-5-(trifluoromethyl)phenyl)picolinamide;
N-(2-(4-(1H-imidazol-4-ylmethyl)piperazin-1-yl)-5-(trifluoromethyl)phenyl)picolinamide;
N-(2-(4-((1H-indol-3-yl)methyl)piperazin-1-yl)-5-(trifluoromethyl)-phenyl)-5-(pyridin-4-yl)furan-2-carboxamide; and
N-(2-(4-((1H-indol-3-yl)methyl)piperazin-1-yl)-5-(trifluoromethyl)phenyl)furan-2-carboxamide.

DETAILED DESCRIPTION OF THE INVENTION

The compounds of the present invention are SRPK1-specific inhibitors and may therefore be used in methods of treating or preventing any disease or condition in which SRPK1 is implicated. Such conditions and treatments will now be described.

Anti-Angiogenic Treatment

The compounds of the present invention may be used in anti-angiogenic treatments. The anti-angiogenic treatment preferably includes the treatment or prevention of any disease or disorder associated with abnormal angiogenesis or abnormal over-production of pro-angiogenic VEGF isoforms ($VEGF_{xxx}$). Such diseases and disorders include, for example, vascular disease (e.g. vasoconstriction and disorders characterised by vasoconstriction, and cardiovascular disease), malignant and benign neoplasia (e.g. angiogenesis-dependent cancers, for example tumorous cancers), tumor metastasis, inflammatory disorders, diabetes, diabetic retinopathy and other complications of diabetes (e.g. diabetic neovascularisation), trachoma, retrolental hyperplasia, neovascular glaucoma, age-related macular degeneration, haemangioma, immune rejection of implanted corneal tissue, corneal angiogenesis associated with ocular injury or infection, Osler-Webber Syndrome, myocardial angiogenesis, wound granulation, telangiectasia, hemophiliac joints, angiofibroma, telangiectasia psoriasis scleroderma, pyogenic granuloma, rubeosis, obesity, arthritis (e.g. rheumatoid arthritis), hematopoieses, vasculogenesis, gingivitis, atherosclerosis, endometriosis, neointimal hyperplasia, psoriasis, hirsutism and proliferative retinopathy. The anti-angiogenic treatment according to the present invention may also include non-therapeutic treatments performed on healthy subjects, for example to inhibit vascular development for cosmetic purposes. For further details on diseases and disorders associated with abnormal angiogenesis, and on anti-angiogenic treatments, see WO 2008/110777, the contents of which are incorporated herein by reference.

In particular, the compounds of the present invention may be used in the treatment or prevention of ocular neovascularisation, which may include retinal neovascularisation or choroidal neovascularisation or age-related macular degeneration. In addition, the compounds of the present invention may be used in the treatment or prevention of malignant neoplasias or cancers, for example prostate cancer, melanoma, colorectal cancer and breast cancer.

Microvascular Hyperpermeability Disorders, Disorders of Epithelial Cell Survival and Disorders of Fenestrations of Epithelial Filtration Membranes The compounds of the present invention, as SRPK1 inhibitors, may also be used as therapeutic agents in treating other disorders in which the alternatively spliced $VEGF_{xxx}b$ isoform has been implicated. For example, it has been shown in WO 2010/058227, the contents of which are incorporated herein by reference, that $VEGF_{xxx}b$ is active against a range of microvascular hyperpermeability disorders, disorders of epithelial cell survival and disorders of fenestrations of epithelial filtration membranes.

Microvascular hyperpermeability, disorders of regulation of the pro-angiogenic pro-permeability properties of $VEGF_{xxx}$ isoforms, disorders of epithelial cell survival and permeability, and/or disorders in the nature (for example the number density and/or size) of fenestrations of epithelial filtration membranes underlie a number of serious medical conditions.

Examples of such conditions include, for example, proteinuria, uraemia, microalbuminuria, hypoalbuminemia, renal hyperfiltration, nephrotic syndrome, renal failure, pulmonary hypertension, capillary hyperpermeability, microaneurysms, oedema and vascular complications of diabetes.

Examples of such vascular complications of diabetes include, for example, diabetic retinopathy, both proliferative and non-proliferative, and diabetic nephropathy. Vascular complications of diabetes can be associated with either Type I or Type II diabetes.

The microvascular hyperpermeability disorder may particularly be a renal disorder, for example a permeability disorder of the GFB, for example a permeability disorder of the podocytes.

Examples of disorders where treatment to support epithelial cell survival would be effective are as follows:

acute pulmonary fibrotic disease, adult respiratory distress syndrome, adult respiratory distress syndrome, advanced cancer, allergic respiratory disease, alveolar injury, angiogenesis, arthritis, ascites, asthma, asthma or edema following burns, atherosclerosis, autoimmune diseases, bone resorption, bullous disorder associated with subepidermal blister formation including bullous pemphigoid, cardiovascular condition, certain kidney diseases associated with proliferation of glomerular or mesangial cells, chronic and allergic inflammation, chronic lung disease, chronic occlusive pulmonary disease, cirrhosis, corneal angiogenisis, corneal disease, coronary and cerebral collateral vascularization, coronary restenosis, damage following heart disease, dermatitis herpetiformis, diabetes, diabetic nephropathy, diabetic retinopathy, endotoxic shock, erythema multiforme, fibrosis, glomerular nephritis, glomerulonophritis, graft rejection, gram negative sepsis, hemangioma, hepatic cirrhosis, hepatic failure, Herpes Zoster, host-versus-graft reaction (ischemia reperfusion injury and allograft rejections of kidney, liver, heart, and skin), impaired wound healing in infection, infection by Herpes simplex, infection from human immunodeficiency virus (HIV), inflammation, cancer, inflammatory bowel disease (Crohn's disease and ulcerative colitis), inflammatory conditions, in-stent restenosis, in-stent stenosis, ischemia, ischemic retinal-vein occlusion, ischemic retinopathy, Kaposi's sarcoma, keloid, liver disease during acute inflammation, lung allograft rejection (obliterative bronchitis), lymphoid malignancy, macular degeneration retinopathy of prematurity, myelodysplastic syndromes, myocardial angiogenesis, neovascular glaucoma, non-insulin-dependent diabetes mellitus (NIDDM), obliterative bronchiolitis, ocular conditions or diseases, ocular diseases associated with retinal vessel proliferation, Osier-Weber-Rendu disease, osteoarthritis, ovarian hyperstimulation syndrome, Paget's disease, pancreatitis, pemphigoid, polycystic kidney disease, polyps, postmenopausal osteoperosis, preeclampsia, psoriasis, pulmonary edema, pulmonary fibrosis, pulmonary sarcoidosis, restenosis, restenosis, retinopathy including diabetic retinopathy, retinopathy of prematurity and age related macular degeneration; rheumatoid arthritis, rheumatoid arthritis, rubeosis, sarcoidosis, sepsis, stroke, synovitis, systemic lupus erythematosus, throiditis, thrombic micoangiopathy syndromes, transplant rejection, trauma, tumor-associated angiogenesis, vascular graft restenosis, vascular graft restenosis, von Hippel Lindau disease, wound healing.

The present invention may be used in the treatment of macular dystrophy. This includes: Stargardt disease/fundus flavimaculatus; Stargardt-like macular dystrophy; Stargardt-like macular dystrophy; Autosomal dominant "bull'seye" macular dystrophy Best macular dystrophy; Adult vitelliform dystrophy; Pattern dystrophy; Doyne honeycomb retinal dystrophy; North Carolina macular dystrophy; Autosomal dominant macular dystrophy resembling MCDR1; North Carolina-like macular dystrophy associated with deafness; Progressive bifocal chorioretinal atrophy; Sorsby's fundus dystrophy; Central areolar choroidal dystrophy; Dominant cystoid macular dystrophy; Juvenile retinoschisis; Occult Macular Dystrophy; Non-familial Occult Macular Dystrophy.

The disorder may particularly be a disorder of the retinal epithelium, such as geographic atrophy, or age related macular degeneration.

For further details on of microvascular hyperpermeability disorders, disorders of epithelial cell survival and disorders of fenestrations of epithelial filtration membranes, and the treatment thereof, see WO 2010/058227, the contents of which are incorporated herein by reference.

Neuropathic and Neurodegenerative Disorders

The compounds of the present invention, as SRPK1 inhibitors, may also be used as therapeutic agents in treating other disorders in which the alternatively spliced $VEGF_{xxx}b$ isoform has been implicated. For example, it has been shown in WO 2009/106855, the contents of which are incorporated herein by reference, that $VEGF_{xxx}b$ has neuroprotective and neuroregenerative effects.

Neuropathic disorders to be treated or prevented according to the present invention include neuropathic pain and diabetic and other neuropathies.

Neurodegenerative disorders to be treated or prevented according to the present invention include neurodegeneration of the cognitive and non-cognitive types, neuromuscular degeneration, motor-sensory neurodegeneration, ocular neurodegeneration.

The activities of the proteins of the $VEGF_{xxx}b$ family are predicted to both actively prevent and actively reverse the conditions and disorders described above.

Furthermore, since mild cognitive dysfunction is often associated with the normal state in certain classes of healthy people, for example the aged, persons under stress, tired or exhausted persons, the present invention is also applicable to non-therapeutic treatments of healthy people to adjust or normalise their cognitive function and behaviour, including thinking, memory, learning, concentration and reasoning.

Still further, since neuroregeneration can assist in normalising brain neural networks in subjects having psychiatric or behavioural abnormalities, whether or not these are diagnosable as one or more recognised psychiatric condition, the present invention is also applicable to therapeutic treatment of persons having psychiatric disorders and to non-therapeutic treatment of physically healthy people to adjust their cognition and behaviour towards the normal state.

For example, the present invention provides for the treatment or prevention of: pain (for example, neuropathic pain), dementia, age-related cognitive impairment, Alzheimer's disease, senile dementia of the Alzheimer's type (SDAT), Lewy body dementia, vascular dementia, Parkinson's disease, postencephalitic Parkinsonism, depression, schizophrenia, muscular dystrophy including facioscapulohumeral muscular dystrophy (FSH), Duchenne muscular dystrophy, Becker muscular dystrophy and Bruce's muscular dystrophy, Fuchs' dystrophy, myotonic dystrophy, corneal dystrophy, reflex sympathetic dystrophy syndrome (RSDSA), neurovascular dystrophy, myasthenia gravis, Lambert Eaton disease, Huntington's disease, motor neurone diseases including amyotrophic lateral sclerosis (ALS), multiple sclerosis, postural hypotension, traumatic neuropathy or neurodegeneration e.g. following stroke or following an accident (for example, traumatic head injury or spinal cord injury), Batten's disease, Cockayne syndrome, Down syndrome, corticobasal ganglionic degeneration, multiple system atrophy, cerebral atrophy, olivopontocerebellar atrophy, dentatorubral atrophy, pallidoluysian atrophy, spinobulbar atrophy, optic neuritis, sclerosing pan-encephalitis (SSPE), attention deficit disorder, post-viral encephalitis, post-poliomyelitis syndrome, Fahr's syndrome, Joubert syndrome, Guillain-Barre syndrome, lissencephaly, Moyamoya disease, neuronal migration disorders, autistic syndrome, polyglutamine disease, Niemann-Pick disease, progressive multifocal leukoencephalopathy, pseudotumor cerebri, Refsum disease, Zellweger syndrome, supranuclear palsy, Friedreich's ataxia, spinocerebellar ataxia type 2, Rhett syndrome, Shy-Drager syndrome, tuberous sclerosis, Pick's disease, chronic fatigue syndrome, neuropathies including hereditary neuropathy, diabetic neuropathy and mitotic neuropathy, prion-based neurodegeneration, including Creutzfeldt-Jakob disease (CJD), variant CJD, new variant CJD, bovine spongiform encephalopathy (BSE), GSS, FFI, kuru and Alper's syndrome, Joseph's disease, acute disseminated encephalomyelitis, arachnoiditis, vascular lesions of the central nervous system, loss of extremity neuronal function, Charcot-Marie-Tooth disease, Krabbe's disease, leukodystrophies, susceptibility to heart failure, asthma, epilepsy, auditory neurodegeneration, macular degeneration, pigmentary retinitis and glaucoma-induced optic nerve degeneration.

Generally speaking, mental disorders are not diagnosed as "psychiatric disorders" unless the associated behaviours or thoughts cause significant distress to the individual or are disruptive of his or her everyday functioning. There is therefore a borderline between diagnosable disorders and similar, but less severe or disruptive, psychological functions the treatment of which should be considered as non-therapeutic (see below).

Examples of psychiatric disorders with which the present invention is concerned include, without limitation: anxiety disorders (for example, acute stress disorder, panic disorder, agoraphobia, social phobia, specific phobia, obsessive-compulsive disorder, sexual anxiety disorders, post-traumatic stress disorder, body dysmorphic disorder and generalized anxiety disorder), childhood disorders (for example, attention-deficit hyperactivity disorder (ADHD), Asperger's disorder, autistic disorder, conduct disorder, oppositional defiant disorder, separation anxiety disorder and Tourette's disorder), eating disorders (for example, anorexia nervosa and bulimia nervosa), mood disorders (for example, depression, major depressive disorder, bipolar disorder (manic depression), seasonal affective disorder (SAD), cyclothymic disorder and dysthymic disorder), sleeping disorders, cognitive psychiatric disorders (for example, delirium, amnestic disorders), personality disorders (for example, paranoid personality disorder, schizoid personality disorder, schizotypal personality disorder, antisocial personality disorder, borderline personality disorder, histrionic personality disorder, narcissistic personality disorder, avoidant personality disorder, dependent personality disorder and obsessive-compulsive personality disorder), psychotic disorders (for example, schizophrenia, delusional disorder, brief psychotic disorder, schizophreniform disorder, schizoaffective disorder and shared psychotic disorder), and substance-related disorders (for example, alcohol dependence, amphetamine dependence, cannabis dependence, cocaine dependence, hallucinogen dependence, inhalant dependence, nicotine dependence, opioid dependence, phencyclidine dependence and sedative dependence).

For further details on neuropathic and neurodegenerative disorders, and the treatment thereof, see WO 2009/106855, the contents of which are incorporated herein by reference.

Treatment of Pain

The compounds of the present invention, as SRPK1 inhibitors, may also be used as therapeutic agents in treating other disorders in which the alternatively spliced $VEGF_{xxx}b$ isoform has been implicated. For example, it has been shown in WO 2011/148200, the contents of which are incorporated herein by reference, that $VEGF_{xxx}b$ has an analgesic effect on VEGFR2-mediated non-inflammatory pain in mammals.

VEGFR2-mediated non-inflammatory pain to be treated or prevented according to the present invention includes non-inflammatory neuropathic and nociceptive pain where the $VEGFR_2$ receptor is involved in the cause or transmission of the pain. For example, the compounds according to the present invention are predicted to have activity against non-inflammatory allodynia and pain (antiallodynic and analgesic activity). Pain states of this type include chronic pain, whether of the intermittent or constant form. Such pain states may include, for example, low back pain, neuralgia, atypical pains such as atypical facial pain, pain exhibited post-surgery, post-injury (for example, after surgery or injury causing nerve damage) or in association with cancer or with cancer therapy such as cytotoxic or radiation therapy, or neuropathy associated with diabetes (diabetic neuropathy, insulin neuritis) or other systemic or autoimmune disease or pathology, or the treatment thereof, alcoholism or HIV infection, ageing associated neuropathy, or neuropathy of unknown origin.

The activities of the proteins of the $VEGFR_2$ agonists, for example the $VEGF_{xxx}b$ family, are predicted to both actively prevent and actively reverse VEGFR2-mediated non-inflammatory pain.

However, in view of the anti-angiogenic activity of the proteins of the $VEGF_{xxx}b$ family, use of the compounds of the present invention will be restricted to pain in contexts where possible inhibition of angiogenesis would not be detrimental to the patient.

The compounds used in the present invention may be employed in association with one or more different pain treatment agent for the purpose of normalising the sensitivity towards pain of the subject treated (or being co-treated) with the said one or more different pain treatment agent. The term "normalising" means moving the subject's pain sensitivity towards normal levels, and may include enhancement of the sensitivity if the one or more different pain treatment agent causes an excessive reduction in feeling or in sensitivity towards pain. The one or more different pain treatment agent may be selected from pain treatment agents currently known or yet to be devised. Such selection will be well within the skill of the person of ordinary skill in this art. Such combination treatments can enable fine control of pain sensitivity in subjects and minimisation of overall side effects according to the particular condition and needs of the subject.

For further details on pain, and the treatment thereof, see WO 2011/148200, the contents of which are incorporated herein by reference.

Fibrosis

The compounds of the present invention, as SRPK1 inhibitors, may also be used as therapeutic agents in treating other disorders in which the alternatively spliced $VEGF_{xxx}b$ isoform has been implicated. For example, $VEGF_{xxx}b$ has been shown to prevent diseases associated with fibrosis, for example idiopathic pulmonary fibrosis, a condition that causes scarring of the lungs through excessive fibroblast production. Since anti-VEGF agents such as nintedanib have been shown to be effective in treating pulmonary fibrosis, the compounds of the present invention also find use in methods of preventing pulmonary fibrosis, for example idiopathic pulmonary fibrosis through their ability to cause alternative splicing to reduce levels of $VEGF_{xxx}a$ and increase levels of $VEGF_{xxx}b$. Thus, the present invention also provides methods of preventing or treating fibrosis, for example pulmonary fibrosis, by administering a compound of Formula (I) or Formula (Ia) to a subject in need thereof.

Active Compounds

Compounds of the present invention are as defined by Formula (I) and have been shown to be inhibitors of the kinase SRPK1, and thus are useful in treatments of diseases as described herein in which $VEGF_{xxx}b$ and/or SRPK1 has been shown to be implicated. The compounds of the present invention may be SRPK1-specific inhibitors.

The compounds of the present invention may be synthesised by any known method. An exemplary synthesis is described below in the Examples.

Co-Administration

The compounds of the present invention may, if desired, be co-administered with one or more additional active agent, for example one or more agent selected from, but not limited to, cholinesterase inhibitors, dopamine agonists (e.g. L-dopa), COMT inhibitors, MAO-B inhibitors, anti-cholinergics, acetylcholine agonists, serotonin agonists, AMPA receptor agonists, GABA receptor agonists, NMDA receptor agonists, β-adrenoceptor agonists, digoxin, dobutamine, anti-inflammatories, neurotrophic factors, statins, adenosine A2a receptor antagonists, aldose reductase inhibitors, immunomodulators, cannabinoid agonists, interferon or tricyclic anti-depressants.

Definitions

In the definition of Formula (I) or Formula (Ia) herein:

"$C_{1-6}$ alkyl group" refers to a linear or branched alkyl group comprising one to six carbon atoms, which is a monovalent group derived by removing an arbitrary hydrogen atom from an aliphatic hydrocarbon consisting of one to six carbons. Specifically, the $C_{1-6}$ alkyl group includes, for example, a methyl group, an ethyl group, a 1-propyl group, a 2-propyl group, a 2-methyl-1-propyl group, a 2-methyl-2-propyl group, a 1-butyl group, a 2-butyl group, a 1-pentyl group, a 2-pentyl group, a 3-pentyl group, a 2-methyl-1-butyl group, a 3-methyl-1-butyl group, a 2-methyl-2-butyl group, a 3-methyl-2-butyl group, a 2,2-dimethyl-1-propyl group, a 1-hexyl group, a 2-hexyl group, a 3-hexyl group, a 2-methyl-1-pentyl group, a 3-methyl-1-pentyl group, a 4-methyl-1-pentyl group, a 2-methyl-2-pentyl group, a 3-methyl-2-pentyl group, a 4-methyl-2-pentyl group, a 2-methyl-3-pentyl group, a 3-methyl-3-pentyl group, a 2,3-dimethyl-1-butyl group, a 3,3-dimethyl-1-butyl group, a 2,2-dimethyl-1-butyl group, a 2-ethyl-1-butyl group, a 3,3-dimethyl-2-butyl group, and a 2,3-dimethyl-2-butyl group;

"heterocycle" or "heterocyclic group" refers to an aromatic or non-aromatic ring that may comprise double bonds within the ring, wherein at least one, for example one or two, of the atoms constituting the ring are heteroatoms;

"aromatic heterocycle" or "heteroaromatic ring" refers to a single aromatic cycle or ring that comprises a delocalized electronic structure wherein at least one, for example one or two, of the atoms constituting the ring are heteroatoms;

"nitrogen-containing heterocycle" or "heterocyclic group comprising one or more nitrogen atoms" refers to an aromatic or non-aromatic ring that may comprise double bonds within the ring, wherein at least one, for example one or two, of the atoms constituting the ring are nitrogen atoms;

"oxygen-containing heterocycle" or "heterocyclic group comprising one or more oxygen atoms" refers to an aromatic or non-aromatic ring that may comprise double bonds within the ring, wherein at least one, for example one or two, of the atoms constituting the ring are oxygen atoms;

"heteroatom" refers to a sulfur atom, an oxygen atom, or a nitrogen atom;

"nitrogen-containing 5- or 6-membered aromatic heterocycle" or "nitrogen-containing 5- or 6-membered heteroaromatic group" refers to a single aromatic ring in which five or six atoms constitute the ring, wherein at least one of the atoms constituting the ring is a nitrogen atom, and one or more heteroatoms other than nitrogen atoms may further be comprised. Specifically, the nitrogen-containing 5- or 6-membered aromatic heterocycle includes, for example, a pyrrole ring, a imidazole ring, a triazole ring, a diazole ring, a pyridine ring, a pyridazine ring, a pyrimidine ring, and a pyrazine ring;

"nitrogen-containing 5- or 6-membered heteroaryl group" refers to a mono- or divalent group derived by removing one or two arbitrary hydrogen atoms from the above-defined "5- or 6-membered aromatic heterocycle". Specifically, the nitrogen-containing 5- or 6-membered heteroaryl group includes, for example, a pyrrolyl group, an imidazolyl group, a diazolyl group, a triazolyl group, a pyridyl group, a pyridazinyl group, a pyrimidinyl group, and a pyrazinyl group;

"oxygen-containing 5- or 6-membered aromatic heterocycle" or "oxygen-containing 5- or 6-membered heteroaryl ring" refers to a single aromatic ring in which five or 6 atoms constitute the ring, wherein at least one of the atoms constituting the ring is an oxygen atom, and one or more heteroatoms other than oxygen atoms may further be comprised. Specifically, the oxygen-containing 5- or 6-membered aromatic heterocycle includes, for example, a furan ring or a pyran ring;

"oxygen-containing 5- or 6-membered heteroaryl group" refers to a mono- or divalent group derived by removing one or two arbitrary hydrogen atoms from the above-defined "oxygen-containing 5- or 6-membered aromatic heterocycle". Specifically, the "oxygen-containing 5- or 6-membered heteroaryl group" includes, for example, a furanyl group and a pyranyl group;

"Condensed aromatic heterocycle" refers to a ring structure in which an aromatic heterocyclic moiety is fused, for example ortho-condensed, with an aromatic ring, such as a benzene ring. The aromatic heterocyclic moiety may be an above-defined aromatic heterocycle;

"Condensed aromatic heterocyclic group" refers to a mono- or divalent group derived by removing one or two arbitrary hydrogen atoms from the above-defined "condensed aromatic heterocycle". The aromatic heterocyclic moiety is an above-defined heterocyclic group;

The condensed aromatic heterocyclic group includes, for example, an indolyl group, an indolinyl group, an isoindolyl group, an isoindolinyl group, a benzoxazolyl group, a benzimidazolyl group, a coumarinyl group, a quinolyl group, an isoquinolyl group and a 1,2,3,4-tetrahydroquinolinyl group;

"oxygen-containing 5- or 6-membered non-aromatic heterocycle" refers to a saturated carbon ring comprising one or more heteroatoms, for example a tetrahydrofuran ring, or a tetrahydropyran ring;

"oxygen-containing 5- or 6-membered non-aromatic heterocyclic group" refers to a mono- or divalent group derived by removing one or two arbitrary hydrogen atoms from the above-defined 4- to 8-membered heterocyclic ring. Specifically, "4- to 8-membered non-aromatic heterocyclic group" may refer to a tetrahydrofuranyl group, or a tetrahydropyranyl group; Herein, "halogenated $C_{1-6}$ alkyl group" refers to a group in which at least one arbitrary hydrogen atom in the above-defined "$C_{1-6}$ alkyl group" is replaced with an above-defined "halogen atom". The halogenated $C_{1-6}$ alkyl group includes, for example, a trifluoromethyl group, a difluoromethyl group, and a monofluoromethyl group.

Herein, the phrase "may have one or more substituent" means that a certain group or compound is in the first instance unsubstituted but that it may optionally have an arbitrary selection or combination of one or more substituent at substitutable positions. Specifically, the substituents can include, for example, atoms or groups selected from one or more of: halogen, hydroxyl, hydroxymethyl, hydroxyethyl, mercapto, nitro, cyano, formyl, carboxyl, trifluoromethyl, trifluoromethoxy, amino, oxo, imino, $C_{1-6}$ alkyl (for example methyl), $C_{1-6}$ alkoxy (for example, methoxy), $C_{1-6}$ thioalkyl (for example thiomethyl), $C_{2-6}$ alkenyl, $C_{2-6}$ alkynyl; $C_{1-6}$ alkoxycarbonyl, $C_{1-6}$ alkylsulfonyl, $C_{6-10}$ cycloalkyl, $C_{6-10}$ aryl, benzyl, heteroaryl (for example pyridyl), phenyl, or $C_{6-10}$ cycloalkyl, $C_{6-10}$ aryl or benzyl or phenyl or heteroaryl (for example pyridyl) substituted by one or more of halogen, hydroxyl, hydroxymethyl, hydroxyethyl, mercapto, nitro, cyano, formyl, carboxyl, trifluoromethyl, trifluoromethoxy, amino, oxo, imino, $C_{1-6}$ alkyl (for example methyl), $C_{1-6}$ thioalkyl (for example thiomethyl), $C_{2-6}$ alkenyl, $C_{2-6}$ alkynyl; $C_{1-6}$ alkoxycarbonyl, $C_{1-6}$ alkylsulfonyl, or $C_{1-6}$ alkoxy (for example, methoxy).

"$C_{2-6}$ alkenyl group" refers to a linear or branched alkenyl group comprising two to six carbons. Specifically, the $C_{2-6}$ alkenyl group includes, for example, a vinyl group, an allyl group, a 1-propenyl group, a 2-propenyl group, a 1-butenyl group, a 2-butenyl group, a 3-butenyl group, a pentenyl group, and a hexenyl group;

"$C_{2-6}$ alkynyl group" refers to a linear or branched alkynyl group comprising two to six carbons. Specifically, the $C_{2-6}$ alkynyl group includes, for example, an ethynyl group, a 1-propynyl group, a 2-propynyl group, a butynyl group, a pentynyl group, and a hexynyl group.

"$C_{1-6}$ alkoxy group" refers to an oxy group to which the above-defined "$C_{1-6}$ alkyl group" is linked. Specifically, the $C_{1-6}$ alkoxy group includes, for example, a methoxy group, an ethoxy group, a 1-propyloxy group, a 2-propyloxy group, a 2-methyl-1-propyloxy group, a 2-methyl-2-propyloxy group, a 1-butyloxy group, a 2-butyloxy group, a 1-pentyloxy group, a 2-pentyloxy group, a 3-pentyloxy group, a 2-methyl-1-butyloxy group, a 3-methyl-1-butyloxy group, a 2-methyl-2-butyloxy group, a 3-methyl-2-butyloxy group, a 2,2-dimethyl-1-propyloxy group, a 1-hexyloxy group, a 2-hexyloxy group, a 3-hexyloxy group, a 2-methyl-1-pentyloxy group, a 3-methyl-1-pentyloxy group, a 4-methyl-1-pentyloxy group, a 2-methyl-2-pentyloxy group, a 3-methyl-2-pentyloxy group, a 4-methyl-2-pentyloxy group, a 2-methyl-3-pentyloxy group, a 3-methyl-3-pentyloxy group, a 2,3-dimethyl-1-butyloxy group, a 3,3-dimethyl-1-butyloxy group, a 2,2-dimethyl-1-butyloxy group, a 2-ethyl-1-butyloxy group, a 3,3-dimethyl-2-butyloxy group, and a 2,3-dimethyl-2-butyloxy group;

"$C_{1-6}$ alkylthio group" refers to a thio group to which the above-defined "$C_{1-6}$ alkyl group" is linked. Specifically, the "$C_{1-6}$ alkylthio group" includes, for example, a methylthio group, an ethylthio group, a 1-propylthio group, a 2-propylthio group, a butylthio group, and a pentylthio group;

"$C_{1-6}$ alkoxycarbonyl group" refers to a carbonyl group to which the above-defined "$C_{1-6}$ alkoxy group" is linked. Specifically, the $C_{1-6}$ alkoxycarbonyl group includes, for example, a methoxy carbonyl group, an ethoxy carbonyl group, a 1-propyloxycarbonyl group, and a 2-propyloxycarbonyl group;

"$C_{1-6}$ alkylsulfonyl group" refers to a sulfonyl group to which the above-defined "$C_{1-6}$ alkyl group" is linked. Specifically, the $C_{1-6}$ alkylsulfonyl group includes, for example, a methylsulfonyl group, an ethylsulfonyl group, a 1-propylsulfonyl group, and a 2-propylsulfonyl group.

"halogen atom" refers to a fluorine atom, a chlorine atom, a bromine atom, or an iodine atom;

"$C_{6-10}$ cycloalkyl" refers to a non-aromatic cyclic hydrocarbon group comprising 6 to 10 carbon atoms. Specifically, the "$C_{6-10}$ cycloalkyl" group includes, for example, a cyclohexyl group, and a decalin group.

"$C_{6-10}$ aryl group" refers to an aromatic cyclic hydrocarbon group comprising six to ten carbon atoms. Specifically, the $C_{6-10}$ aryl group includes, for example, a phenyl group, a 1-naphthyl group, and a 2-naphthyl group;

"Salt" is not particularly limited, so long as it is a pharmaceutical acceptable salt which is formed with a compound according to the present invention. Such salts include, for example, inorganic acid salts, organic salts, inorganic base salts, organic base salts, and acidic or basic amino acid salts. Examples of preferable inorganic acid salts include: hydrochloride, hydrobromate, sulfate, nitrate, and phosphate. Examples of preferable organic salts include: acetate, succinate, fumarate, maleate, tartrate, citrate, lactate, stearate, benzoate, methanesulfonate, and p-toluene sulfonate.

Examples of preferable inorganic base salts include: alkali metal salts, such as sodium salts and potassium salts; alkali earth metal salts, such as calcium salts and magnesium salts; aluminium salts; and ammonium salts. Examples of preferable organic base salts include: diethylamine salts, diethanol amine salts, meglumine salts, and N,N'-dibenzylethylenediamine salts.

Examples of preferable acidic amino acid salts include: aspartate and glutamate. Examples of preferable basic amino acid salts include: arginine salts, lysine salts, and ornithine salts.

When left in air, the compounds of the present invention sometimes absorb moisture, and are sometimes attached to absorbed water or converted to hydrates. Such hydrates are also included in the present invention.

Furthermore, compounds of the present invention are sometimes converted into solvates, absorbing some other solvents. Such solvates are also included in the present invention.

Any organic solvent may in principle be used to prepare a solvate of the compounds of the present invention.

A solvate can include also water together with the one or more organic solvent.

Thus, for example, the solvent may be selected from ketones, alcohols, ethers, esters, aromatic solvents, and, where possible, mixtures thereof with each other, with other organic solvents and/or with water.

Pharmaceutically acceptable prodrug forms of the compounds of Formula (I) may be used in the present invention. "Pharmaceutically acceptable prodrugs" means those prodrugs of the compounds which are, within the scope of sound medical and vetinary judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds. The term "prodrug" means compounds that are rapidly transformed in vivo to yield the parent compound of the above Formula, for example by hydrolysis in blood. Functional groups which may be rapidly transformed, by metabolic cleavage, in vivo form a class of groups reactive with the carboxyl group. Because of the ease with which the metabolically cleavable groups of the compounds are cleaved in vivo, the compounds bearing such groups act as pro-drugs. A thorough discussion of prodrugs is provided in the following: Design of Prodrugs, H. Bundgaard, ed., Elsevier, 1985; Methods in Enzymology, K. Widder et al, Ed., Academic Press, 42, p. 309-396, 1985; A Textbook of Drug Design and Development, Krogsgaard-Larsen and H. Bundgaard, ed., Chapter 5; Design and Applications of Prodrugs p. 113-191, 1991; Advanced Drug Delivery Reviews, H. Bundgard, 8, p. 1-38, 1992; Journal of Pharmaceutical Sciences, 77, p. 285, 1988; Chem. Pharm. Bull., N. Nakeya et al, 32, p. 692, 1984; Pro-drugs as Novel Delivery Systems, T. Higuchi and V. Stella, Vol. 14 of the A. C. S. Symposium Series, and Bioreversible Carriers in Drug Design, Edward B. Roche, ed., American Pharmaceutical Association and Pergamon Press, 1987, which are incorporated herein by reference.

Compositions and Administration

The compound according to the present invention may be administered in the form of a composition comprising the active agent and any suitable additional component. The composition may, for example, be a pharmaceutical composition (medicament), suitably for topical administration (e.g. as eyedrops or cream or lotion), or enteral administration (e.g. as a tablet or capsule or drop) or parenteral administration (e.g. injection, implantation or infusion). The composition may alternatively, for example, be a foodstuff, food supplement, beverage or beverage supplement.

The term "pharmaceutical composition" or "medicament" in the context of this invention means a composition comprising an active agent and comprising additionally one or more pharmaceutically acceptable carriers. The composition may further contain ingredients selected from, for example, diluents, adjuvants, excipients, vehicles, preserving agents, fillers, disintegrating agents, wetting agents, emulsifying agents, suspending agents, sweetening agents, flavouring agents, perfuming agents, antibacterial agents, antifungal agents, lubricating agents and dispersing agents, depending on the nature of the mode of administration and dosage forms. The compositions may take the form, for example, of tablets, dragees, powders, elixirs, syrups, liquid preparations including suspensions, sprays, inhalants, tablets, lozenges, emulsions, solutions, cachets, granules, capsules and suppositories, as well as liquid preparations for injections, including liposome preparations. Techniques and formulations generally may be found in Remington, The Science and Practice of Pharmacy, Mack Publishing Co., Easton, Pa., latest edition.

Liquid form preparations include solutions, suspensions, and emulsions. As an example may be mentioned water or water-propylene glycol solutions for parenteral injection or topical administration. Liquid preparations can also be formulated in solution in aqueous polyethylene glycol solution.

Also included are solid form preparations which are intended to be converted, shortly before use, to liquid form preparations for either topical, oral or parenteral administration. Such liquid forms include solutions, suspensions, and emulsions. These particular solid form preparations are most conveniently provided in unit dose form and as such are used to provide a single liquid dosage unit. Alternately, sufficient solid may be provided so that after conversion to liquid form, multiple individual liquid doses may be obtained by measuring predetermined volumes of the liquid form preparation as with a syringe, teaspoon, or other volumetric container or apparatus. The solid form preparations intended to be converted to liquid form may contain, in addition to the active material, flavourings, colourants, stabilizers, buffers, artificial and natural sweeteners, dispersants, thickeners, solubilising agents, and the like. The liquid utilized for preparing the liquid form preparation may be water, isotonic water, ethanol, glycerine, propylene glycol, and the like as well as mixtures thereof. Naturally, the liquid utilized will be chosen with regard to the route of administration, for example, liquid preparations containing large amounts of ethanol are not suitable for topical or parenteral use.

The composition may be in a formulation intended for topical application. The formulation may be a gelling formulation to control release and therefore availability of the active agent following topical application. The formulation may contain one or more gelling agents, for example hydroxypropyl methylcellulose. The formulation may contain one or more surfactants, for example a non-ionic liquid polymer, examples of which include Tyloxapol, and the Pluronics® poloxamers from BASF. The formulation may contain one or more solubilizers, for example dextrose or sorbitol. The formulation may contain one or more anti-microbial or antiseptic agents, for example benzalkonium chloride. The aforementioned named gelling agents, surfactants, solubilizers and antimicrobial agents are listed purely by way of example and it will be appreciated that other agents to perform these functions are known.

The dosages may be varied depending upon the requirements of the patient, the severity of the condition being treated, and the compound being employed. Determination of the proper dosage for a particular situation is within the skill of the art. Generally, treatment is initiated with the smaller dosages which are less than the optimum dose of the compound. Thereafter the dosage is increased by small increments until the optimum effect under the circumstances is reached. For convenience, the total daily dosage may be divided and administered in portions during the day if desired.

The dosage regime for administration of the active agent may, for example, comprise a total dose of up to 1 µg, for example up to 500 ng, for example up to 50 ng, for example less than 20 ng of active agent in a dosing period ranging, for example, between 1 and 14 days. For example, a total dose of less than 18 ng, 17 ng, 16 ng, 15, ng, 14 ng, 13 ng, 12 ng, 11 ng or 10 ng may be administered.

The dosage regime for administration of the active agent may, for example, comprise a total dose of up to 10 µg, for example up to 5 mg, for example up to 500 ng, for example less than 200 ng of active agent in a dosing period ranging, for example, between 1 and 14 days. For example, a total dose of less than 180 ng, 170 ng, 160 ng, 150 ng, 140 ng, 130 ng, 120 ng, 110 ng or 100 ng may be administered.

The dosage regime for administration of the active agent may, for example, comprise a total dose of up to 10 mg, for example up to 5 mg, for example up to 500 µg, for example less than 200 µg of active agent in a dosing period ranging, for example, between 1 and 14 days. For example, a total dose of less than 180 µg, 170 µg, 160 µg, 150 µg, 140 µg, 130 µg, 120 µg, 110 µg or 100 µg may be administered.

The compound of Formula (I) or Formula (Ia) or a pharmaceutically acceptable salt, solvate, hydrate or prodrug thereof may be administered in a therapeutically effective amount. A therapeutically effective amount of a compound of Formula (I) or Formula (Ia) for topical administration for treatment of CNV may be at least about 5 µg/10 µl of delivery vehicle. Alternatively, a therapeutically effective amount may be at least about 100 µg/mL, for example at least about 200 µg/mL, at least about 300 µg/mL, at least about 400 µg/mL, at least about 500 µg/mL, at least about 600 µg/mL, at least about 700 µg/mL, at least about 800 µg/mL, at least about 900 µg/mL, or at least about 1000 µg/mL, Alternatively, a therapeutically effective amount may be at least about 1 mg/mL, for example at least about 2 mg/mL, at least about 3 mg/mL, at least about 4 mg/mL, at least about 5 mg/mL. Alternatively, a therapeutically effective amount may be less than about 5 mg/mL, for example less than about 4 mg/mL, less than about 3 mg/mL, less than about 2 mg/mL, less than about 1 mg/mL. The therapeutically effective amount may be administered daily, for a dosing period ranging, for example, between 1 and 14 days. The therapeutically effective amount may be a total daily dosage which may be divided and administered in portions during the day, for example twice daily.

A therapeutically effective amount of a compound of Formula (I) of Formula (Ia) for anti-angiogenic treatment of a mammalian subject, or for use in treating or preventing microvascular hyperpermeability disorders, or in regulating the pro-angiogenic pro-permeability properties of $VEGF_{xxx}$ isoforms, or in supporting epithelial cell survival without increased permeability, or in reducing the nature (for example the number density and/or size) of fenestrations of epithelial filtration membranes, or for use in treating or preventing neuropathic and neurodegenerative disorders, or for use as a neuroprotective or neuroregenerative agent in vivo or in vitro, or for use in treating or preventing VEGFR2-mediated non-inflammatory pain, or for use in preventing fibrosis may be calculated according to body mass of the subject to be treated, and may be at least about 20 mg/kg, for example at least about 30 mg/kg, at least about 40 mg/kg, at least about 50 mg/kg, at least about 60 mg/kg, at least about 70 mg/kg, at least about 80 mg/kg, at least about 90 mg/kg, at least about 100 mg/kg. Alternatively, the therapeutically effective amount may be less than about 100 mg/kg, for example less than about 90 mg/kg, less than about 80 mg/kg, less than about 70 mg/kg, less than about 60 mg/kg, less than about 50 mg/kg, less than about 40 mg/kg, less than about 30 mg/kg, or less than about 20 mg/kg, for example less than about 10 mg/kg, less than about 5 mg/kg.

"Treating or Preventing"

The expression "treating or preventing" and analogous terms used herein refers to all forms of healthcare intended to remove or avoid the disorder or to relieve its symptoms, including preventive, curative and palliative care, as judged according to any of the tests available according to the prevailing medical and psychiatric practice. An intervention that aims with reasonable expectation to achieve a particular result but does not always do so is included within the expression "treating or preventing". An intervention that succeeds in slowing or halting progression of a disorder is included within the expression "treating or preventing".

Certain neurological and psychiatric disorders are considered as "spectrum" conditions, in which individuals may exhibit some or all of a range of possible symptoms, or may exhibit only a mild form of the disorder. Furthermore, many neurological and psychiatric conditions are progressive, starting with relatively mildly abnormal symptoms and progressing to more severely abnormal symptoms. The present invention includes the treatment and prevention of all neurological and psychiatric conditions of whatever type and stage.

"Susceptible to"

The expression "susceptible to" and analogous terms used herein refers particularly to individuals at a higher than normal risk of developing a medical or psychiatric disorder, or a personality change, as assessed using the known risk factors for the individual or disorder. Such individuals may, for example, be categorised as having a substantial risk of developing one or more particular disorders or personality changes, to the extent that medication would be prescribed and/or special dietary, lifestyle or similar recommendations would be made to that individual.

"Non-Therapeutic Method"

The expression "non-therapeutic method" used herein refers particularly to an intervention performed on an individual who is neurologically or psychologically within the normal range, to normalise or enhance or improve a function of the neurological or psychological kind. A neurological function that may suitably be treated non-therapeutically may include, for example, cognition (including thinking, reasoning, memory, recall, imagining and learning), concentration and attention, particularly towards the milder end of the scale of conditions, and mild abnormal behavioural or personality traits. A psychological function that may suitably be treated non-therapeutically may include, for example, human behaviour, mood, personality and social function, for example grief, anxiety, depression, moodiness, moroseness, teenage moods, disrupted sleep patterns, vivid dreaming, nightmares, and sleepwalking.

There is a borderline between diagnosable neurological and psychiatric disorders and (non-diagnosable) neurological and psychological functions within the normal range. Therefore, in addition to the examples of neurological and psychological functions give above that are treatable according to the non-therapeutic methods of the present invention, mild forms of neurological and psychiatric disorders, that are non-diagnosable because the associated behaviours or thoughts do not cause significant distress to the individual or are not disruptive of his or her everyday functioning, are also to be considered as conditions treatable non-therapeutically according to the present invention.

"Normalise"

The expression "normalise" and analogous terms used herein refers particularly to a physiological adjustment towards a condition characteristic of general normal neurological or psychiatric health, whether or not a condition is actually reached that would be characterised as normal.

Mammals

Besides being useful for human treatment, the present invention is also useful in a range of mammals. Such mammals include non-human primates (e.g. apes, monkeys and lemurs), for example in zoos, companion animals such as cats or dogs, working and sporting animals such as dogs, horses and ponies, farm animals, for example pigs, sheep, goats, deer, oxen and cattle, and laboratory animals such as rodents (e.g. rabbits, rats, mice, hamsters, gerbils or guinea pigs).

Where the disorder or function to be treated is exclusive to humans, then it will be understood that the mammal to be treated is a human. The same applies respectively to any other mammalian species if the disorder or function to be treated is exclusive to that species.

BRIEF DESCRIPTION OF THE DRAWINGS

Embodiments of the present invention will now be described, purely by way of example, and with reference to the accompanying drawings, in which.

METHODS

Synthetic Protocol

Figure 1:
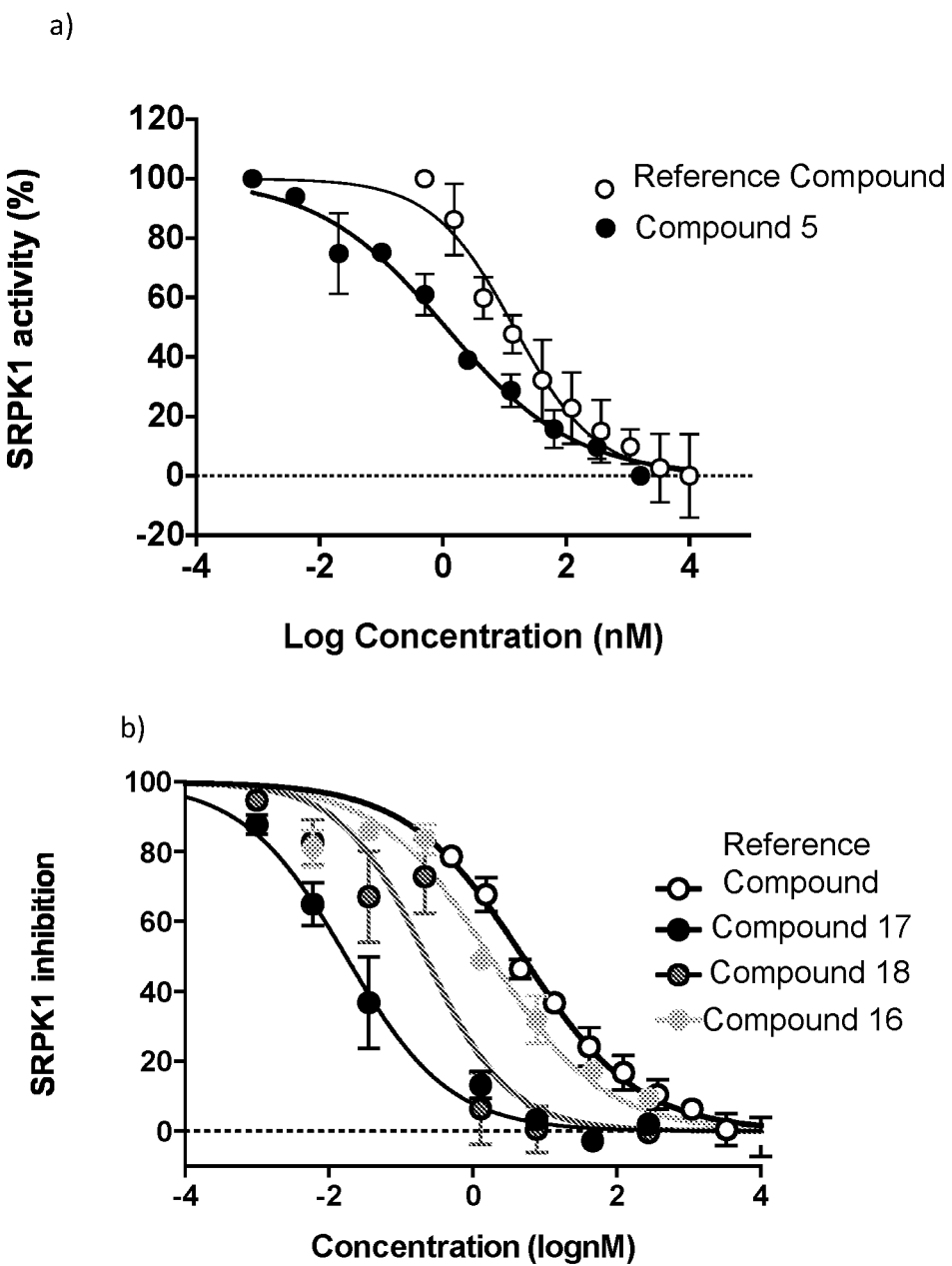
FIG. 1a shows the activity of compound 5 against SRPK1 compared with a reference compound and FIG. 1b shows the activity of compounds 16-18 relative to the same reference compound.

The general synthetic protocol for compounds is shown in Scheme 1 and described in detail below, in which $R_1$, $R_2$ and $R_3$ are as defined herein. Variations of this protocol to synthesize other compounds described herein are within the wherewithal of the skilled person.

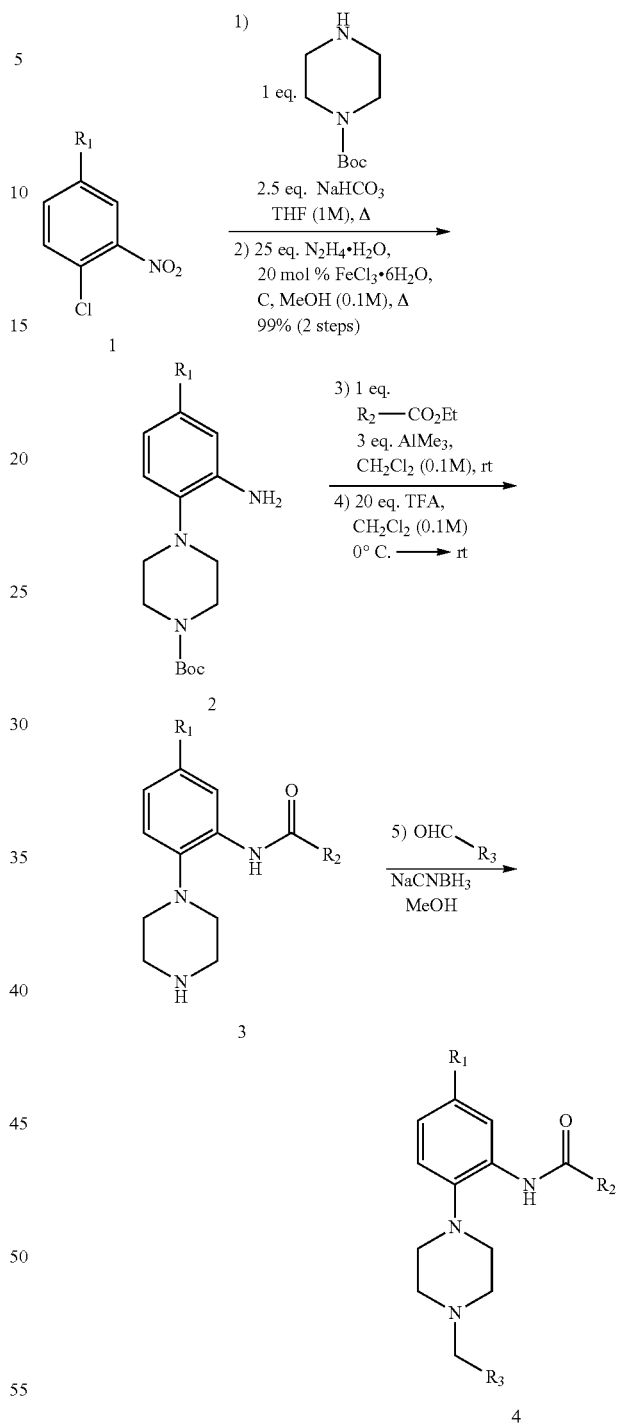

Synthesis of Anilines 2

A solution of Boc-piperazine (1 equiv.), compound 1 (1 equiv.) ($R_1$ is as defined elsewhere) and sodium bicarbonate (2.5 equiv.) in THF (1 M) was heated at reflux for 16 h. The solution was allowed to cool to room temperature and the reaction solution was filtered through a short pad of Celite, eluting with ethyl acetate. The solvent was removed under reduced pressure to afford a Boc-protected nitro compound, which was of sufficient purity to use in the next step.

Hydrazine hydrate (25 equiv.) was added dropwise to a suspension of Boc-protected nitro compound (1 equiv.), iron (III) chloride hexahydrate (20 mol %) and activated carbon (20% wt./wt.) in methanol (0.1 M) at room temperature. The solution was heated at reflux for 2 h. The solution was allowed to cool to room temperature then filtered through a short pad of Celite, eluting with ethyl acetate. The solvent was removed under reduced pressure. The residue was diluted with water and extracted with ethyl acetate (×3). The organic extracts were combined and dried ($Na_2SO_4$). The solvent was removed under reduced pressure to afford the product as a white solid, which was of sufficient purity to use in the next step.

Synthesis of Aromatic Piperazines 3

A solution of trimethylaluminium in toluene (2 M, 3 equiv.) was added dropwise to a solution of aniline 2 (1 equiv.) in dichloromethane (0.5 M) at room temperature. The solution was stirred at room temperature for 1 h after which, a solution of ethyl ester ($R_2$ is as defined elsewhere) (1 equiv.) in dichloromethane (1 M) was added dropwise at room temperature. The reaction solution was stirred at room temperature for an additional 16 h. To quench the reaction saturated aqueous Rochelle's salt solution was added dropwise at room temperature and the solution allowed to stir at room temperature for a further 15 minutes. The mixture was diluted with saturated aqueous sodium bicarbonate solution and extracted with dichloromethane (×3). The organic extracts were combined and washed with water and brine, then dried ($Na_2SO_4$). The solvent was removed under reduced pressure and the crude material was purified by flash chromatography on deactivated silica gel to afford the product.

For compound 37: Acetyl chloride (1.5 equiv.) was added dropwise to a solution of aniline (1 equiv.) in 1,2-dimethoxyethane (0.3 M) at 0° C. The solution was stirred at this temperature for 15 min then, the cold bath was removed and the solution was allowed to warm to room temperature before being heated at reflux for 17 hours. The reaction solution was cooled to room temperature and the solvent was removed under reduced pressure. The residue was dissolved in dichloromethane and washed with saturated aqueous sodium bicarbonate solution, water and brine, then dried ($Na_2SO_4$). The solvent was removed under reduced pressure. The crude product was purified by flash chromatography on deactivated silica gel, eluting with 20% ethyl acetate/n-hexane, to afford the product.

TFA (20 equiv) was added, at 0° C., to a 0.15 M solution of the resulting Boc-protected piperazine (1 equiv.) in $CH_2Cl_2$. The reaction mixture was allowed to warm to ambient temperature over 4 h. The reaction was quenched with saturated aqueous $NaHCO_3$ solution and the resultant aqueous layer was extracted with $CH_2Cl_2$ (×3) and the combined organic extracts were dried ($Na_2SO_4$) and concentrated to yield the title compound 3. The compound was used in the next step without further purification.

General Procedure for the Syntheses of Compound 4

Piperazine 3 (1 equiv.) and sodium cyanoborohydride (2 equiv.) were added successively as solids to a 0.1M solution of the $R_3$ aldehyde ($R_3$ as defined elsewhere) (1 equiv.) in methanol. The solution was allowed to stir at room temperature for 40 h. The solvent was removed under reduced pressure. The residue was diluted with saturated aqueous sodium bicarbonate solution and extracted with dichloromethane (×3). The organic extracts were combined and washed with brine, then dried ($Na_2SO_4$). The solvent was removed under reduced pressure. The crude product was purified by flash chromatography on deactivated silica gel, eluting with 2-5% methanol/ethyl acetate, to afford the product.

Analytical data for all compounds is presented in Table 3.

In vitro Kinase Assay

Candidate compounds were tested for SRPK1 inhibition using a Kinase-Glo assay (Promega, Southampton, UK32). A reaction buffer containing 40 mM Tris-HCl pH of 7.5 and 20 mM $MgCl_2$ was added to 86.5 µM SRSF1Arg-Ser (RS) peptide ($NH_2$-RSPSYGRSRSRSRSRSRSRSRSNSRSRSY-OH) (SEQ ID NO:1) and 0.1 µg of purified SRPK1 kinase. Candidate compounds were serially diluted from 10 µM to 0.5 nM and added to the reaction mixture, wells with omitted SRPK1 kinase and omitted compounds were also added as controls. All wells contained 1% DMSO (Fisher Scientific, Loughborough, UK). One micromolar ATP was added, wells minus ATP were used as background controls. The plate was then incubated at 30° C. for 10 minutes. An equal volume of Kinase-Glo (25 µL; Promega) was added to each well and the plate read for luminescence using a Fluostar Optima (BMG Labtech).

In vivo Angiogenesis Assay: Laser-Induced Choroidal Neovascularisation (CNV) Protocol 6-8 week-old female C57/B6 mice were anesthetized with an intraperitoneal injection of a mixture of 50 mg/kg ketamine and 0.5 mg/kg medetomidine. The pupils were immediately dilated by topical (eyedrop) application with a dilator such as 5% phenylephrine hydrochloride and 1% tropicamide. Four photocoagulation lesions were delivered with a green Merilas 532a laser (450 mW, 130 ms) between the "large" retinal vessels in clear space with no vessels in a peripapillary distribution at a distance of 1-2 disc-diameters in each eye. Only clean laser lesions with a subretinal bubble at the time of treatment were included in the study. Immediately following laser photocoagulation the animals were given topical eye drops of candidate compounds twice daily (10 µl, eyes held for 30 seconds to prevent animal wiping drop away).

After one week, mice were anesthetized with an intraperitoneal injection of a mixture of 50 mg/kg ketamine and 0.5 mg/kg medetomidine. The pupils were immediately dilated by topical (eyedrop) application with a dilator such as 5% phenylephrine hydrochloride and 1% tropicamide. Mice were administered an intraperitoneal injection of sodium fluorescein (10%). Phase contrast and green fluorescent fundus images were taken with an angiography microscope and camera with each lesion in focus. The mice were killed by a schedule 1 method and eyes were either unfixed for retinal dissection and protein extraction, or fixed and enucleated and choroids stained and examined.

Differential Scanning Fluorimetry

Figure 10:
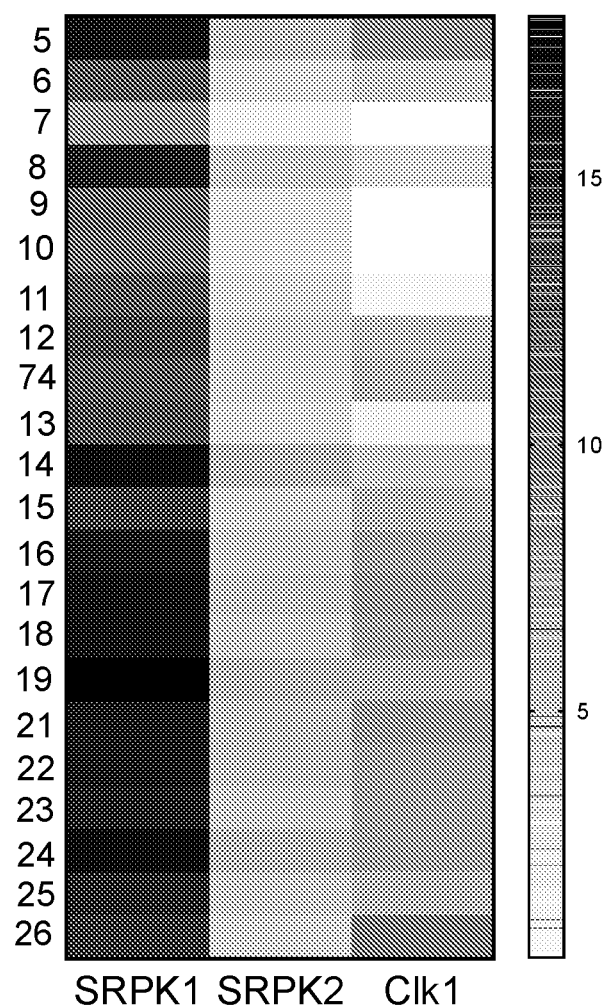
FIG. 10 shows the specificity of selected compounds for SRPK1 as determined using differential scanning fluorimetry.

Differential Scanning Fluorimetry was performed as described in Federov et al (2011). The values for $\Delta Tm$ (° C.) in the plot shown in FIG. 10 demonstrate the specificity of these compounds for SPRK1 over other kinases.

Conventional PCR and qRT-PCR.

Conventional RT-PCR

Primary human retinal epithelial cells were lysed in Trizol reagent and mRNA was extracted using the method of Chomczynski and Sacchi, or using an RNeasy RNA extraction kit (Qiagen, UK). mRNA was reverse transcribed using Thermoscript reverse transcriptase (Fisher Scientific, UK). The cDNA was amplified using primers designed to amplify the region spanning the proximal and distal splice sites in human VEGF-$A_{165}$a and VEGF-$A_{165}$b, to amplify both isoforms and differentiate between them due to the fact that the exon 8b-containing isoform is 66-bp shorter than the exon 8a-containing isoform. The primers used were; 5'-AAGGCGAGGCAGCTTGAGTTA-3' (SEQ ID NO:2) and 5'-TCTGTATCAGTCTTTCCTGGTGAGAG-3' (SEQ ID NO:3) with the following conditions; 96° C. for 2 min followed by 45 cycles at 96° C.-30 s, 60° C.-30 s and 72° C.-30 s. The PCR mix consisted of DNA: 200 ng, MgCl2 0.25 mM, Primer each 1 nM, Taq polymerase 1 unit and $dH_2O$ up to 25 µl. Control plasmid concentration: VEGF$_{165}$a 500 ng and VEGF$_{165}$b 1 µg. PCR products were run on 3% agarose gels containing 0.5 µg/ml ethidium bromide.

RT-qPCR to Amplify Human VEGF-$A_{165}$a and VEGF-$A_{165}$b

RNA was isolated and reverse transcribed as described above. Quantitative PCR (qPCR) was performed with a LightCycler 480 (Roche) q-PCR machine. The qPCR mix included PCR-grade $dH_2O$ 3 PCR Primer (1 μM) 2 μl. Taq-Man Master Mix, 2× conc 10 μl, cDNA 5 μl (from 20 ng/μl) MgCl2 concentration was 0.25 mM, The primers used were Forward: 5'-GAGCAAGACAAGAAAATCCC-3' (SEQ ID NO:4) and $VEGF_{165}$a-R-5'-CCTCGGCTTGTCA-CATCTG-3' (SEQ ID NO:5), $VEGF_{165}$b-R-5'-GTGAGA-GATCTGCAAGTACG-3' (SEQ ID NO:6). qPCR cycle was 95° C. for 4 min followed by 40 cycles at 95° C.-30 s 60° C.-30 s and 72° C.-30 s.

VEGF ELISA with $VEGF_{165}$a and $VEGF_{165}$b Capture Antibodies 96-well clear microplate (high sensitivity thermo immulon or costar 9018) were coated with 100 μL of 10 μg/ml $VEGF_{xxx}$b or 0.25 μg/ml anti-$hVEGF_{165}$a per well. The plate was sealed with parafilm and incubated overnight on the shaker at room temp. Each well was aspirated and washed with Wash Buffer (200 μl PBS-Tween 0.05%), two times for a total of three washes. After the last wash, remaining Wash Buffer was removed by inverting the plate and blotting it against clean paper towels. Plates were blocked by adding 100 μl of Reagent Diluent (1% BSA/PBS) to each well and incubated at room temp on a shaker for 2 hours. The aspiration/wash step was repeated. 100 μL of standards or samples in 1% BSA/PBS were added to each well, covered with parafilm and incubated 2 hours at room temperature. The aspiration/wash was repeated and 100 μL of 100 ng/ml Detection Antibody (BAF293), diluted in Reagent Diluent, was added to each well which were covered with parafilm and incubated 2 hours at room temp. The aspiration/wash was repeated and 100 μL of the working dilution of Streptavidin-HRP (1:200 dilution) was added to each well. The plate was covered and incubated for 30 minutes at room temperature. The plate was washed and 100 μL of Substrate Solution (1:1 of A:B from DY999) added to each well and incubated for 20-60 minutes at room temperature. 50 μL of Stop Solution (1M Hcl) was added to each well. The optical density of each well was measured immediately, using a microplate reader set to 450 nm.

Results

SRPK1 Inhibition

Figure 2:
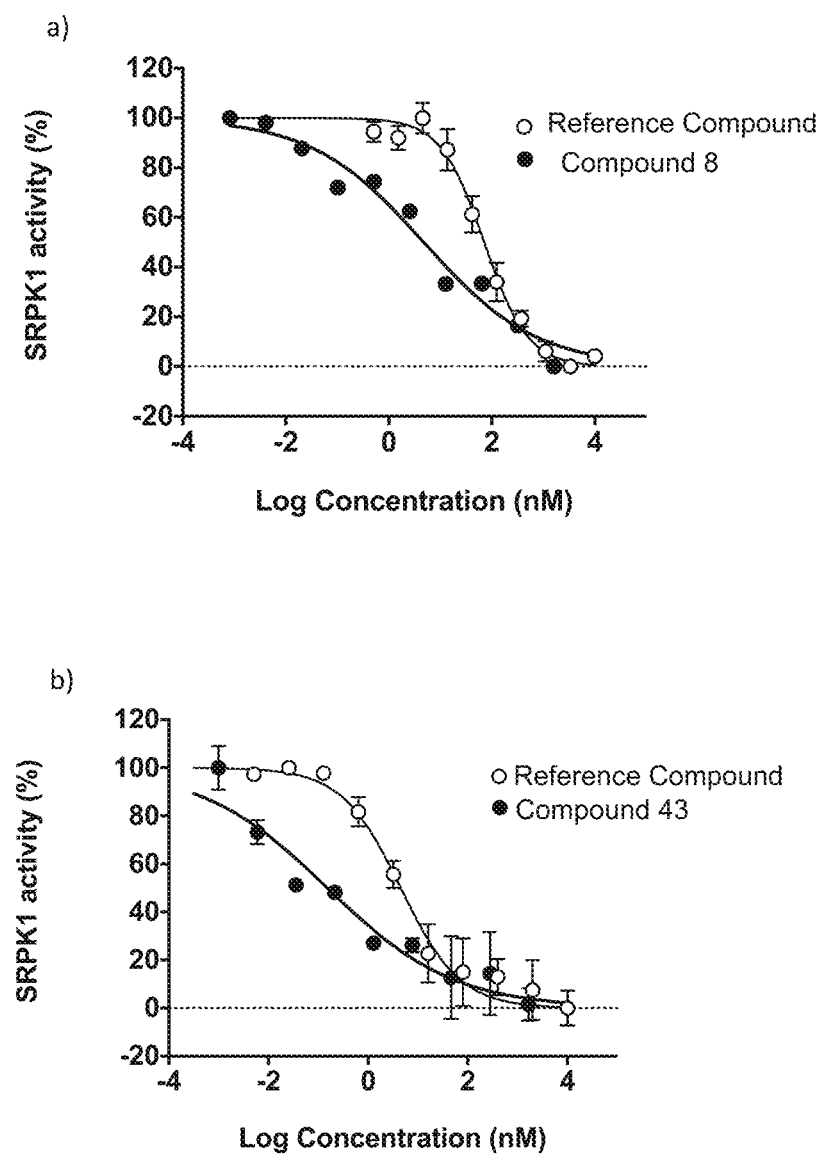
FIG. 2 shows the activity of compounds 8 and 43 against SRPK1 compared with reference compounds.

Screening of a series of molecules identified compounds (Compounds 5, 8, 16 to 18 and 43 of Table 3) that had improved potency against SRPK1 against a series of analogous compounds in which the $R_3$ group of the respective compounds of the present invention (as defined by Formula I) was replaced with a pyridyl ring (FIGS. 1 and 2, in which the reference compounds had an $IC_{50}$ of 6.00 nM and a ΔTm of 12.8° C. (FIG. 1); an $IC_{50}$ of 38.8 nM (FIG. 2a) and an $IC_{50}$ of 3.8 nM (FIG. 2b)) as determined by kinase assay or differential scanning fluorimetry (temperature difference, ΔTm is inversely proportional to the log Kd, i.e. an increased temperature difference indicates a higher affinity and therefore a more potent inhibitor). These included furan, oxazole, pyrazole, thiazole, methyl-pyrazole, and oxadiazole moieties. Replacement of the pyridine ring of indolyl compound 38 in Table 3 with a furan ring resulted in a drop in potency (23.9 nM for compound 38 vs. 65 nM for the resulting furan analogue).

With the discovery of the improved potency, it was decided to examine the scope of this type of substitution. As a consequence, we generated a library of 5-membered heteroaryl analogs and this data is presented in Tables 1 and 2. As can be seen from this data, some extremely potent molecules were generated, with N-(2-(4-(oxazol-2-ylmethyl)piperazin-1-yl)-5-(trifluoromethyl)phenyl)-5-(pyridin-4-yl)furan-2-carboxamide, N-(2-(4-(oxazol-4-ylmethyl) piperazin-1-yl)-5-(trifluoromethyl)phenyl)-5-(pyridin-4-yl) furan-2-carboxamide and N-(2-(4-(oxazol-5-ylmethyl) piperazin-1-yl)-5-(trifluoromethyl)phenyl)-5-(pyridin-4-yl) furan-2-carboxamide (compounds 16 to 18 respectively) being sub-nanomolar in their activity against SRPK1.

5-Membered Heteroaryl Compounds Switch Expression to the Anti-Angiogenic Isoforms.

Figure 3:
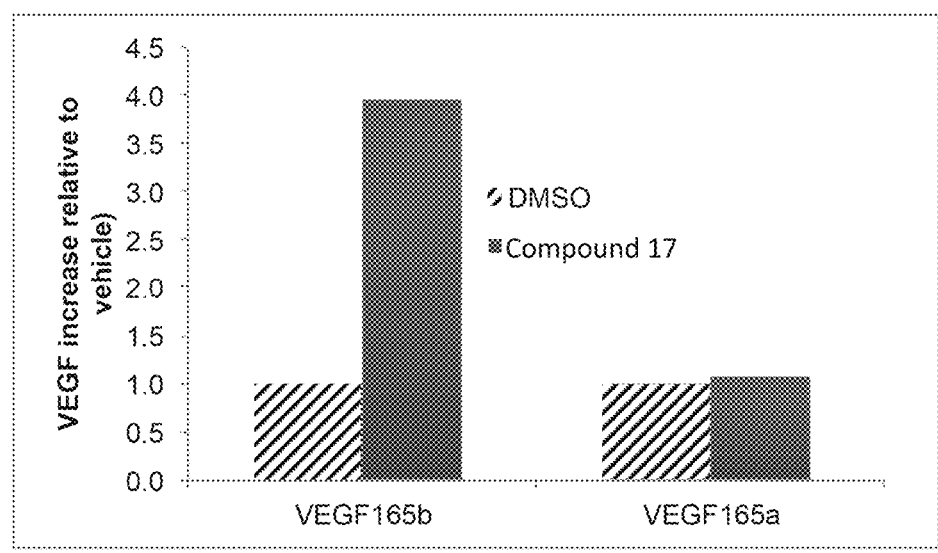
FIG. 3 shows the effect of compound 17 on splicing between different VEGF isoforms in retinal pigmented epithelial cells relative to a DMSO control.
Figure 4:
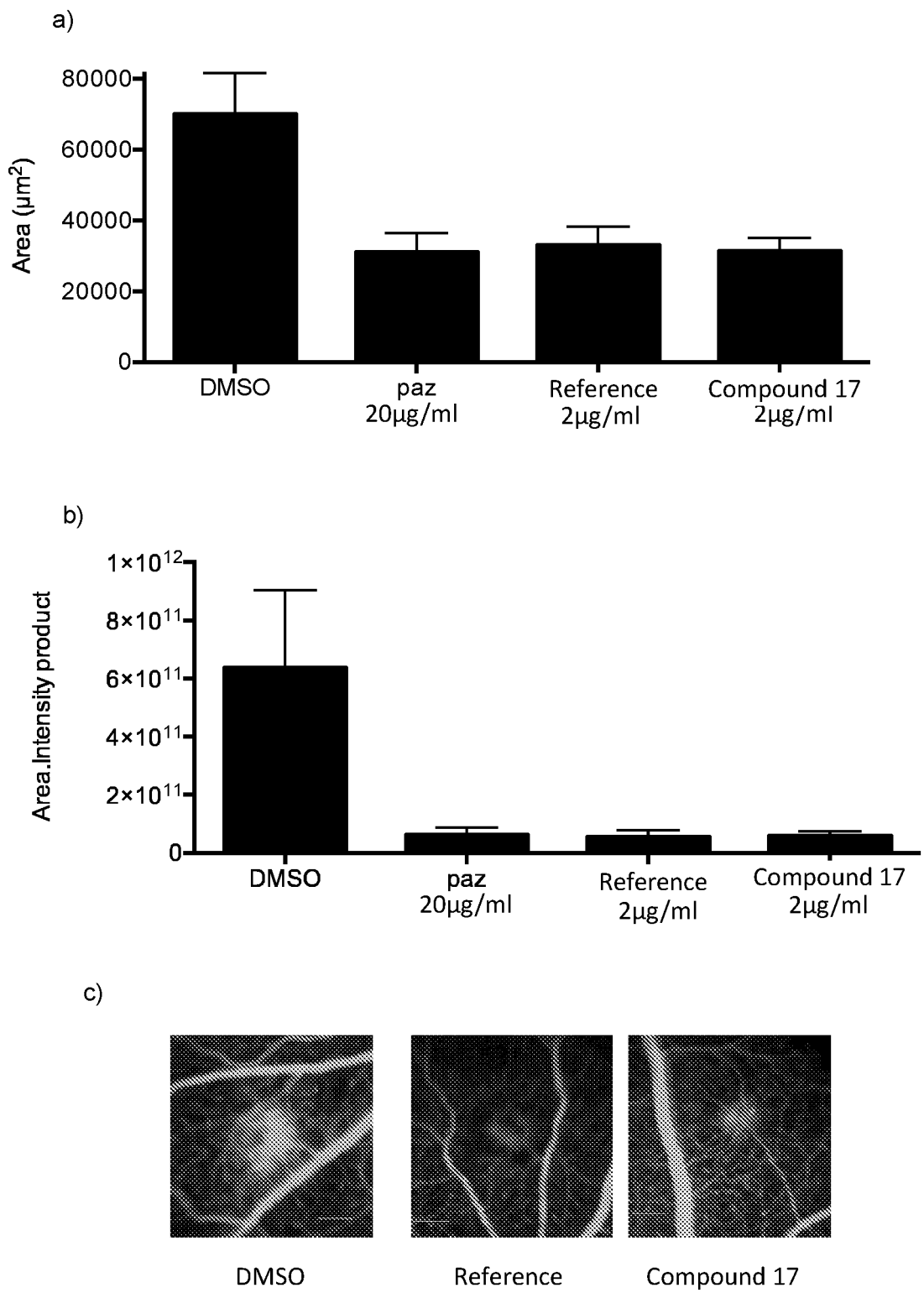
FIGS. 4a and b shows that compound 17 has the same anti-angiogenic activity on lesion size and the same efficacy as reference compounds in a laser-induced mouse model of CNV.
FIG. 4c shows fluorescein angiography images demonstrating that compound 17 has the same anti-angiogenic activity on lesion size as reference compounds in the laser-induced mouse model of CNV.
Figure 5:
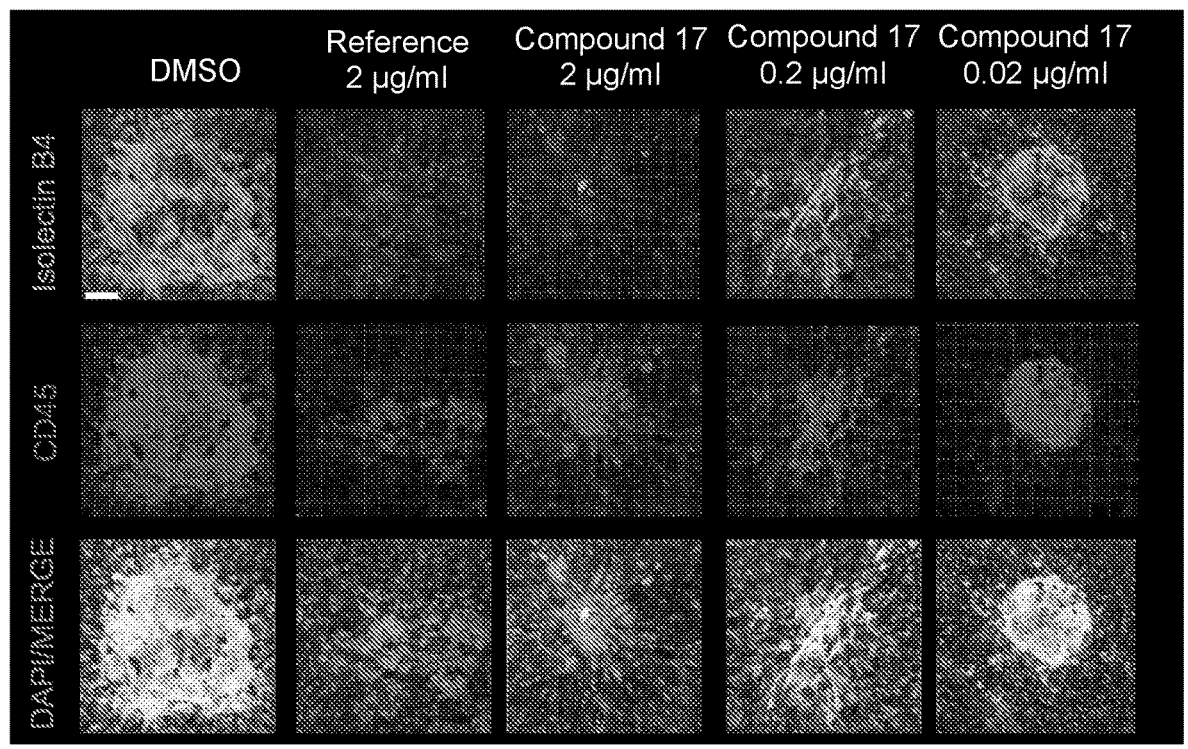
FIG. 5 shows the results of bidaily eye drops of compound 17 for 14 days on lased induced CNV lesion growth, visualised with isolectin B4 (top row); CD45 (middle row) and DAPI (bottom row), relative to a reference compound.
Figure 6:
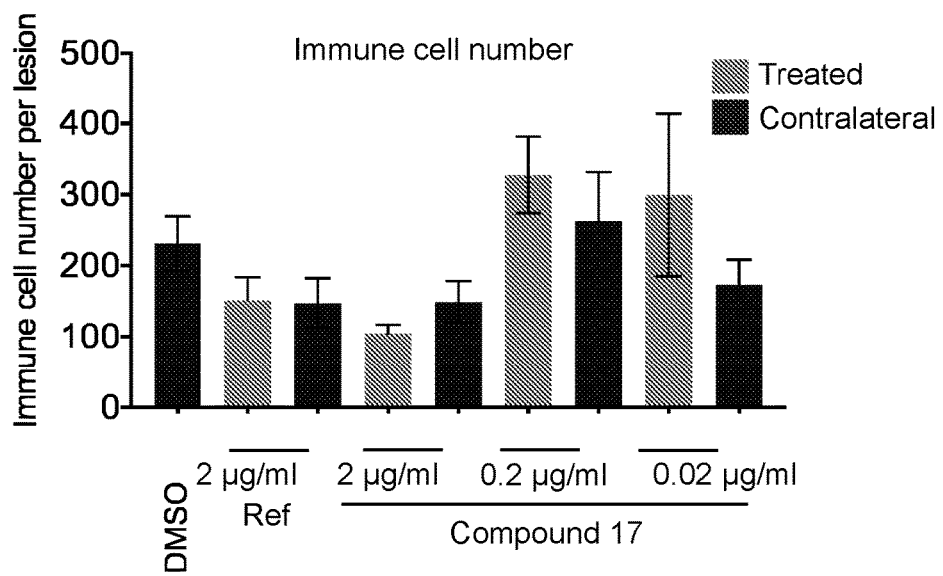
FIG. 6 shows the effect of compound 17 on immune cell recruitment relative to a reference compound in the same 14 day treatment protocol as for FIG. 5.
Figure 7A:
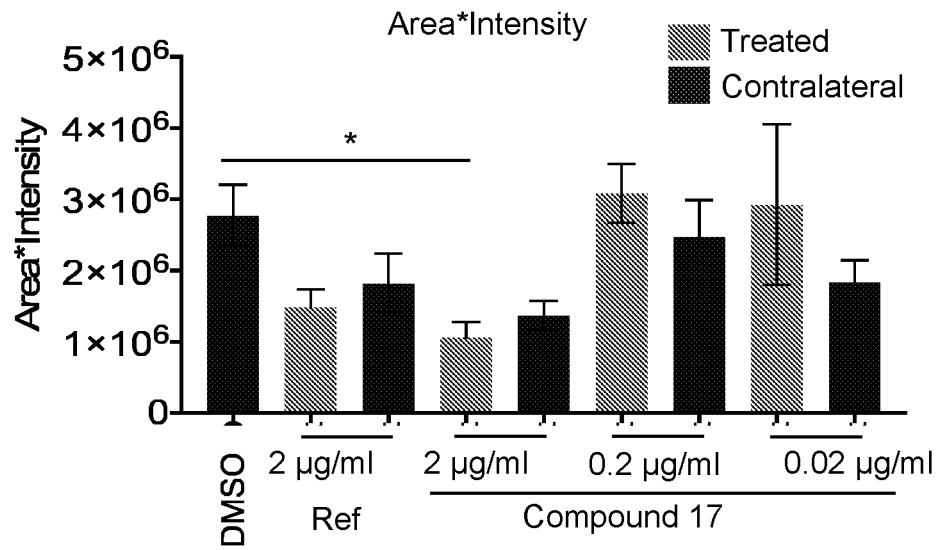
FIGS. 7a and 7b show the quantification of the isolectin B4 staining area intensity from the same 14 day treatment protocol as for FIG. 5.
Figure 7B:
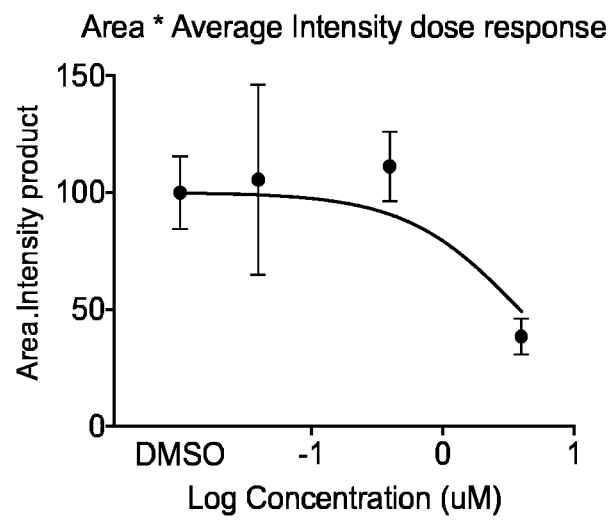

To determine whether these compounds could switch splicing of VEGF isoforms, VEGF was measured in retinal pigmented epithelial cells by isoform specific ELISA. FIG. 3 shows that treatment with N-(2-(4-(oxazol-4-ylmethyl) piperazin-1-yl)-5-(trifluoromethyl)phenyl)-5-(pyridin-4-yl) furan-2-carboxamide (compound 17) resulted in an increase in $VEGF_{165}$b, but not $VEGF_{165}$ protein.

Figure 8:
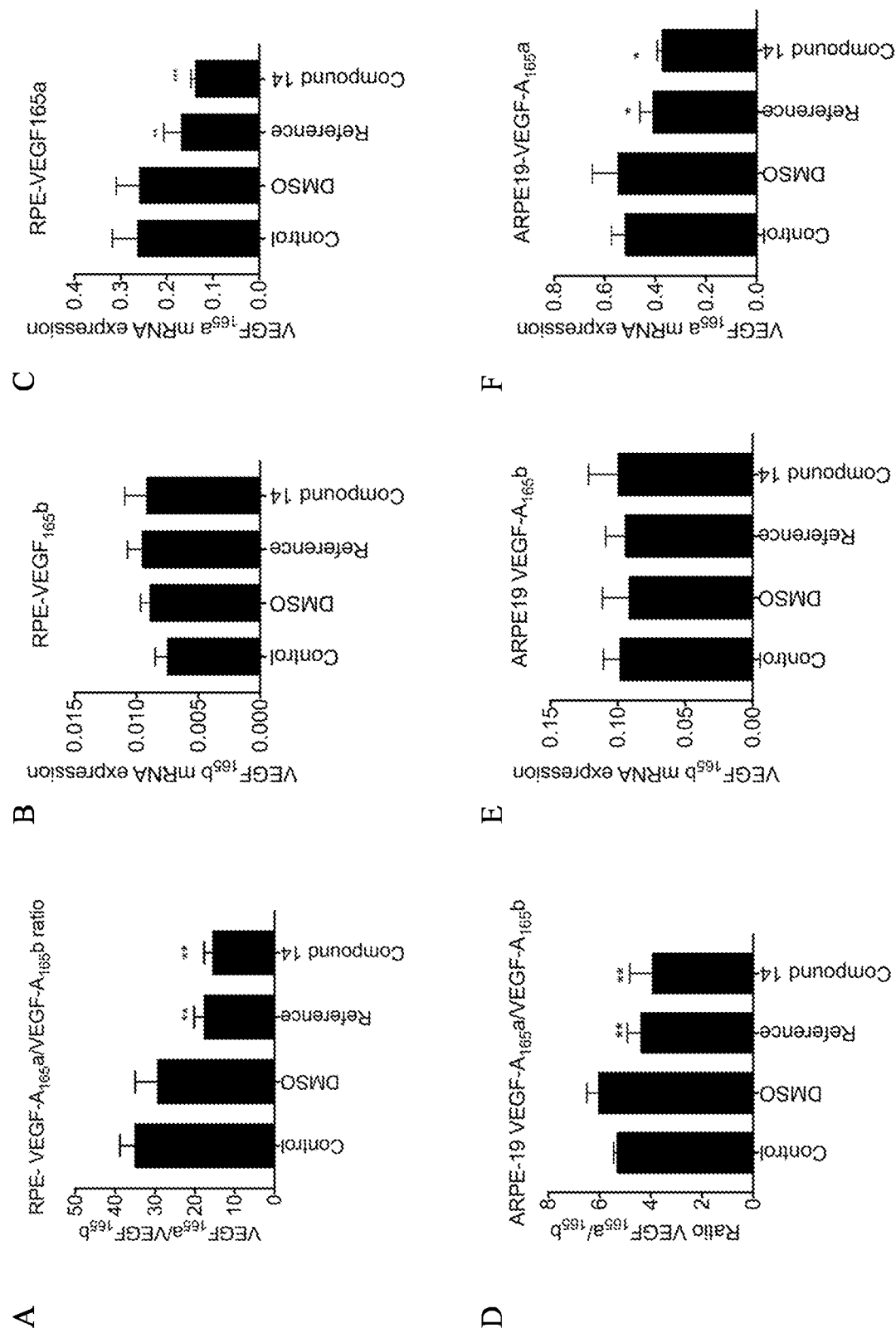
FIGS. 8 and 9 show that compound 14 switches alternative splicing to decrease VEGF-$A_{165}$a/VEGF$_{165}$b mRNA isoform expression in endothelial cells.
Figure 9:
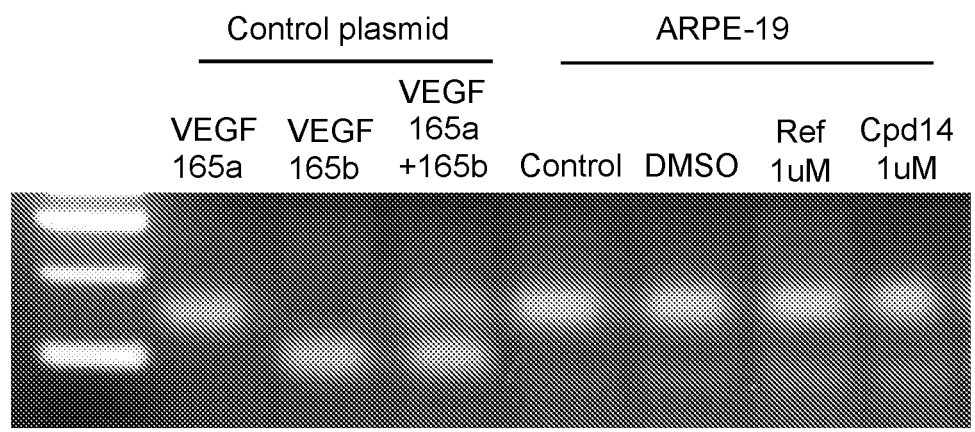

VEGF-A alternative splicing was further measured in retinal pigmented epithelial cells by qRT-PCR and conventional PCR. FIGS. 8 and 9 show that treatment with compound 14 switched the levels of $VEGF_{165}$b relative to $VEGF_{165}$ RNA by a decrease in $VEGF_{165}$ in primary RPE cells and ARPE-19 cells.

Figure 11:
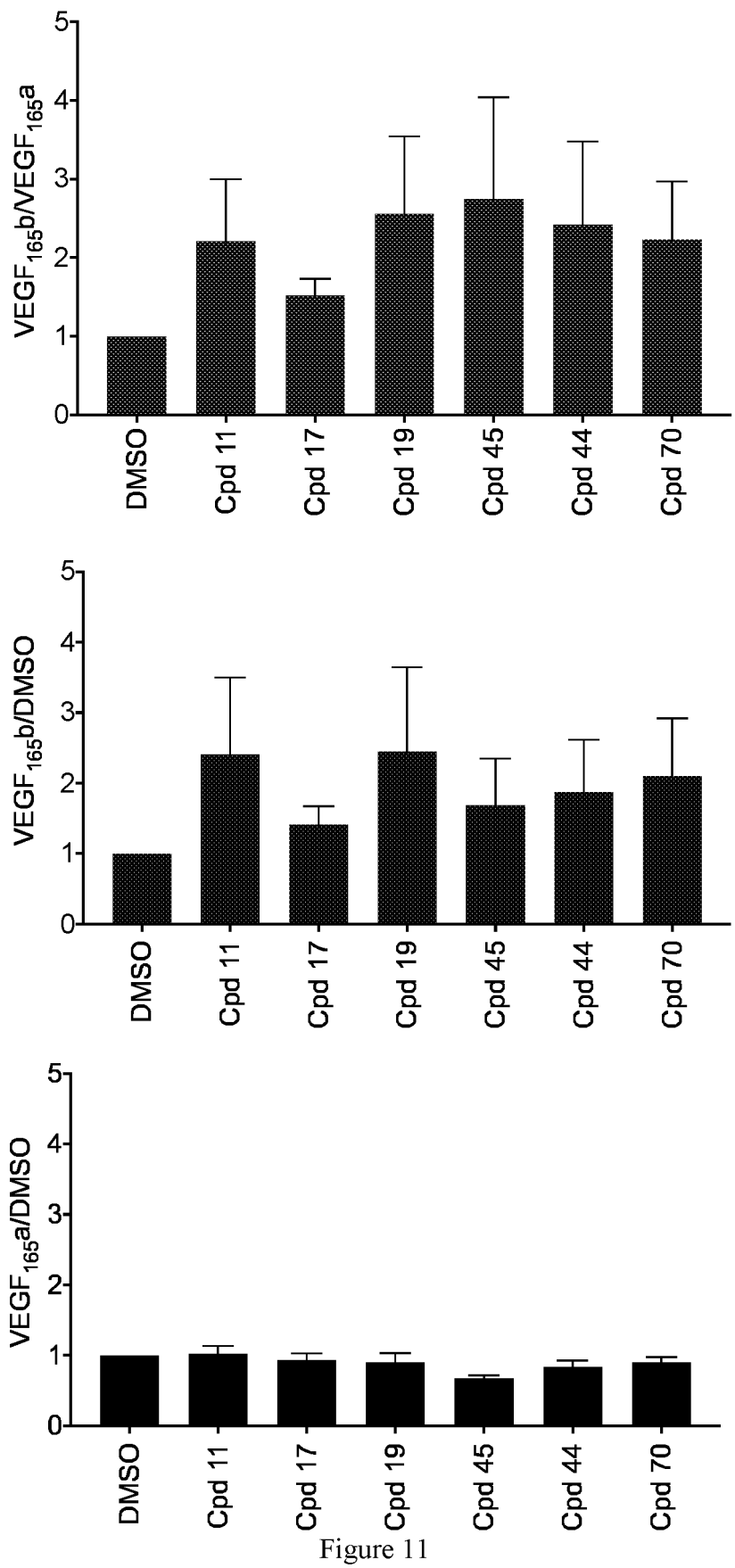
FIG. 11 shows that compounds of the present invention increase VEGF-$A_{165}$b/VEGF-$A_{165}$a protein ratio in PC-3 cells.

FIG. 11 shows examples of other 5-membered heteroaryl compounds that also switch VEGF-A isoform expression at the protein level by isoform specific ELISA in PC-3 cells.

Anti-Angiogenic Activity

We therefore tested the effect of N-(2-(4-(oxazol-4-ylmethyl)piperazin-1-yl)-5-(trifluoromethyl)phenyl)-5-(pyridin-4-yl)furan-2-carboxamide as an eye drop in an angiogenic model of wet age related macular degeneration in mice. N-(2-(4-(oxazol-4-ylmethyl)piperazin-1-yl)-5-(trifluoromethyl)phenyl)-5-(pyridin-4-yl)furan-2-carboxamide was compared in a dose response trial against the analogue compound in which $R_3$ is a pyridyl group ($IC_{50}$ for SRPK1 6 nM). N-(2-(4-(oxazol-4-ylmethyl)piperazin-1-yl)-5-(trifluoromethyl)phenyl)-5-(pyridin-4-yl)furan-2-carboxamide had the same efficacy as an eye drop compared with the lowest dose at which the reference compound was effective (2 μg/ml) (FIG. 4-7), which is a factor of 10 more effective than the known pazopanib-based eye drop treatment for AMD.

The data presented here shows small molecular weight compound inhibitors for reducing pro-angiogenic VEGF mediated CNV associated with AMD. Furthermore we have shown that the compounds of the present invention penetrate into the back of the eye, are effective at reducing CNV following topical administration in mice, and are safe on tests undertaken so far.

TABLE 1

$IC_{50}$ data for compounds of Formula (I) tested in the SRPK1 inhibition assay

| Compound | $IC_{50}$ (nM) |
| --- | --- |
| 5 | 0.37 |
| 6 | 88.3 |
| 7 | 337.3 |
| 8 | 17.6 |
| 9 | 62.4 |
| 10 | 191.2 |
| 11 | 79.8 |
| 12 | 158.5 |
| 13 | 39.5 |
| 14 | 3.5 |
| 15 | 21.4 |
| 16 | 4.6 |
| 17 | 1.3 |
| 18 | 0.76 |
| 19 | 1.7 |
| 20 | 104.2 |

TABLE 1-continued

IC$_{50}$ data for compounds of Formula (I) tested in the SRPK1 inhibition assay

| Compound | IC$_{50}$ (nM) |
|---|---|
| 21 | 175.6 |
| 22 | 13.7 |
| 23 | 27.5 |
| 24 | 10.9 |
| 25 | 11.3 |
| 26 | 1.2 |
| 27 | 8.2 |
| 28 | 1.4 |
| 29 | 27.3 |
| 30 | 14.1 |
| 31 | 6.7 |
| 32 | 0.5 |
| 33 | 12.7 |
| 34 | 27.0 |
| 35 | 387.7 |
| 36 | 21.6 |
| 38 | 31.3 |
| 39 | 60.7 |
| 40 | 145.1 |
| 41 | 28.7 |
| 42 | 1258.9 |
| 43 | 0.7 |
| 44 | 3.7 |
| 45 | 1.8 |
| 46 | 10.7 |
| 47 | 21.95 |
| 48 | 32.6 |
| 49 | 117.2 |
| 50 | 561.0 |
| 51 | 21.0 |
| 52 | 162.2 |
| 53 | 83.1 |
| 54 | 344.3 |
| 55 | 1836.5 |
| 56 | 134.3 |
| 57 | 116.8 |
| 58 | 103.6 |
| 59 | 973.9 |
| 60 | 223.1 |
| 61 | 75.9 |
| 62 | 2.8 |
| 63 | 317.3 |
| 64 | 5.5 |
| 65 | 9.7 |
| 66 | 33.5 |
| 67 | 8.8 |
| 68 | 35.3 |
| 69 | 1.8 |
| 70 | 0.5 |
| 71 | 717.8 |
| 72 | 5.3 |
| 73 | 28.7 |
| 74 | 164.4 |
| 75 | 74.9 |

TABLE 2

DSF data for compounds of Formula (I) tested

| Compound | DSF (ΔTm/° C.) |
|---|---|
| 5 | 16.98 |
| 6 | 12.91 |
| 7 | 8.84 |
| 8 | 15.95 |
| 9 | 11.64 |
| 10 | 10.87 |
| 11 | 12.94 |
| 12 | 13.96 |
| 13 | 12.99 |
| 14 | 17.36 |
| 15 | 14.1 |
| 16 | 16.48 |
| 17 | 17.07 |
| 18 | 16.86 |
| 19 | 18.03 |
| 21 | 16.3 |
| 22 | 16.67 |
| 23 | 16.13 |
| 24 | 17.16 |
| 25 | 15.49 |
| 28 | 14.44 |
| 29 | 11.97 |

TABLE 3

Analytical data for synthesized compounds

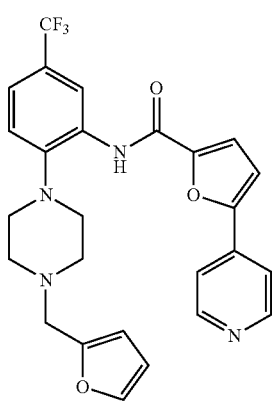 [SMILES: O=C(Nc1cc(C(F)(F)F)ccc1N1CCN(Cc2ccco2)CC1)c1ccc(-c2ccncc2)o1]

Compound 5:
N-(2-(4-(furan-2-ylmethyl)piperazin-1-yl)-5-(trifluoromethyl)phenyl)-5-(pyridin-4-yl)(furan-2-carboxamide
Mp: 95-97° C.
$^1$H NMR (400 MHz, CDCl$_3$) δ 2.78 (br s, 4H), 3.03 (t, J = 4.8 Hz, 4H), 3.63 (s, 2H), 6.22 (d, J = 3.0 Hz, 1H), 6.31 (dd, J = 3.3, 1.9 Hz, 1H), 7.05 (d, J = 3.7 Hz, 1H), 7.30 (d, J = 8.3 Hz, 1H), 7.35-7.39 (m, 3H), 7.70 (dd, J = 4.2, 1.6 Hz, 2H), 8.75 (dd, J = 4.2, 1.6 Hz, 2H), 8.85 (d, J = 1.4 Hz, 1H), 9.61 (br s, 1H)
HRMS (ESI-MS): m/z calcd for C$_{26}$H$_{23}$F$_3$N$_4$O$_3$ (M$^+$ + H) 497.17950, found 497.17470

TABLE 3-continued

Analytical data for synthesized compounds

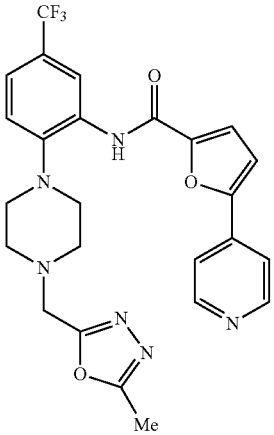 [SMILES: Cc1nnc(CN2CCN(c3ccc(C(F)(F)F)cc3NC(=O)c3ccc(-c4ccncc4)o3)CC2)o1]

Compound 6:
N-(2-(4-((5-methyl-1,3,4-oxadiazol-2-yl)methyl)piperazin-1-yl)-5-(trifluoromethyl)phenyl)-5-(pyridin-4-yl)furan-2-carboxamide
Mp: 192-194° C.
$^1$H NMR (300 MHz, CDCl$_3$) δ 2.53 (s, 3H), 2.89 (br s, 4H), 3.05 (t, J = 4.8 Hz, 4H), 3.82 (s, 2H), 7.06 (d, J = 3.6 Hz, 1H), 7.30 (d, J = 8.3 Hz, 1H), 7.36-7.41 (m, 2H), 7.67 (dd, J = 4.6, 1.2 Hz, 2H), 8.76 (dd, 4.6, 1.2 Hz, 2H), 8.84 (d, J = 1.2 Hz, 1H), 9.53 (br s, 1H)
HRMS (ESI-MS): m/z calcd for C$_{25}$H$_{23}$F$_3$N$_6$O$_3$ (M$^+$ + H) 513.18565, found 513.1808

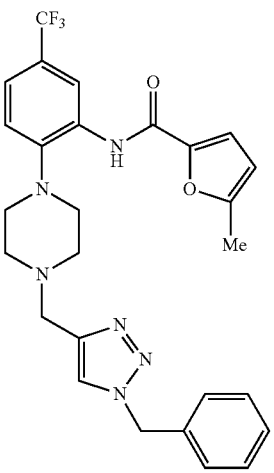 [SMILES: Cc1ccc(C(=O)Nc2cc(C(F)(F)F)ccc2N2CCN(Cc3cn(Cc4ccccc4)nn3)CC2)o1]

Compound 7:
N-(2-(4-((1-benzyl-1H-1,2,3-triazol-4-yl)methyl)piperazin-1-yl)-5-(trifluoromethyl)phenyl)-5-methylfuran-2-carboxamide
Mp: 120-124° C.
$^1$H NMR (300 MHz, CDCl$_3$) δ 2.44 (s, 3H), 2.77 (br s, 4H), 2.96 (t, J = 4.8 Hz, 4H), 3.75 (s, 2H), 5.53 (s, 2H), 6.19 (dd, J = 3.6, 0.9 Hz, 1H), 7.14 (d, J = 3.4 Hz, 1H), 7.20 (d, J = 8.3 Hz, 1H), 7.27-7.45 (m, 7H), 8.80 (d, J = 1.6 Hz, 1H), 9.38 (br s, 1H)
HRMS (ESI-MS): m/z calcd for C$_{27}$H$_{27}$F$_3$N$_6$O$_2$ (M$^+$ + H) 525.22204, found 525.2168

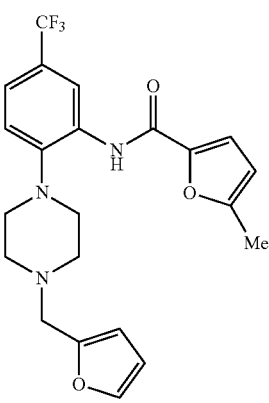 [SMILES: Cc1ccc(C(=O)Nc2cc(C(F)(F)F)ccc2N2CCN(Cc3ccco3)CC2)o1]

Compound 8:
5-methyl-N-(2-(4-((furan-2-yl)methyl)piperazin-1-yl)-5-(trifluoromethyl)phenyl)furan-2-carboxamide
$^1$H NMR (300 MHz, CDCl$_3$) δ 2.42 (s, 3H), 2.75 (br s, 4H), 3.00 (t, J = 4.8 Hz, 4H), 3.68 (s, 2H), 6.19 (d, J = 3.4 Hz, 1H), 6.26 (dd, J = 3.1 Hz, 1H), 6.35 (dd, J = 3.0, 2.0 Hz, 1H), 7.14 (d, J = 3.4 Hz, 1H), 7.23 (d, J = 8.3 Hz, 1H), 7.32 (dd, J = 8.3, 1.7 Hz, 1H), 7.41 (d, J = 1.7 Hz, 1H), 8.81 (d, J = 1.7 Hz, 1H), 9.37 (br s, 1H)
HRMS (ESI-MS): m/z calcd for C$_{22}$H$_{22}$F$_3$N$_3$O$_3$ (M$^+$ + Na) 456.1511, found 456.1474

TABLE 3-continued

Analytical data for synthesized compounds

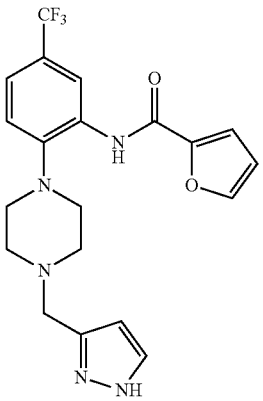 [SMILES: O=C(Nc1cc(C(F)(F)F)ccc1N1CCN(Cc2cc[nH]n2)CC1)c1ccco1]

Compound 9:
N-(2-(4-((1H-pyrazol-3-yl)methyl)piperazin-1-yl)-5-(trifluoromethyl)-phenyl)furan-2-carboxamide
$^1$H NMR (400 MHz, DMSO) δ 12.630 (s, 1H), 9.439 (s, 1H), 8.514 (s, 1H), 7.977 (s, 1H), 7.680 (s, 1H), 7.497-7.431 (dd, J = 18.0, 8.4 Hz, 2H), 7.333-7.325 (d, J = 3.2 Hz, 1H), 6.784-6.771 (dd, J = 3.6, 1.6 Hz, 1H), 6.200 (s, 1H), 3.617 (s, 2H), 2.929 (s, 4H), 2.628 (m, 4H).
MS (ESI-MS): m/z calcd for $C_{20}H_{20}F_3N_5O_2$ [MH]$^+$ 420.16, found 420.33.

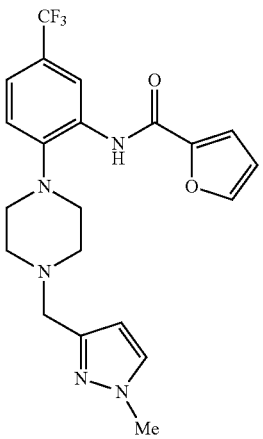 [SMILES: Cn1ccc(CN2CCN(c3ccc(C(F)(F)F)cc3NC(=O)c3ccco3)CC2)n1]

Compound 10:
N-(2-(4-((1-methyl-1H-pyrazol-3-yl)methyl)piperazin-1-yl)-5-(trifluoromethyl)phenyl)furan-2-carboxamide
$^1$H NMR (400 MHz, DMSO) δ 10.978 (s, 1H), 9.407 (s, 1H), 8.464 (s, 1H), 7.975 (s, 1H), 7.753 (s, 1H), 7.521-7.501 (d, J = 8.0 Hz, 1H), 7.446-7.425 (d, J = 8.4 Hz, 1H), 7.366 (s, 1H), 6.784 (s, 1H), 6.382 (s, 1H), 3.853 (s, 4H), 3.109 (s, 4H).
MS (ESI-MS): m/z calcd for $C_{21}H_{22}F_3N_5O_2$ [MH]$^+$ 434.17, found 434.36.

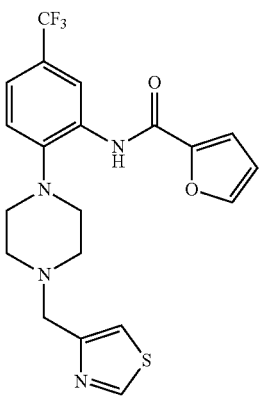 [SMILES: O=C(Nc1cc(C(F)(F)F)ccc1N1CCN(Cc2cscn2)CC1)c1ccco1]

Compound 11:
N-(2-(4-(thiazol-4-ylmethyl)piperazin-1-yl)-5-(trifluoromethyl)-phenyl)furan-2-carboxamide
$^1$H NMR (400 MHz, DMSO) δ 9.424 (s, 1H), 9.146 (s, 1H), 8.493 (s, 1H), 7.975-7.973 (d, J = 0.8 Hz, 1H), 7.664 (s, 1H), 7.506-7.488 (d, J = 7.2 Hz, 1H), 7.452-7.431 (d, J = 8.4 Hz, 1H), 7.344-7.336 (d, J = 3.2 Hz, 1H), 6.786-6.773 (dd, J = 3.4, 1.8 Hz, 1H), 3.865 (s, 2H), 3.006 (s, 4H), 2.676 (s, 4H).
MS (ESI-MS): m/z calcd for $C_{20}H_{19}F_3N_4O_2S$ [MH]$^+$ 437.12, found 437.33.

TABLE 3-continued

Analytical data for synthesized compounds

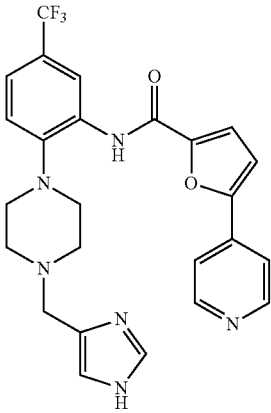 [SMILES: O=C(Nc1cc(C(F)(F)F)ccc1N1CCN(Cc2c[nH]cn2)CC1)c1ccc(-c2ccncc2)o1]

Compound 12:
N-(2-(4-((1H-imidazol-4-yl)methyl)piperazin-1-yl)-5-(trifluoromethyl)-phenyl)-5-(pyridin-4-yl)furan-2-carboxamide
$^1$H NMR (300 MHz; CDCl$_3$) δ 2.81 (br s, 4H), 3.00 (t, J = 4.5 Hz, 4H), 3.63 (s, 2H), 6.94 (s, 1H), 7.05 (d, J = 3.7 Hz, 1H), 7.28 (d, J = 8.3 Hz, 1H), 7.34-7.38 (m, 2H), 7.62 (s, 1H), 7.68-7.71 (m, 2H), 8.72-8.74 (m, 2H), 8.83 (d, J = 1.6 Hz, 1H), 9.61 (s, 1H)
HRMS (ESI-MS): m/z calcd for C$_{25}$H$_{24}$F$_3$N$_6$O$_2$ (M$^+$ + H) 497.1913, found 497.1902

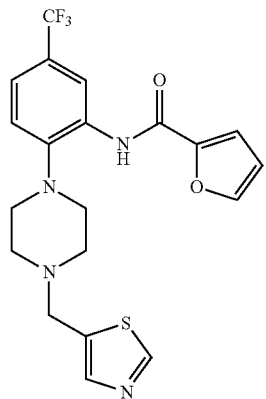 [SMILES: O=C(Nc1cc(C(F)(F)F)ccc1N1CCN(Cc2cncs2)CC1)c1ccco1]

Compound 13:
N-(2-(4-(thiazol-5-ylmethyl)piperazin-1-yl)-5-(trifluoromethyl)-phenyl)furan-2-carboxamide
$^1$H NMR (400 MHz, DMSO) δ 9.435 (s, 1H), 9.081 (s, 1H), 8.505 (s, 1H), 7.987-7.985 (d, J = 0.8 Hz, 1H), 7.834 (s, 1H), 7.467-7.459 (d, J = 3.2 Hz, 2H), 7.338-7.329 (d, J = 3.6 Hz, 1H), 6.782-6.770 (dd, J = 3.2, 1.6 Hz, 1H), 3.897 (s, 2H), 2.949-2.928 (m, 4H), 2.652 (s, 4H).
MS (ESI-MS): m/z calcd for C$_{20}$H$_{19}$F$_3$N$_4$O$_2$S [MH]$^+$ 437.12, found 437.30.

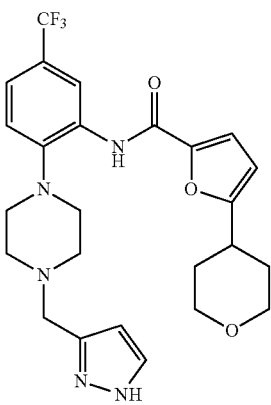 [SMILES: O=C(Nc1cc(C(F)(F)F)ccc1N1CCN(Cc2cc[nH]n2)CC1)c1ccc(C2CCOCC2)o1]

Compound 14:
N-(2-(4-((1H-pyrazol-3-yl)methyl)piperazin-1-yl)-5-(trifluoromethyl)-phenyl)-5-(tetrahydro-2H-pyran-4-yl)furan-2-carboxamide
$^1$H NMR (400 MHz, DMSO) δ 12.368 (s, 1H), 9.445 (s, 1H), 8.591 (s, 1H), 7.479 (s, 2H), 7.257 (s, 1H), 6.476-6.468 (d, J = 3.2 Hz, 1H), 6.160 (s, 1H), 4.447 (s, 1H), 4.001-3.969 (m, 2H), 3.551-3.497 (m, 3H), 3.124-3.066 (m, 2H), 2.956 (s, 4H), 1.995-1.963 (m, 2H), 1.782-1.753 (m, 2H).
MS (ESI-MS): m/z calcd for C$_{25}$H$_{28}$F$_3$N$_5$O$_3$ [MH]$^+$ 504.21, found 504.42.

TABLE 3-continued

Analytical data for synthesized compounds

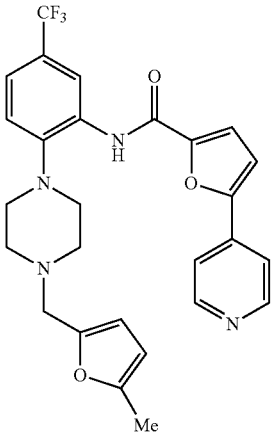 [SMILES: Cc1ccc(CN2CCN(c3ccc(C(F)(F)F)cc3NC(=O)c3ccc(-c4ccncc4)o3)CC2)o1]

Compound 15:
N-(2-(4-((5-methylfuran-2-yl)methyl)piperazin-1-yl)-5-(trifluoromethyl)-phenyl)-5-(pyridin-4-yl)furan-2-carboxamide
$^1$H NMR (300 MHz, CDCl$_3$) δ 2.27 (d, J = 0.7 Hz, 3H), 2.78 (br s, 4H), 3.03-3.06 (m, 4H), 3.57 (s, 2H), 5.88-5.90 (m, 1H), 6.09 (d, J = 3.0 Hz, 1H), 7.06 (d, J = 3.7 Hz, 1H), 7.31 (d, J = 8.3 Hz, 1H), 7.37-7.40 (m, 2H), 7.70-7.72 (m, 2H), 8.75-8.77 (m, 2H), 8.86 (d, J = 1.9 Hz, 1H), 9.64 (br s, 1H). HRMS (ESI-MS): m/z calcd for C$_{27}$H$_{25}$F$_3$N$_4$O$_3$ [MNa]$^+$ 533.1776, found 533.1761.

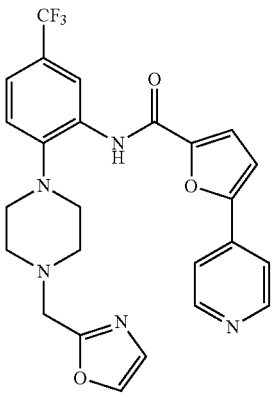 [SMILES: O=C(Nc1cc(C(F)(F)F)ccc1N1CCN(Cc2ncco2)CC1)c1ccc(-c2ccncc2)o1]

Compound 16:
N-(2-(4-(oxazol-2-ylmethyl)piperazin-1-yl)-5-(trifluoromethyl)phenyl)-5-(pyridin-4-yl)furan-2-carboxamide
$^1$H NMR (300 MHz, CDCl$_3$) δ 2.87 (br s, 4H), 3.04-3.07 (m, 4H), 3.79 (s, 2H), 7.05-7.07 (m, 2H), 7.31 (d, J = 8.3 Hz, 1H), 7.37-7.40 (m, 2H), 7.61 (d, J = 0.8 Hz, 1H), 7.66-7.69 (m, 2H), 8.76-8.78 (m, 2H), 8.85 (d, J = 2.0 Hz, 1H), 9.56 (br s, 1H). HRM (ESI-MS): m/z calcd for C$_{25}$H$_{23}$F$_3$N$_5$O$_3$ (M$^+$ + H) 498.1753, found 498.1733

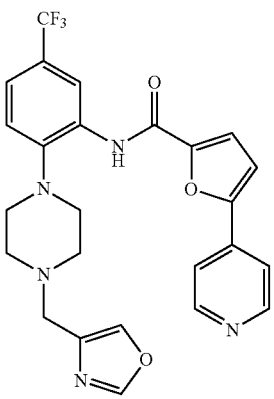 [SMILES: O=C(Nc1cc(C(F)(F)F)ccc1N1CCN(Cc2cocn2)CC1)c1ccc(-c2ccncc2)o1]

Compound 17:
N-(2-(4-(oxazol-4-ylmethyl)piperazin-1-yl)-5-(trifluoromethyl)phenyl)-5-(pyridin-4-yl)furan-2-carboxamide
$^1$H NMR (300 MHz, CDCl$_3$) δ 2.85 (br s, 4H), 3.03-3.06 (m, 4H), 3.60 (s, 2H), 7.06 (d, J = 3.8 Hz, 1H), 7.31 (d, J = 8.1 Hz, 1H), 7.37-7.40 (m, 2H), 7.59 (d, J = 0.7 Hz, 1H), 7.69-7.72 (m, 2H), 7.85 (s, 1H), 8.75-8.7 (m, 2H), 8.86 (d, J = 1.7 Hz, 1H), 9.62 (br s, 1H). HRMS (ESI-MS): m/z calcd for C$_{25}$H$_{22}$F$_3$N$_5$O$_3$Na [MNa]$^+$ 520.1572, found 520.1558.

TABLE 3-continued

Analytical data for synthesized compounds

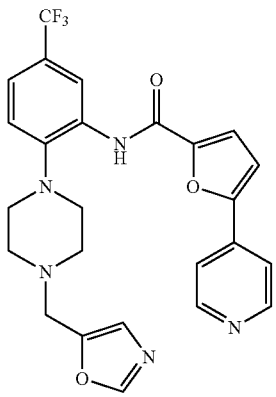 [SMILES: O=C(Nc1cc(C(F)(F)F)ccc1N1CCN(Cc2cnco2)CC1)c1ccc(-c2ccncc2)o1]

Compound 18:
N-(2-(4-(oxazol-5-ylmethyl)piperazin-1-yl)-5-(trifluoromethyl)phenyl)-5-(pyridin-4-yl)furan-2-carboxamide
$^1$H NMR (300 MHz, CDCl$_3$) δ 2.81 (br s, 4H), 3.03-3.06 (m, 4H), 3.68 (s, 2H), 6.99 (s, 1H), 7.07 (d, J = 3.7 Hz, 1H), 7.31 (d, J = 8.5 Hz, 1H), 7.38-7.41 (m, 2H), 7.69-7.71 (m, 2H), 7.84 (s, 1H), 8.75-8.77 (m, 2H), 8.86 (d, J = 1.8 Hz, 1H), 9.59 (br s, 1H).
HRMS (ESI-MS): m/z calcd for C$_{25}$H$_{23}$F$_3$N$_5$O$_3$ (M$^+$ + H) 498.1753, found 498.1735

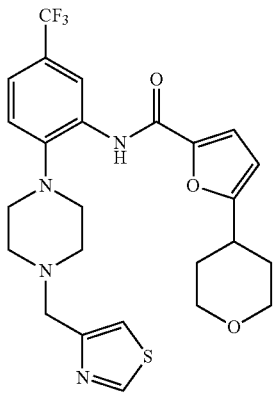 [SMILES: O=C(Nc1cc(C(F)(F)F)ccc1N1CCN(Cc2cscn2)CC1)c1ccc(C2CCOCC2)o1]

Compound 19:
5-(tetrahydro-2H-pyran-4-yl)-N-(2-(4-(thiazol-4-ylmethyl)piperazin-1-yl)-5-(trifluoromethyl)phenyl)furan-2-carboxamide
$^1$H NMR (400 MHz, DMSO) δ 9.48 (s, 1H), 9.077 (d, J = 1.2 Hz 1H), 8.62 (s, 1H), 7.56 (s, 1H), 7.49 (d, J = 8.4 Hz, 1H), 7.25 (d, J = 3.6 Hz, 1H), 6.48 (d, J = 3.2 Hz, 1H), 3.99 (d, J = 10 Hz, 2H), 3.74 (s, 2H), 3.57 (t, 2H), 3.10 (m, 1H), 2.95 (m, 4H), 2.72 (m, 4H) 1.98 (d, 2H), 1.84-1.74 (m, 2H).
MS (ESI-MS): m/z calcd for C$_{25}$H$_{28}$F$_3$N$_4$O$_2$S [MH]$^+$ 528.18, found 521.16

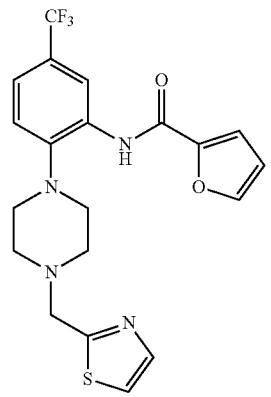 [SMILES: O=C(Nc1cc(C(F)(F)F)ccc1N1CCN(Cc2nccs2)CC1)c1ccco1]

Compound 20:
N-(2-(4-(thiazol-2-ylmethyl)piperazin-1-yl)-5-(trifluoromethyl)-phenyl)furan-2-carboxamde
$^1$H NMR (400 MHz, DMSO) δ 9.45 (s, 1H), 8.528 (s, 1H), 8.01 (s, 1H), 7.76 (m, 2H), 7.49 (s, 2H), 7.34-7.33 (d, J = 3.1 Hz, 1H), 6.77 (s, 1H), 3.99 (s, 2H), 2.98 (m, 4H), 2.767 (m, 4H).
MS (ESI-MS): m/z calcd for C$_{20}$H$_{20}$F$_3$N$_4$O$_2$S [MH]$^+$ 437.12, found 437.14

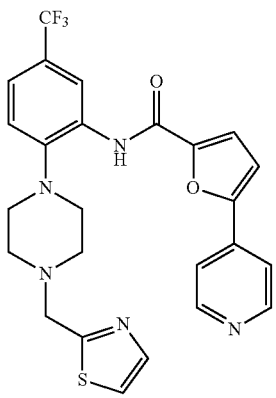 [SMILES: O=C(Nc1cc(C(F)(F)F)ccc1N1CCN(Cc2nccs2)CC1)c1ccc(-c2ccncc2)o1]

Compound 21:
5-(pyridin-4-yl)-N-(2-(4-(thiazol-2-ylmethyl)piperazin-1-yl)-5-(trifluoromethyl)phenyl)furan-2-carboxamide
$^1$H NMR (400 MHz, DMSO) δ 9.74 (s, 1H), 8.78 (d, J = 5.9 Hz, 2H), 8.54 (s, 1H), 7.92 (d, J = 5.9 Hz, 2H), 7.70 (m, 2H), 7.54 (m, 4H), 3.942 (s, 2H), 3.02 (m, 4H), 2.80 (m ,4H).
MS (ESI-MS): m/z calcd for C$_{25}$H$_{23}$F$_3$N$_5$O$_2$S [MH]$^+$ 514.14, found 514.30.

TABLE 3-continued

Analytical data for synthesized compounds

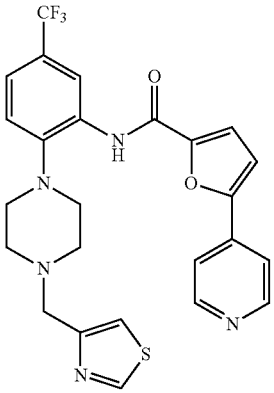 [SMILES: O=C(Nc1cc(C(F)(F)F)ccc1N1CCN(Cc2cscn2)CC1)c1ccc(-c2ccncc2)o1]

Compound 22:
5-(pyridin-4-yl)-N-(2-(4-(thiazol-4-ylmethyl)piperazin-1-yl)-5-(trifluoromethyl)phenyl)furan-2-carboxamide
$^1$H NMR (400 MHz, DMSO) δ 9.74 (s, 1H), 9.04 (s, 1H), 8.77 (s, 2H), 8.53 (s, 1H), 7.92 (s, 2H), 7.52 (m, 5H), 3.74 (s, 2H), 2.99 (m, 4H), 2.73 (m, 4H).
MS (ESI-MS): m/z calcd for $C_{25}H_{23}F_3N_5O_2S$ [MH]$^+$ 513.14, found 514.20.

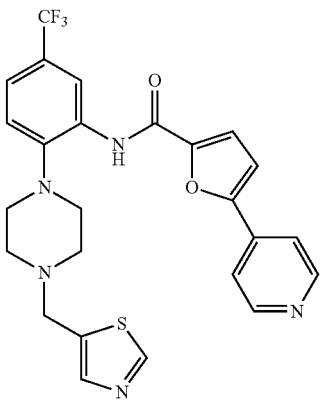 [SMILES: O=C(Nc1cc(C(F)(F)F)ccc1N1CCN(Cc2cncs2)CC1)c1ccc(-c2ccncc2)o1]

Compound 23:
5-(pyridin-4-yl)-N-(2-(5-(thiazol-2-ylmethyl)piperazin-1-yl)-5-(trifluoromethyl)phenyl)furan-2-carboxamide
$^1$H NMR (400 MHz, DMSO) δ 9.70 (s, 1H), 9.03 (s, 1H), 8.79 (d, J = 6.0 Hz, 2H), 8.51 (s, 1H), 7.91 (d, J = 6.0 Hz, 2H), 7.76 (s, 1H), 7.56 (d, J = 3.7 Hz, 1H), 7.50 (m, 3H), 3.83 (s, 2H), 2.99 (sm 4H), 2.69 (m, 4H).
MS (ESI-MS): m/z calcd for $C_{25}H_{23}F_3N_5O_2S$ [MH]$^+$ 514.14, found 514.25.

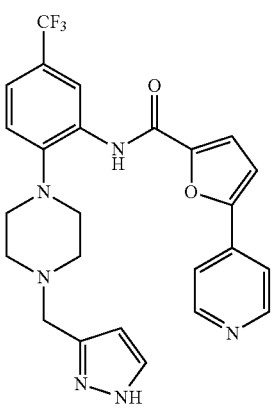 [SMILES: O=C(Nc1cc(C(F)(F)F)ccc1N1CCN(Cc2cc[nH]n2)CC1)c1ccc(-c2ccncc2)o1]

Compound 24:
N-(2-(4-((1H-pyrazol-3-yl)methyl)piperazin-1-yl)-5-(trifluoromethyl)-phenyl)-5-(pyridin-4-yl)furan-2-carboxamide
$^1$H NMR (400 MHz, DMSO) δ 12.65 (s, 1H), 9.73 (s, 1H), 8.78 (d, J = 5.4 Hz, 2H), 8.55 (s, 1H), 7.92 (d, J = 5.5 Hz, 2H), 7.52 (m, 5H), 6.15 (s, 1H), 3.59 (s, 2H), 2.98 (m, 4H), 2.68 (m, 4H).
MS (ESI-MS): m/z calcd for $C_{25}H_{24}F_3N_6O_2$ [MH]$^+$ 497.48, found 497.3.

TABLE 3-continued

Analytical data for synthesized compounds

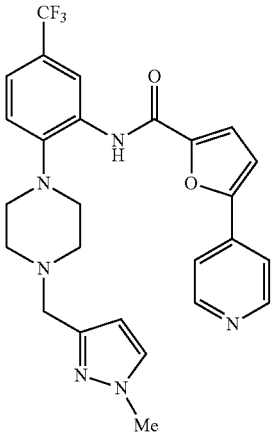 [SMILES: Cn1ccc(CN2CCN(c3ccc(C(F)(F)F)cc3NC(=O)c3ccc(-c4ccncc4)o3)CC2)n1]

Compound 25:
N-(2-(4-((1-methyl-1H-pyrazol-3-yl)methyl)piperazin-1-yl)-5-(trifluoromethyl)phenyl)-5-(pyridin-4-yl)furan-2-carboxamide
$^1$H NMR (400 MHz, DMSO) δ 9.73 (s, 1H), 8.77 (d, J = 5.6 Hz, 2H), 8.54 (s, 1H), 7.92 (d, J = 5.5 Hz, 2H), 7.57 (m, 2H), 7.50 (m, 3H), 6.13 (s, 1H), 3.77 (s, 3H), 3.51 (s, 2H), 2.98 (m, 4H), 2.68 (m, 4H).
MS (ESI-MS): m/z calcd for $C_{26}H_{26}F_3N_6O_2$ [MH]$^+$ 511.20, found 511.30.

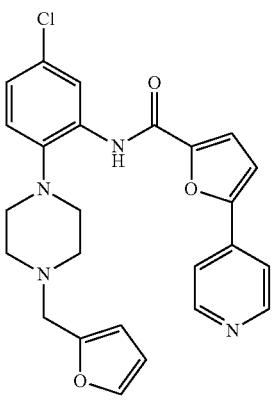 [SMILES: O=C(Nc1cc(Cl)ccc1N1CCN(Cc2ccco2)CC1)c1ccc(-c2ccncc2)o1]

Compound 26:
N-(5-chloro-2-(4-(furan-2-ylmethyl)piperazin-1-yl)phenyl)-5-(pyridin-4-yl)furan-2-carboxamide
Mp: 153-156° C.
$^1$H NMR (300 MHz, CDCl$_3$) δ 2.73-2.79 (m, 4H), 2.97-3.00 (m, 4H), 3.62 (s, 2H), 6.22-6.23 (m, 1H), 6.31 (dd, J = 3.5, 1.2 Hz, 1H), 7.04-7.09 (m, 2H), 7.15-7.18 (m, 1H), 7.36-7.38 (m, 2H), 7.69-7.71 (m, 2H), 8.59 (d, J = 2.3 Hz, 1H), 8.74-8.76 (m, 2H), 9.72 (s, 1H).
HRMS (ESI-MS): m/z calcd for $C_{25}H_{23}N_4O_3ClNa$ (M$^+$ + Na) 485.1356, found 485.1337.

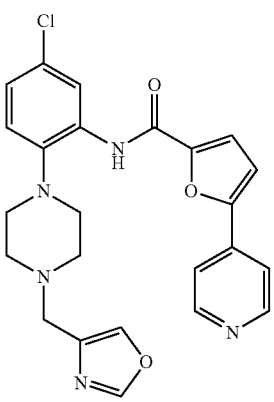 [SMILES: O=C(Nc1cc(Cl)ccc1N1CCN(Cc2cocn2)CC1)c1ccc(-c2ccncc2)o1]

Compound 27:
N-(5-chloro-2-(4-(oxazol-4-ylmethyl)piperazin-1-yl)phenyl)-5-(pyridin-4-yl)furan-2-carboxamide
$^1$H NMR (600 MHz, CDCl$_3$) δ 2.85 (br s, 4H), 3.01 (br s, 4H), 3.62 (s, 2H), 7.05 (d, J = 3.7 Hz, 1H), 7.08-7.10 (m, 1H), 7.17 (d, J = 8.3 Hz, 1H), 7.37 (d, J = 3.7 Hz, 1H), 7.69-7.70 (m, 2H), 7.84 (s, 1H), 8.60 (d, J = 1.6 Hz, 1H), 8.75-8.76 (m, 2H), 9.69 (br s, 1H).
HRMS (ESI-MS): m/z calcd for $C_{24}H_{23}{}^{35}ClN_5O_3$ [MH]$^+$ 464.1489, found 464.1475

TABLE 3-continued

Analytical data for synthesized compounds

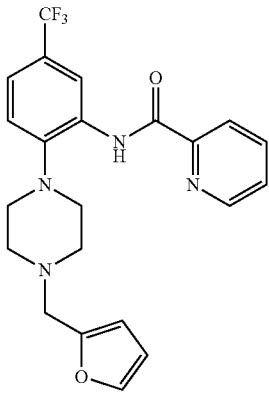 [SMILES: O=C(Nc1cc(Cl)ccc1N1CCN(Cc2ccco2)CC1)c1ccccn1]

Compound 28:
N-(2-(4-(furan-2-ylmethyl)piperazin-1-yl)-5-(trifluoromethyl)phenyl)-picolinamide
$^1$H NMR (300 MHz, CDCl$_3$) δ 2.77-2.82 (m, 4H), 3.01-3.04 (m, 4H), 3.71 (s, 2H), 6.27-6.28 (m, 1H), 6.37-6.38 (m, 1H), 7.20-7.23 (m, 1H), 7.34 (ddd, J = 8.3, 2.1, 1.0 Hz, 1H), 7.44 (dd, J = 1.9, 0.8 Hz, 1H), 7.48-7.52 (m, 1H), 7.92 (td, J = 7.8, 1.7 Hz, 1H), 8.29 (dt, J = 7.8, 1.0 Hz, 1H), 8.60 (dq, J = 4.7, 0.7 Hz, 1H), 8.90 (d, J = 1.9 Hz, 1H), 11.04 (s, 1H)
HRMS (ESI-MS): m/z calcd for C$_{22}$H$_{22}$F$_3$N$_4$O$_2$Na (M$^+$ + Na) 431.1695, found 431.1680

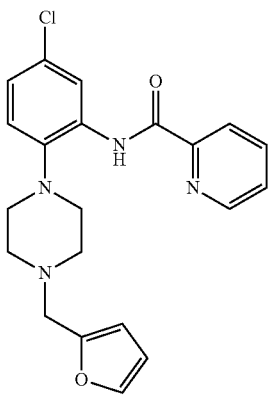

Compound 29:
N-(5-chloro-2-(4-(furan-2-ylmethyl)piperazin-1-yl)phenyl)picolinamide
$^1$H NMR (300 MHz, CDCl$_3$) δ 2.77-2.82 (m, 4H), 2.98-3.00 (m, 4H), 3.72 (s, 2H), 6.30 (d, J = 2.8 Hz, 1H), 6.39 (dd, J = 1.8, 1.2 Hz, 1H), 7.05-7.11 (m, 2H), 7.45 (dd, J = 1.9, 0.8 Hz, 1H), 7.50-7.52 (m, 1H), 7.93 (dt, J = 7.8, 1.7 Hz, 1H), 8.29-8.31 (m, 1H), 8.61-8.62 (m, 1H), 8.66 (d, J = 2.3 Hz, 1H), 11.13 (s, 1H)
HRMS (ESI-MS): m/z calcd for C$_{21}$H$_{22}$ClN$_4$O (M$^+$ + H) 397.1431, found 397.1418

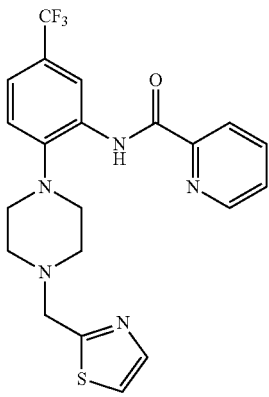 [SMILES: O=C(Nc1cc(C(F)(F)F)ccc1N1CCN(Cc2nccs2)CC1)c1ccccn1]

Compound 30:
N-(2-(4-(thiazol-2-ylmethyl)piperazin-1-yl)-5-(trifluoromethyl)-phenyl)picolinamide
$^1$H NMR (400 MHz, DMSO) δ 10.99 (s, 1H), 8.79 (s, 1H), 8.75 (d, J = 4.6 Hz, 1H), 8.20 (d, J = 7.7 Hz, 1H), 8.12 (td, J = 7.7, 1.6 Hz, 1H), 7.78 (d, J = 3.3 Hz, 1H), 7.73 (ddd, J = 9.1, .5, 2.2 Hz, 2H), 7.48 (d, J = 1.0 Hz, 2H), 4.03 (s, 2H), 3.008-2.987 (m, 4H), 2.831 (m, 4H).
MS (ESI-MS): m/z calcd for C$_{21}$H$_{31}$F$_3$N$_5$OS [MH]$^+$ 448.48, found 448.14

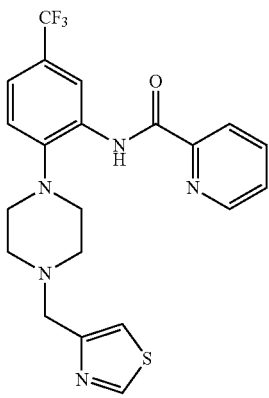 [SMILES: O=C(Nc1cc(C(F)(F)F)ccc1N1CCN(Cc2cscn2)CC1)c1ccccn1]

Compound 31:
N-(2-(4-(thiazol-4-ylmethyl)piperazin-1-yl)-5-(trifluoromethyl)phenyl)-picolinamide
$^1$H NMR (400 MHz, DMSO) δ 10.97 (s, 1H), 9.13 (d, J = 1.8 Hz, 1H), 8.79 (d, 1H), 8.69 (d, J = 4.5 Hz, 1H), 8.20 (d, J = 7.7 Hz, 1H), 8.13 (td, J = 7.7, 1.5 Hz, 1H), 7.75 (dd, J = 6.3, 4.8 Hz, 1H), 7.61 (s, 1H), 7.46 (m, 2H), 3.85 (s, 2H), 2.97 (m, 4H), 2.77 (m, 4H).
MS (ESI-MS): m/z calcd for C$_{21}$H$_{21}$F$_3$N$_5$O [MH]$^+$ 448.14, found 448.10.

TABLE 3-continued

Analytical data for synthesized compounds

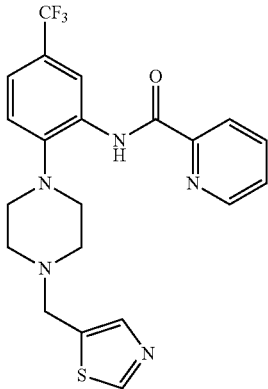 [SMILES: O=C(Nc1cc(C(F)(F)F)ccc1N1CCN(Cc2cncs2)CC1)c1ccccn1]

Compound 32:
N-(2-(4-(thiazol-5-ylmethyl)piperazin-1-yl)-5-(trifluoromethyl)phenyl)-picolinamide
$^1$H NMR (400 MHz, DMSO) δ 10.97 (s, 1H), 9.09 (s, 1H), 8.75 (d, J = 34.1 Hz, 2H), 8.16 (m, 2H), 7.86 (s, 1H), 7.74 (s, 1H), 7.47 (s, 2H), 3.95 (s, 2H), 2.97 (m, 4H), 2.72 (m, 4H).
MS (ESI-MS): m/z calcd for $C_{21}H_{31}F_3N_5OS$ [MH]$^+$ 448.48, found 448.11.

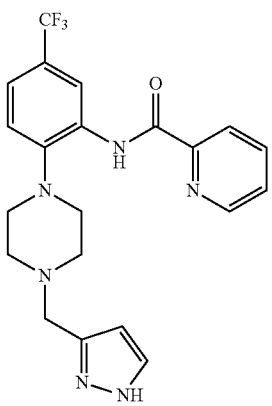 [SMILES: O=C(Nc1cc(C(F)(F)F)ccc1N1CCN(Cc2cc[nH]n2)CC1)c1ccccn1]

Compound 33:
N-(2-(4-((1H-pyrazol-3-yl)methyl)piperazin-1-yl)-5-(trifluoromethyl)-phenyl)picolinamide
$^1$H NMR (400 MHz, DMSO) δ 12.69 (s, 1H), 10.98 (s, 1H), 8.73 (m, 2H), 8.15 (m, 2H), 7.67 (m, 2H), 7.45 (d, J = 6.7 Hz, 2H), 6.22 (s, 1H), 3.67 (s, 2H), 2.94 (m, 4H), 2.69 (m, 4H).
MS (ESI-MS): m/z calcd for $C_{21}H_{22}F_3N_6O$ [MH]$^+$ 431.43, found 431.24.

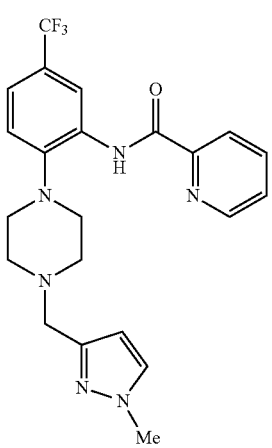 [SMILES: Cn1ccc(CN2CCN(c3ccc(C(F)(F)F)cc3NC(=O)c3ccccn3)CC2)n1]

Compound 34:
N-(2-(4-((1-methyl-1H-pyrazol-3-yl)methyl)piperazin-1-yl)-5-(trifluoromethyl)phenyl)picolinamide
$^1$H NMR (400 MHz, DMSO) δ 10.99 (s, 1H), 8.79 (s, 1H), 8.70 (d, J = 4.0 Hz, 1H), 8.20 (d, J = 7.6 Hz, 1H), 8.13 (m, 1H), 7.75 (m, 1H), 7.65 (s, 1H), 7.46 (m, 2H) 6.18 (s, 1H), 3.82 (s, 3H), 3.58 (s, 2H), 2.94 (m, 4H), 2.69 (m, 4H).
MS (ESI-MS): m/z calcd for $C_{22}H_{24}F_3N_6O$ [MH]$^+$ 445.19, found 445.17

TABLE 3-continued

Analytical data for synthesized compounds

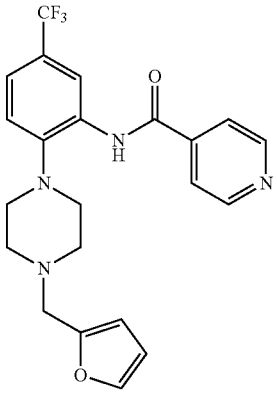 [SMILES: O=C(Nc1cc(C(F)(F)F)ccc1N1CCN(Cc2ccco2)CC1)c1ccncc1]

Compound 35:
N-(2-(4-(furan-2-ylmethyl)piperazin-1-yl)-5-(trifluoromethyl)-phenyl)isonicotinamide
$^1$H NMR (300 MHz, CDCl$_3$) δ 2.69-2.74 (m, 4H), 2.97-3.00 (m, 4H), 3.69 (s, 2H), 6.26-6.27 (m, 1H), 6.38 (dd, J = 1.8, 1.2 Hz, 1H), 7.30-7.32 (m, 1H), 7.38-7.41 (m, 1H), 7.43 (dd, J = 1.8, 0.8 Hz, 1H), 7.71-7.73 (m, 2H), 8.83-8.85 (m, 3H), 9.50 (s, 1H)
HRMS (ESI-MS): m/z calcd for C$_{22}$H$_{21}$F$_3$N$_4$NaO$_2$ (M$^+$ + Na) 453.1514, found 453.1501

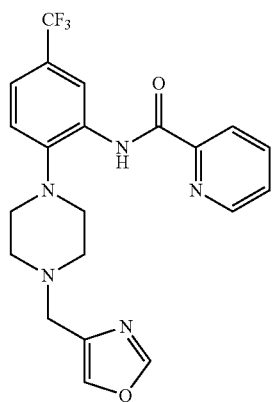 [SMILES: O=C(Nc1cc(C(F)(F)F)ccc1N1CCN(Cc2cocn2)CC1)c1ccccn1]

Compound 36:
N-(2-(4-(oxazol-4-ylmethyl)piperazin-1-yl)-5-(trifluoromethyl)phenyl)-picolinamide
$^1$H NMR (400 MHz, CDCl$_3$) δ 2.84 (br s, 4H), 3.01-3.04 (m, 4H), 3.66 (s, 2H), 7.21 (d, J = 8.3 Hz, 1H), 7.33 (dd, J = 8.2, 1.6 Hz, 1H), 7.48-7.52 (m, 1H), 7.64 (br s, 1H), 7.89 (s, 1H), 7.92 (dd, J = 7.7, 1.7 Hz, 1H), 8.27-8.29 (m, 1H), 8.61-8.63 (m, 1H), 8.89 (d, J = 2.0 Hz, 1H), 11.03 (br s, 1H). HRMS (ESI-MS): m/z calcd for C$_{21}$H$_{21}$F$_3$N$_5$O$_2$ [MNa]$^+$ 432.1640, found 432.1647

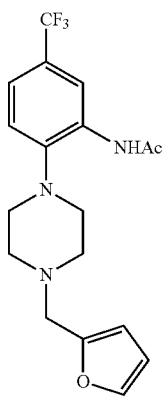 [SMILES: CC(=O)Nc1cc(C(F)(F)F)ccc1N1CCN(Cc2ccco2)CC1]

Compound 37:
N-(2-(4-(furan-2-ylmethyl)piperazin-1-yl)-5-(trifluoromethyl)phenyl)acetamide
$^1$H NMR (600 MHz, CDCl$_3$) δ 2.21 (s, 3H), 2.68 (br s, 4H), 2.93-2.94 (m, 4H), 3.65 (s, 2H), 6.26 (d, J = 3.0 Hz, 1H), 6.34-6.35 (m, 1H), 7.20 (d, J = 8.3 Hz, 1H), 7.30 (d, J = 8.3 Hz, 1H), 7.41 (s, 1H), 8.34 (s, 1H), 8.66 (s, 1H).
HRMS (ESI-MS): m/z calcd for C$_{18}$H$_{21}$F$_3$N$_3$O$_2$ [MH]$^+$ 368.1586, found 368.1579

TABLE 3-continued

Analytical data for synthesized compounds

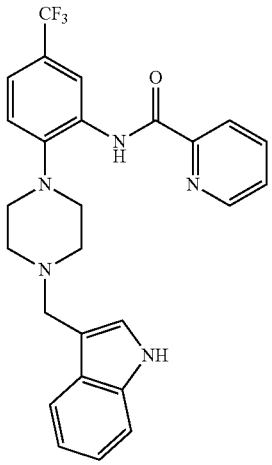 [SMILES: O=C(Nc1cc(C(F)(F)F)ccc1N1CCN(Cc2c[nH]c3ccccc23)CC1)c1ccccn1]

Compound 38:
N-(2-(4-((1H-indol-3-yl)methyl)piperazin-1-yl)-5-(trifluoromethyl)phenyl)picolinamide
1H NMR (400 MHz, DMSO) δ 11.031 (s, 1H), 10.945 (s, 1H), 8.771-8.768 (d, J = 1.4 Hz, 1H), 8.270-8.260 (d, J = 4.4 Hz, 1H), 8.177-8.158 (d, J = 7.7 Hz, 1H), 8.115-8.092 (td, J = 7.7, 1.6 Hz, 1H), 7.715-7.695 (d, J = 7.9 Hz, 1H), 7.671-7.640 (ddd, J = 7.5, 4.8, 1.2 Hz, 1H), 7.453-7.403 (m, 3H), 7.320-7.316 (d, J = 1.8 Hz, 1H), 7.144-7.108 (t, J = 7.2 Hz, 1H), 7.035-7.017 (t, J = 7.1 Hz, 1H), 3.847 (s, 2H), 2.942 (s, 4H), 2.732 (s, 4H). MS (ESI-MS): m/z calcd for $C_{26}H_{24}F_3N_5O$ [MH]$^+$ 480.20, found.

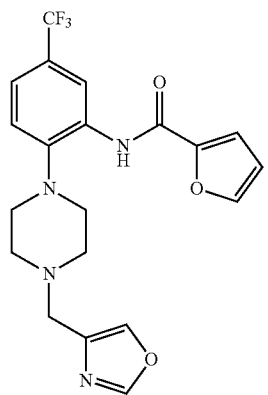 [SMILES: O=C(Nc1cc(C(F)(F)F)ccc1N1CCN(Cc2cocn2)CC1)c1ccco1]

Compound 39:
N-(2-(4-(oxazol-4-ylmethyl)piperazin-1-yl)-5-(trifluoro-methyl)-phenyl)furan-2-carboxamde
$^1$H NMR (400 MHz, CDCl$_3$) δ 9.44 (s, 1H), 8.51 (d, J = 1.6 Hz, 1H), 8.36 (s, 1H), 8.04 (s, 1H), 7.98 (d, J = 1.0 Hz, 1H), 7.47 (dt, J = 17.4, 5.1 Hz, 2H), 7.33 (d, J = 3.5 Hz, 1H), 6.77 (dd, J = 3.5, 1.7 Hz, 1H), 3.55 (s, 2H), 2.94 (m, 4H), 2.68 (m, 4H).
MS (ESI-MS): m/z calcd for $C_{20}H_{20}F_3N_4O_3$ [MH]$^+$ 420.14, found 421.13

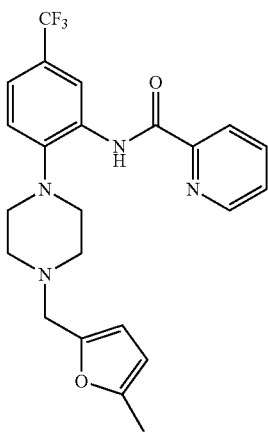 [SMILES: Cc1ccc(CN2CCN(c3ccc(C(F)(F)F)cc3NC(=O)c3ccccn3)CC2)o1]

Compound 40:
N-(2-(4-((5-methylfuran-2-yl)methyl)piperazin-1-yl)-5-(trifluoro-methyl)phenyl)picolinamide
$^1$H NMR (400 MHz, DMSO) δ 10.99 (s, 1H), 8.79 (s, 1H), 8.68 (d, J = 4.4 Hz, 1H), 8.20 (d, J = 7.7 Hz, 1H), 8.13 (t, J = 7.6 Hz, 1H), 7.74 (t, J = 4.8 Hz, 1H), 7.46 (q, J = 8.5 Hz, 2H), 6.23 (d, J = 2.8 Hz, 1H), 6.07 (s, 1H), 3.59 (s, 2H), 2.95 (m, 4H), 2.70 (m, 4H), 2.27 (s, 3H). MS (ESI-MS): m/z calcd for $C_{23}H_{24}F_3N_4O_2$ [MH]$^+$ 445.18, found 445.21.

TABLE 3-continued

Analytical data for synthesized compounds

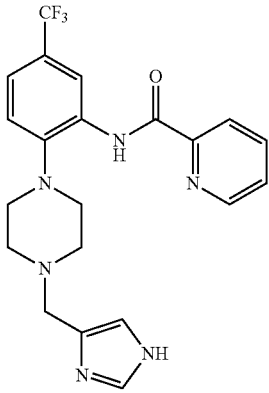 [SMILES: O=C(Nc1cc(C(F)(F)F)ccc1N1CCN(Cc2c[nH]cn2)CC1)c1ccccn1]

Compound 41:
N-(2-(4-(1H-imidazol-4-ylmethyl)piperazin-1-yl)-5-(trifluoromethyl)phenyl)-picolinamide
$^1$H NMR (400 MHz, DMSO) δ 10.97 (s, 1H), 8.79 (s, 1H), 8.70 (s, 1H), 8.20 (d, J = 7.0 Hz, 1H), 8.15 (d, J = 6.9 Hz, 1H), 7.76 (s, 2H), 7.45 (d, J = 9.8 Hz, 2H), 7.06 (s, 1H), 3.70 (s, 2H), 2.98 (m, 4H), 2.79 (m, 4H). MS (ESI-MS): m/z calcd for $C_{21}H_{21}F_3N_5OS$ $[MH]^+$ 431.17, found 431.20..

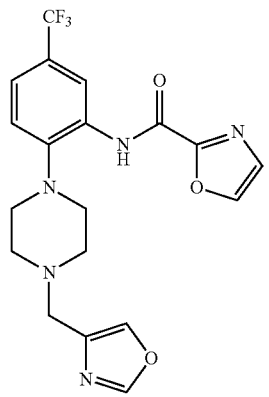 [SMILES: O=C(Nc1cc(C(F)(F)F)ccc1N1CCN(Cc2cocn2)CC1)c1ncco1]

Compound 42:
N-(2-(4-(oxazol-4-ylmethyl)piperazin-1-yl)-5-(trifluoromethyl)phenyl)oxazole-2-carboxamide
$^1$H NMR (400 MHz, DMSO) δ 9.94 (s, 1H), 8.56 (d, J = 1.5 Hz, 1H), 8.49 (d, J = 0.7 Hz, 1H), 8.36 (d, J = 0.8 Hz, 1H), 8.05 (d, J = 0.8 Hz, 1H), 7.60 (d, J = 0.6 Hz, 1H), 7.52 (dd, J = 8.4, 1.6 Hz, 1H), 7.51 (d, J = 8.4 Hz, 1H), 3.53 (s, 2H), 2.96-2.94 (m, 4H), 2.68 (s, 4H).
MS (ESI-MS): m/z calcd for $C_{19}H_{19}F_3N_5O_3$ $[MH]^+$ 422.14, found 422.19.

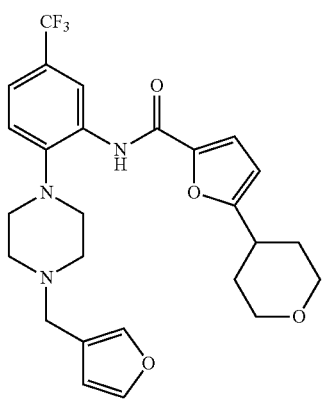 [SMILES: O=C(Nc1cc(C(F)(F)F)ccc1N1CCN(Cc2ccoc2)CC1)c1ccc(C2CCOCC2)o1]

Compound 43:
N-(2-(4-(furan-3-ylmethyl)piperazin-1-yl)-5-(trifluoromethyl)phenyl)-5-(tetrahydro-2H-pyran-4-yl)furan-2-carboxamide
$^1$H NMR (400 MHz, DMSO) δ 9.48 (s, 1H), 8.63 (s, 1H), 7.62 (m, 2H), 7.48- (q, J = 8.5 Hz, 2H), 7.24 (d, J = 3.4 Hz, 1H), 6.47 (d, J = 3.2 Hz, 2H), 3.99 (d, J = 9.7 Hz, 2H), 3.52 (dd, J = 11.6, 9.8 Hz, 2H), 3.48 (s, 2H), 3.08 (m, 1H), 2.94 (d, J= 4.3 Hz, 4H), 2.64 (m, 4H) 1.96 (d, J = 4.3 Hz, 2H) 1.833-1.742 (m, 2H).
MS (ESI-MS): m/z calcd for $C_{26}H_{29}F_3N_3O_4$ $[MH]^+$ 504.20, found 504.25

TABLE 3-continued

Analytical data for synthesized compounds

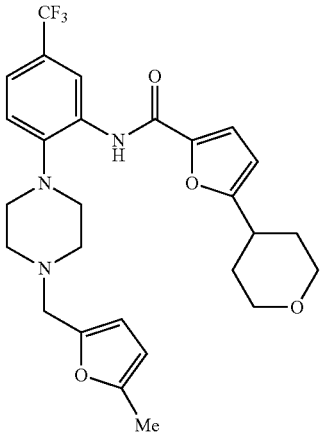 [SMILES: Cc1ccc(CN2CCN(c3ccc(C(F)(F)F)cc3NC(=O)c3ccc(C4CCOCC4)o3)CC2)o1]

Compound 44:
N-(2-(4-((5-methylfuran-2-yl)methyl)piperazin-1-yl)-5-(trifluoromethyl)phenyl)-5-(tetrahydro-2H-pyran-4-yl)furan-2-carboxamide
$^1$H NMR (400 MHz, DMSO) δ 9.47 (s, 1H), 8.62 (s, 1H) 7.49 (m, 2H), 7.25 (d, J = 3.2 Hz, 1H), 6.47 (d, J = 3.2 Hz, 1H), 6.17 (d, J = 2.8 Hz, 1H), 6.01 (s, 1H), 3.99 (d, J = 10 Hz, 2H), 3.51 (m, 4H), 3.10 (m, 1H), 2.94 (m, 4H), 2.65 (m, 4H), 2.25 (s, 3H) 1.97 (m, 2H). MS (ESI-MS): m/z calcd for $C_{26}H_{29}F_3N_3O_4$ [MH]$^+$ 518.20, found 518.26.

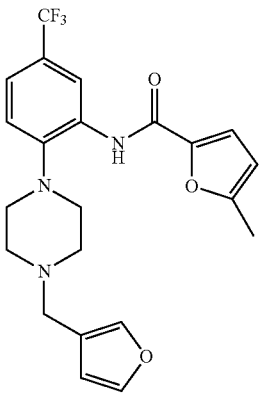 [SMILES: Cc1ccc(C(=O)Nc2cc(C(F)(F)F)ccc2N2CCN(Cc3ccoc3)CC2)o1]

Compound 45:
N-(2-(4-(furan-3-ylmethyl)piperazin-1-yl)-5-(trifluoromethyl)phenyl)-5-methylfuran-2-carboxamide
1H NMR (400 MHz, DMSO) δ 9.40 (s, 1H), 8.58 (s, 1H), 7.63 (m, 2H), 7.46 (d, J = 1.0 Hz, 2H), 7.21 (d, J = 3.3 Hz, 1H), 6.47 (m, 1H), 6.41 (dd, J = 3.3, 0.8 Hz, 1H), 3.47 (s, 2H), 2.94 (m, 4H), 2.63 (m, 4H), 2.40 (s, 3H). MS (ESI-MS): m/z calcd for $C_{22}H_{23}F_3N_3O_3$ [MH]$^+$ 434.16, found 434.17.

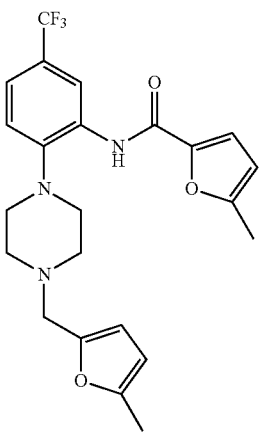 [SMILES: Cc1ccc(CN2CCN(c3ccc(C(F)(F)F)cc3NC(=O)c3ccc(C)o3)CC2)o1]

Compound 46:
5-methyl-N-(2-(4-((5-methylfuran-2-yl)methyl)piperazin-1-yl)-5-(trifluoromethyl)phenyl)furan-2-carboxamide
1H NMR (400 MHz, DMSO) δ 9.38 (s, 1H), 8.57 (s, 1H), 7.45 (m, 2H), 7.21 (d, J = 3.3 Hz, 1H), 6.40 (d, J = 2.6 Hz, 1H), 6.20 (d, J = 2.9 Hz, 1H), 6.01 (d, J = 1.9 Hz, 1H), 3.55 (s, 2H), 2.93 (m, 4H), 2.65 (m, 4H), 2.40 (s, 3H), 2.25 (s, 3H).
MS (ESI-MS): m/z calcd for $C_{23}H_{25}F_3N_3O_3$ [MH]$^+$ 448.18, found 448.21.

TABLE 3-continued

Analytical data for synthesized compounds

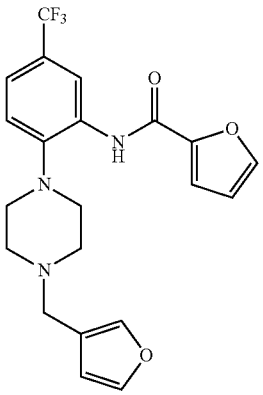 [SMILES: O=C(Nc1cc(C(F)(F)F)ccc1N1CCN(Cc2ccoc2)CC1)c1ccco1]

Compound 47:
N-(2-(4-(furan-3-ylmethyl)piperazin-1-yl)-5-(trifluoromethyl)phenyl)furan-2-carboxamide
$^1$H NMR (400 MHz, DMSO) δ 9.44 (s, 1H), 8.51 (d, J = 1.2 Hz, 1H), 7.98 (d, J = 0.9 Hz, 1H), 7.65 (d, J = 12.4 Hz, 2H), 7.46 (dd, J = 10, 8.4 Hz, 2H), 7.33 (d, J = 3.5 Hz, 1H), 6.78 (dd, J = 3.5, 1.7 Hz, 1H), 6.48 (s, 1H), 3.46 (s, 2H), 2.94 (m, 4H), 2.62 (m, 4H). MS (ESI-MS): m/z calcd for $C_{21}H_{21}F_3N_3O_3$ [MH]$^+$ 420.15, found 420.20.

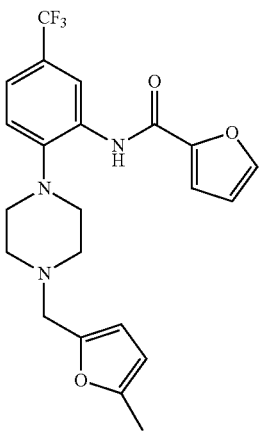 [SMILES: Cc1ccc(CN2CCN(c3ccc(C(F)(F)F)cc3NC(=O)c3ccco3)CC2)o1]

Compound 48:
N-(2-(4-((5-methylfuran-2-yl)methyl)piperazin-1-yl)-5-(trifluoromethyl)phenyl)furan-2-carboxamide
$^1$H NMR (400 MHz, DMSO) δ 9.44 (s, 1H), 8.51 (d, J = 1.6 Hz, 1H), 7.96 (d, J = 0.8 Hz, 1H), 7.46 (m, 2H), 7.33 (dd, J = 3.6, 0.8 Hz, 1H), 6.78 (dd, J = 3.6, 1.6 Hz, 1H), 6.20 (d, J = 2.8 Hz, 1H), 6.03 (m, 1H), 3.54 (s, 2H), 2.93 (m, 4H), 2.63 (m, 4H), 2.26 (s, 3H). MS (ESI-MS): m/z calcd for $C_{22}H_{23}F_3N_3O_3$ [MH]$^+$ 434.16, found 434.14.

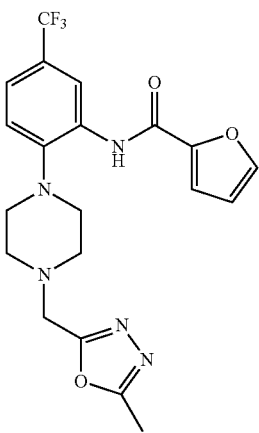 [SMILES: Cc1nnc(CN2CCN(c3ccc(C(F)(F)F)cc3NC(=O)c3ccco3)CC2)o1]

Compound 49:
N-(2-(4-((5-methyl-1,3,4-oxadiazol-2-yl)methyl)piperazin-1-yl)-5-(trifluoromethyl)phenyl)furan-2-carboxamide
1H NMR (400 MHz, DMSO) δ 9.46 (s, 1H), 8.50 (d, J = 4.0 Hz, 1H), 7.97 (d, J = 0.8 Hz, 1H), 7.47 (m, 2H), 7.34 (d, J = 3.6 Hz, 1H), 6.78 (dd, J = 3.2, 1.6 Hz, 1H), 3.89 (s, 2H), 2.96 (m, 4H), 2.74 (m, 4H), 2.52 (s, 3H)
MS (ESI-MS): m/z calcd for $C_{20}H_{21}F_3N_5O_3$ [MH]$^+$ 436.15, found 436.17.

TABLE 3-continued

Analytical data for synthesized compounds

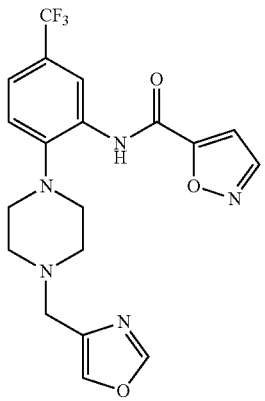 [SMILES: O=C(Nc1cc(C(F)(F)F)ccc1N1CCN(Cc2cocn2)CC1)c1ccno1]

Compound 50:
N-(2-(4-(oxazol-4-ylmethyl)piperazin-1-yl)-5-(trifluoro-methyl)phenyl)isoxazole-5-carboxamide
$^1$H NMR (400 MHz, DMSO) δ 9.88 (s, 1H), 8.88 (d, J = 1.9 Hz, 1H), 8.33 (d, J = 0.8 Hz, 1H), 8.29 (s, 1H), 8.03 (s, 1H), 7.56 (dd, J = 8.6, 1.8 Hz, 1H), 7.42 (d, J = 8.4 Hz, 1H), 7.30 (s, 1H), 3.50 (s, 2H), 2.96 (m, 4H), 2.64 (m, 4H).
MS (ESI-MS): m/z calcd for $C_{19}H_{19}F_3N_5O_3$ [MH]$^+$ 422.14, found 422.22.

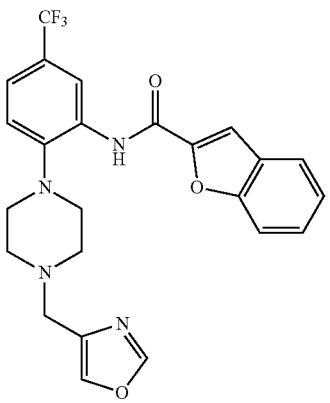 [SMILES: O=C(Nc1cc(C(F)(F)F)ccc1N1CCN(Cc2cocn2)CC1)c1cc2ccccc2o1]

Compound 51:
N-(2-(4-(oxazol-4-ylmethyl)piperazin-1-yl)-5-(trifluoro-methyl)-phenyl)benzofuran-2-carboxamide
$^1$H NMR (400 MHz, DMSO) δ 9.74 (s, 1H), 8.57 (d, J = 1.6 Hz, 1H), 8.42 (d, J = 21.4 Hz, 1H), 8.09 (d, J = 15.3 Hz, 1H), 7.85 (d, J = 7.8 Hz, 1H), 7.77 (s, 1H), 7.65 (d, J = 8.3 Hz, 1H), 7.63-7.56 (m, 1H), 7.55-7.45 (m, 2H), 7.42 (dd, J = 10.9, 4.0 Hz, 1H), 3.62 (s, 2H), 3.09-2.87 (m, 4H), 2.74 (m, 4H).
MS (ESI-MS): m/z calcd for $C_{24}H_{22}F_3N_4O_3$ [MH]$^+$ 471.15, found 471.2

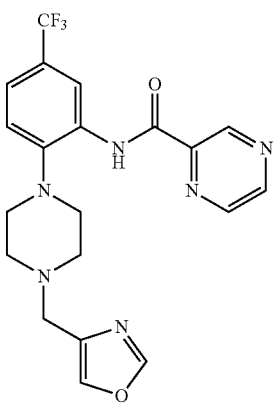 [SMILES: O=C(Nc1cc(C(F)(F)F)ccc1N1CCN(Cc2cocn2)CC1)c1cnccn1]

Compound 52:
N-(2-(4-(oxazol-4-ylmethyl)piperazin-1-yl)-5-(trifluoro-methyl)phenyl)pyrazine-2-carboxamide
$^1$H NMR (400 MHz, DMSO) δ 10.68 (s, 1H), 9.34 (d, J = 1.3 Hz, 1H), 9.00 (d, J = 2.4 Hz, 1H), 8.79 (dd, J = 2, 1.6 Hz, 1H), 8.74 (d, J = 1.5 Hz, 1H), 8.39 (s, 1H), 8.06 (s, 1H), 7.46 (m, 2H), 3.58 (s, 2H), 2.93 (m, 4H), 2.71 (m, 4H).
MS (ESI-MS): m/z calcd for $C_{20}H_{20}F_3N_6O_2$ [MH]$^+$ 433.15, found 433.19.

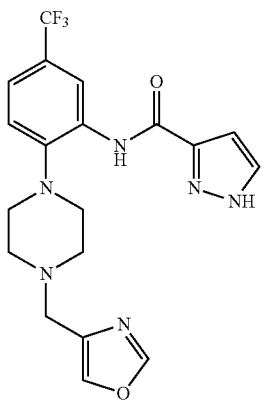 [SMILES: O=C(Nc1cc(C(F)(F)F)ccc1N1CCN(Cc2cocn2)CC1)c1cc[nH]n1]

Compound 53:
N-(2-(4-(oxazol-4-ylmethyl)piperazin-1-yl)-5-(trifluoro-methyl)phenyl)-1H-pyrazole-3-carboxamide
$^1$H NMR (400 MHz, DMSO) δ 13.60 (s, 1H) 9.70 (s, 1H), 8.61 (m, 2H), 8.32 (s, 1H), 7.99 (s, 1H), 7.46 (m, 2H), 6.84 (s, 1H), 4.32 (s, 2H) 3.35 (m, 4H) 3.17 (m, 4H)
MS (ESI-MS): m/z calcd for $C_{19}H_{20}F_3N_6O_2$ [MH]$^+$ 421.15, found 421.31.

TABLE 3-continued

Analytical data for synthesized compounds

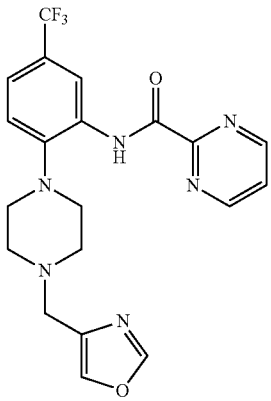 [SMILES: O=C(Nc1cc(C(F)(F)F)ccc1N1CCN(Cc2cocn2)CC1)c1ncccn1]

Compound 54:
N-(2-(4-(oxazol-4-ylmethyl)piperazin-1-yl)-5-(trifluoro-methyl)phenyl)pyrimidine-2-carboxamide
$^1$H NMR (400 MHz, DMSO) δ 10.82 (s, 1H), 9.09 (d, J = 4.6 Hz, 2H), 8.66 (m, 2H), 8.38 (s, 1H), 7.83 (s, 1H), 7.65-7.40 (m, 2H), 6.63 (s, 2H), 4.45 (s, 2H), 3.25 (m, 8H).
MS (ESI-MS): m/z calcd for $C_{20}H_{20}F_3N_6O_2$ [MH]$^+$ 433.17, found 433.32.

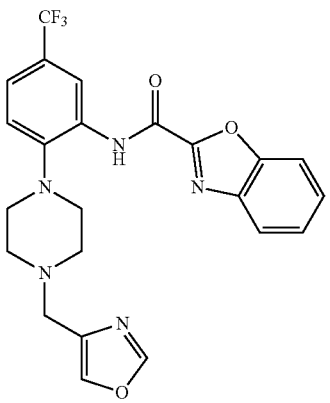 [SMILES: O=C(Nc1cc(C(F)(F)F)ccc1N1CCN(Cc2cocn2)CC1)c1nc2ccccc2o1]

Compound 55:
N-(2-(4-(oxazol-4-ylmethyl)piperazin-1-yl)-5-(trifluoro-methyl)phenyl)benzo[d]oxazole-2-carboxamide
$^1$H NMR (400 MHz, DMSO) δ 10.20 (s, 1H), 8.57 (s, 1H), 8.40 (s, 1H), 8.09 (s, 1H), 7.95 (d, J = 8.2 Hz, 2H), 7.61 (m, 3H), 7.49 (d, J = 8.3 Hz, 1H), 3.61 (s, 2H), 3.00 (m, 4H), 2.75 (m, 4H).
MS (ESI-MS): m/z calcd for $C_{23}H_{21}F_3N_5O_3$ [MH]$^+$ 472.16, found 472.21.

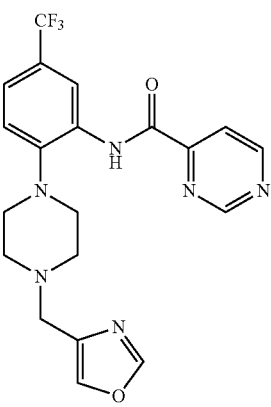 [SMILES: O=C(Nc1cc(C(F)(F)F)ccc1N1CCN(Cc2cocn2)CC1)c1ccncn1]

Compound 56:
N-(2-(4-(oxazol-4-ylmethyl)piperazin-1-yl)-5-(trifluoro-methyl)phenyl)pyrimidine-4-carboxamide
$^1$H NMR (400 MHz, DMSO) δ 10.86 (s, 1H), 9.39 (s, 1H), 9.20 (d, J = 4.9 Hz, 1H), 8.74 (s, 1H), 8.39 (s, 1H), 8.19 (d, J = 4.9 Hz, 1H), 8.08 (s, 1H), 7.50 (dd, J = 21.9, 8.4 Hz, 2H), 3.59 (s, 2H), 2.96 (m, 4H), 2.73 (m, 4H).
MS (ESI-MS): m/z calcd for $C_{20}H_{20}F_3N_6O_2$ [MH]$^+$ 433.41, found 433.23.

TABLE 3-continued

Analytical data for synthesized compounds

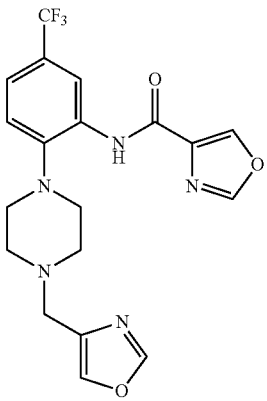 [SMILES: O=C(Nc1cc(C(F)(F)F)ccc1N1CCN(Cc2cocn2)CC1)c1cocn1]

Compound 57:
N-(2-(4-(oxazol-4-ylmethyl)piperazin-1-yl)-5-(trifluoro-methyl)phenyl)oxazole-4-carboxamide
$^1$H NMR (400 MHz, DMSO) δ 9.65 (s, 1H), 8.96 (s, 1H), 8.64 (d, J = 10.5 Hz, 3H), 8.40 (s, 1H), 7.68-7.42 (m, 2H), 3.57 (s, 2H), 3.28 (m, 8H).
MS (ESI-MS): m/z calcd for $C_{19}H_{19}F_3N_5O_3$ [MH]$^+$ 422.14, found 422.17.

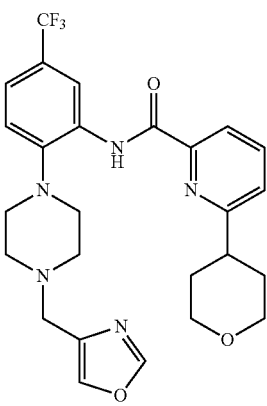 [SMILES: O=C(Nc1cc(C(F)(F)F)ccc1N1CCN(Cc2cocn2)CC1)c1cccc(C2CCOCC2)n1]

Compound 58:
N-(2-(4-(oxazol-4-ylmethyl)piperazin-1-yl)-5-(trifluoro-methyl)phenyl)-6-(tetrahydro-2H-pyran-4-yl)picolinamide
$^1$H NMR (400 MHz, DMSO) δ 10.85 (s, 1H), 8.85 (s, 1H), 8.32 (s, 1H), 8.02 (m, 3H), 7.65 (s, 1H), 7.48 (s, 2H), 4.05 (s, 2H), 3.53 (m, 4H), 3.16 (s, 1H), 2.92 (m, 4H), 2.74 (m, 4H), 1.93 (m, 4H).
MS (ESI-MS): m/z calcd for $C_{26}H_{29}F_3N_5O_3$ [MH]$^+$ 516.21, found 516.39.

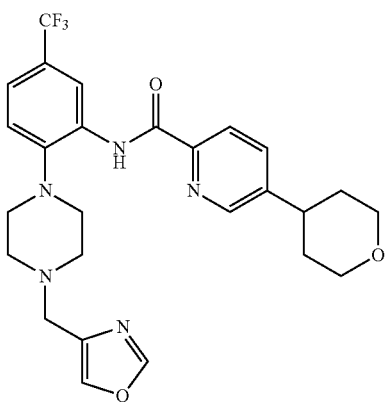 [SMILES: O=C(Nc1cc(C(F)(F)F)ccc1N1CCN(Cc2cocn2)CC1)c1ccc(C2CCOCC2)cn1]

Compound 59:
N-(2-(4-(oxazol-4-ylmethyl)piperazin-1-yl)-5-(trifluoro-methyl)phenyl)-5-(tetrahydro-2H-pyran-4-yl)picolinamide
$^1$H NMR (400 MHz, DMSO) δ 10.95 (s, 1H), 8.80 (s, 1H), 8.62 (s, 1H), 8.39 (s, 1H), 8.14 (d, J = 8.0 Hz, 1H), 8.08 (s, 1H), 8.02 (dd, J = 8.1, 2.0 Hz, 1H), 7.52-7.39 (m, 2H), 4.01 (d, J = 10.9 Hz, 2H), 3.61 (s, 2H), 3.56-3.41 (m, 2H), 3.02 (dd, J = 15.3, 7.6 Hz, 1H), 2.95 (m, 4H), 2.75 (m, 4H), 1.78 (dd, J = 10.4, 7.5 Hz, 4H).
MS (ESI-MS): m/z calcd for $C_{26}H_{29}F_3N_5O_3$ [MH]$^+$ 516.21, found 516.24.

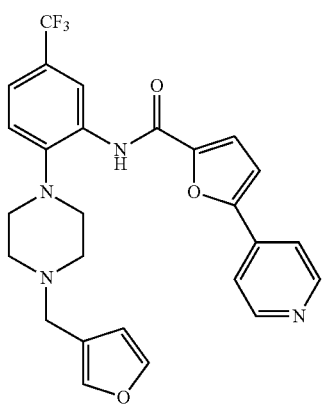 [SMILES: O=C(Nc1cc(C(F)(F)F)ccc1N1CCN(Cc2ccoc2)CC1)c1ccc(-c2ccncc2)o1]

Compound 60:
N-(2-(4-(furan-3-ylmethyl)piperazin-1-yl)-5-(trifluoro-methyl)phenyl)-5-(pyridin-4-yl)furan-2-carboxamide
$^1$H NMR (400 MHz, DMSO) δ 9.72 (s, 1H), 8.76 (d, J = 5.9 Hz, 2H), 8.52 (s, 1H), 7.98-7.84 (m, 2H), 7.70-7.42 (m, 6H), 6.43 (s, 1H), 3.40 (s, 2H), 2.98 (m, 4H), 2.65 (m, 4H).
MS (ESI-MS): m/z calcd for $C_{26}H_{24}F_3N_4O_3$ [MH]$^+$ 497.17, found 497.39

TABLE 3-continued

Analytical data for synthesized compounds

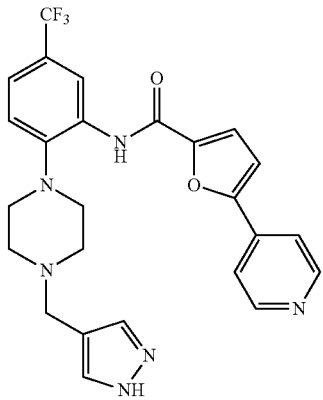 [SMILES: O=C(Nc1cc(C(F)(F)F)ccc1N1CCN(Cc2cn[nH]c2)CC1)c1ccc(-c2ccncc2)o1]

Compound 61:
N-(2-(4-((1H-pyrazol-4-yl)methyl)piperazin-1-yl)-5-(trifluoro-methyl)phenyl)-5-(pyridin-4-yl)furan-2-carboxamide
$^1$H NMR (400 MHz, CDCl$_3$) δ 9.65 (s, 1H), 8.88 (s, 1H), 8.77 (d, J = 6.0 Hz, 2H), 7.73 (d, J = 6.1 Hz, 2H), 7.65 (s, 1H), 7.55 (s, 2H), 7.42 (d, J = 3.7 Hz, 2H), 7.36 (s, 1H), 7.09 (d, J = 3.7 Hz, 1H), 4.68 (s, 1H), 3.60 (s, 2H), 3.04 (m, 4H), 2.77 (m, 4H).
MS (ESI-MS): m/z calcd for C$_{25}$H$_{24}$F$_3$N$_6$O$_2$ [MH]$^+$ 497.18, found 497.44

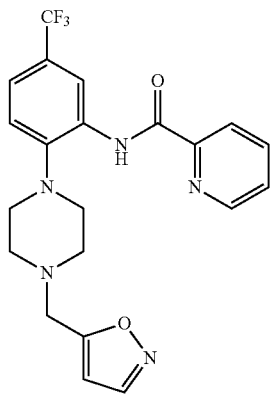 [SMILES: O=C(Nc1cc(C(F)(F)F)ccc1N1CCN(Cc2ccno2)CC1)c1ccccn1]

Compound 62:
N-(2-(4-(isoxazol-5-ylmethyl)piperazin-1-yl)-5-(trifluoro-methyl)phenyl)picolinamide
$^1$H NMR (400 MHz, DMSO) δ 10.97 (s, 1H), 8.79 (d, J = 1.7 Hz, 1H), 8.69 (d, J = 4.1 Hz, 1H), 8.61 (d, J = 1.7 Hz, 1H), 8.20 (d, J = 7.7 Hz, 1H), 8.13 (m, 1H), 7.75 (ddd, J = 7.5, 4.7, 1.2 Hz, 1H), 7.59-7.41 (m, 2H), 6.51 (d, J = 1.7 Hz, 1H), 3.92 (s, 2H), 2.97 (m, 4H), 2.76 (m, 4H).
MS (ESI-MS): m/z calcd for C$_{21}$H$_{21}$F$_3$N$_5$O$_2$ [MH]$^+$ 432.15, found 432.23

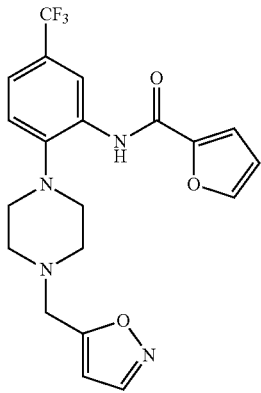 [SMILES: O=C(Nc1cc(C(F)(F)F)ccc1N1CCN(Cc2ccno2)CC1)c1ccco1]

Compound 63:
N-(2-(4-(isoxazol-5-ylmethyl)piperazin-1-yl)-5-(trifluoro-methyl)phenyl)furan-2-carboxamide
$^1$H NMR (400 MHz, DMSO) δ 9.45 (s, 1H), 8.58 (d, J = 1.7 Hz, 1H), 8.50 (d, J = 1.6 Hz, 1H), 7.95 (d, J = 1.0 Hz, 1H), 7.57-7.42 (m, 2H), 7.33 (d, J = 3.5 Hz, 1H), 6.78 (dd, J = 3.5, 1.7 Hz, 1H), 6.48 (d, J = 1.7 Hz, 1H), 3.87 (s, 2H), 2.95 (m, 4H), 2.69 (m, 4H).
MS (ESI-MS): m/z calcd for C$_{20}$H$_{20}$F$_3$N$_4$O$_3$ [MH]$^+$ 421.14, found 421.36.

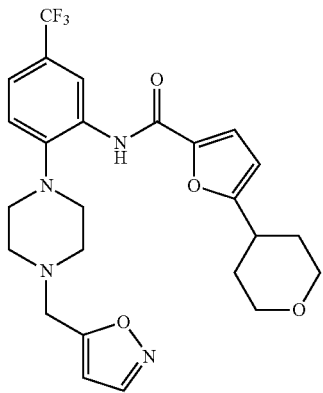 [SMILES: O=C(Nc1cc(C(F)(F)F)ccc1N1CCN(Cc2ccno2)CC1)c1ccc(C2CCOCC2)o1]

Compound 64:
N-(2-(4-(isoxazol-5-ylmethyl)piperazin-1-yl)-5-(trifluoro-methyl)phenyl)-5-(tetrahydro-2H-pyran-4-yl)furan-2-carboxamide
$^1$H NMR (400 MHz, DMSO) δ 9.44 (s, 1H), 8.58 (d, J = 18.6 Hz, 2H), 7.54-7.44 (m, 2H), 7.25 (d, J = 3.5 Hz, 1H), 6.47 (d, J = 2.9 Hz, 2H), 3.98 (d, J = 9.6 Hz, 2H), 3.80 (s, 2H), 3.52 (dd, J = 11.6, 9.6 Hz, 2H), 3.35 (m, 4H), 3.14-3.04 (m, 1H), 2.69 (m, 4H), 1.95 (d, J = 10.8 Hz, 2H), 1.80-1.72 (m, 2H).
MS (ESI-MS): m/z calcd for C$_{25}$H$_{28}$F$_3$N$_4$O$_4$ [MH]$^+$ 505.19, found 505.3.

TABLE 3-continued

Analytical data for synthesized compounds

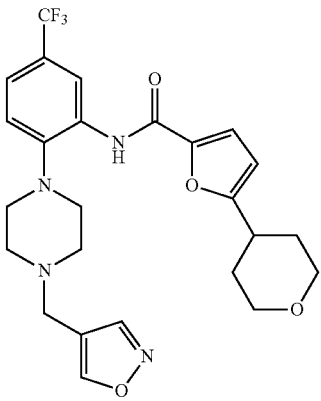 [SMILES: O=C(Nc1cc(C(F)(F)F)ccc1N1CCN(Cc2cnoc2)CC1)c1ccc(C2CCOCC2)o1]

Compound 65:
N-(2-(4-(isoxazol-4-ylmethyl)piperazin-1-yl)-5-(trifluoromethyl)phenyl)-5-(tetrahydro-2H-pyran-4-yl)furan-2-carboxamid
$^1$H NMR (400 MHz, CDCl$_3$) δ 9.43 (s, 1H), 8.88 (s, 1H), 8.46 (s, 1H), 7.36 (t, J = 9.2 Hz, 2H), 7.28 (s, 1H), 7.20 (d, J = 3.4 Hz, 1H), 6.28 (d, J = 3.4 Hz, 1H), 4.15 (d, J = 11.4 Hz, 2H), 3.77-3.52 (m, 3H), 3.06 (m, 4H), 1.99 (dt, J = 13.9, 6.8 Hz, 4H), 1.68 (s, 2H), 1.27 (s, 2H).
MS (ESI-MS): m/z calcd for C$_{25}$H$_{28}$F$_3$N$_4$O$_4$ [MH]$^+$ 505.19, found 505.35.

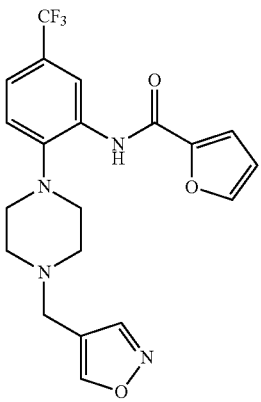 [SMILES: O=C(Nc1cc(C(F)(F)F)ccc1N1CCN(Cc2cnoc2)CC1)c1ccco1]

Compound 66:
N-(2-(4-(isoxazol-4-ylmethyl)piperazin-1-yl)-5-(trifluoromethyl)phenyl)furan-2-carboxamide
$^1$H NMR (400 MHz, DMSO) δ 9.45 (s, 1H), 8.92 (s, 1H), 8.62 (s, 1H), 8.50 (d, J = 1.8 Hz, 1H), 7.96 (dd, J = 1.7, 0.7 Hz, 1H), 7.47 (m, 2H), 7.34 (dd, J = 3.5, 0.7 Hz, 1H), 6.78 (dd, J = 3.5, 1.7 Hz, 1H), 3.54 (s, 2H), 2.94 (m, 4H), 2.61 (m, 4H).
MS (ESI-MS): m/z calcd for C$_{20}$H$_{20}$F$_3$N$_4$O$_3$ [MH]$^+$ 421.15, found 421.31.

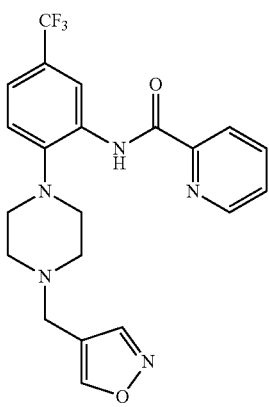 [SMILES: O=C(Nc1cc(C(F)(F)F)ccc1N1CCN(Cc2cnoc2)CC1)c1ccccn1]

Compound 67:
N-(2-(4-(isoxazol-4-ylmethyl)piperazin-1-yl)-5-(trifluoromethyl)phenyl)-picolinamide
$^1$H NMR (400 MHz, DMSO) δ 10.97 (s, 1H), 8.95 (s, 1H), 8.80 (d, J = 1.8 Hz, 1H), 8.67 (d, J = 4.7 Hz, 1H), 8.65 (s, 1H), 8.21 (d, J = 7.7 Hz, 1H), 8.13 (td, J = 7.7, 1.6 Hz, 1H), 7.75 (ddd, J = 7.5, 4.7, 1.3 Hz, 1H), 7.53-7.43 (m, 2H), 3.60 (s, 2H), 2.96 (m, 4H), 2.67 (m, 4H).
MS (ESI-MS): m/z calcd for C$_{21}$H$_{21}$F$_3$N$_5$O$_2$ [MH]$^+$ 432.16, found 432.32

TABLE 3-continued

Analytical data for synthesized compounds

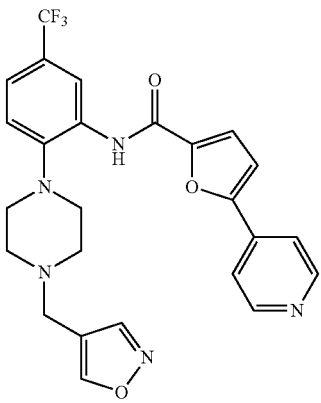

Compound 68:
N-(2-(4-(isoxazol-4-ylmethyl)piperazin-1-yl)-5-(trifluoromethyl)phenyl)-5-(pyridin-4-yl)furan-2-carboxamide
$^1$H NMR (400 MHz, DMSO) δ 9.73 (s, 1H), 8.89 (s, 1H), 8.77 (d, J = 6.1 Hz, 2H), 8.58 (s, 1H), 8.51 (d, J = 1.5 Hz, 1H), 7.90 (d, J = 6.1 Hz, 2H), 7.57 (d, J = 3.7 Hz, 1H), 7.50 (d, J = 3.7 Hz, 3H), 3.48 (s, 2H), 3.08-2.81 (m, 4H), 2.66 (m, 4H).
MS (ESI-MS): m/z calcd for $C_{25}H_{23}F_3N_5O_3$ [MH]$^+$ 498.16, found 498.34

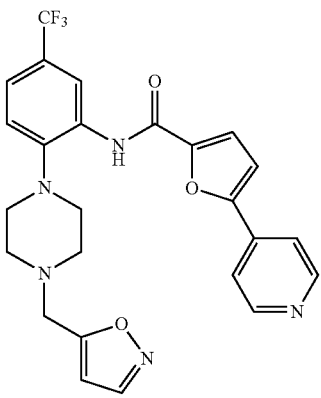 [SMILES: O=C(Nc1cc(C(F)(F)F)ccc1N1CCN(Cc2ccno2)CC1)c1ccc(-c2ccncc2)o1]

Compound 69:
N-(2-(4-(isoxazol-5-ylmethyl)piperazin-1-yl)-5-(trifluoromethyl)phenyl)-5-(pyridin-4-yl)furan-2-carboxamide
$^1$H NMR (400 MHz, DMSO) δ 9.72 (s, 1H), 8.77 (d, J = 5.8 Hz, 2H), 8.57-8.47 (m, 2H), 7.90 (d, J = 6.0 Hz, 2H), 7.65-7.46 (m, 4H), 6.43 (d, J = 1.6 Hz, 1H), 3.78 (s, 2H), 3.00 (m, 4H), 2.72 (m, 4H).
MS (ESI-MS): m/z calcd for $C_{25}H_{23}F_3N_5O_3$ [MH]$^+$ 498.16, found 498.29

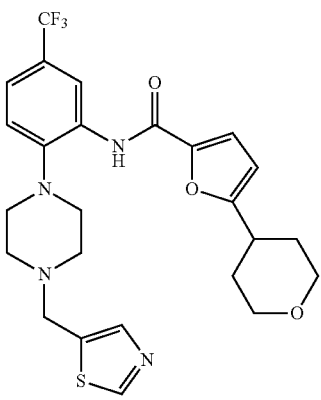 [SMILES: O=C(Nc1cc(C(F)(F)F)ccc1N1CCN(Cc2cncs2)CC1)c1ccc(C2CCOCC2)o1]

Compound 70:
5-(tetrahydro-2H-pyran-4-yl)-N-(2-(4-(thiazol-5-ylmethyl)piperazin-1-yl)-5-(trifluoromethyl)phenyl)furan-2-carboxamide
$^1$H NMR (400 MHz, DMSO) δ 9.43 (s, 1H), 8.83 (m, 2H), 7.79 (s, 1H), 7.36-7.18 (m, 3H), 6.25 (d, J = 3.2 Hz, 1H), 4.16 (m, 2H), 3.87 (s, 2H), 3.64-3.58 (m, 2H), 3.07-3.00 (m, 4H), 2.01-1.94 (m, 4H), 1.26 (m, 1H).
MS (ESI-MS): m/z calcd for $C_{25}H_{28}F_3N_4O_3S$ [MH]$^+$ 521.18, found 521.22

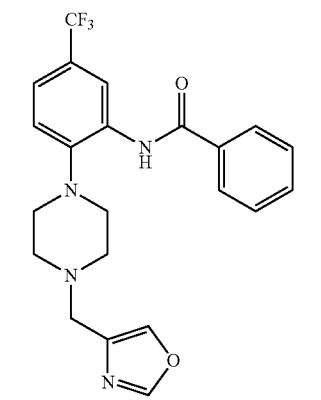 [SMILES: O=C(Nc1cc(C(F)(F)F)ccc1N1CCN(Cc2cocn2)CC1)c1ccccc1]

Compound 71:
N-(2-(4-(oxazol-4-ylmethyl)piperazin-1-yl)-5-(trifluoromethyl)phenyl)benzamide
$^1$H NMR (400 MHz, DMSO) δ 9.64 (s, 1H), 8.38-8.35 (m, 2H), 8.02 (s, 1H), 7.96-7.94 (m, 2H), 7.66-7.64 (m, 1H), 7.59-7.56 (m, 2H), 7.52-7.50 (m, 1H), 7.42-7.40 (m, 1H), 3.51 (s, 2H), 2.95 (m, 4H), 2.63 (m, 4H).
MS (ESI-MS): m/z calcd for $C_{22}H_{22}F_3N_4O_2$ [MH]$^+$ 431.16, found 431.23

TABLE 3-continued

Analytical data for synthesized compounds

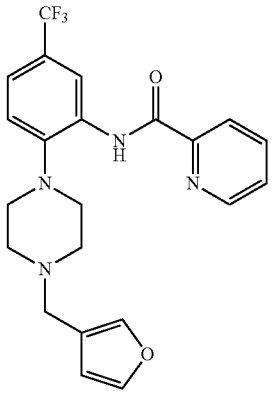 [SMILES: O=C(Nc1cc(C(F)(F)F)ccc1N1CCN(Cc2ccoc2)CC1)c1ccccn1]

Compound 72:
N-(2-(4-(furan-3-ylmethyl)piperazin-1-yl)-5-(trifluoromethyl)phenyl)picolinamide
$^1$H NMR (400 MHz, DMSO) δ 10.98 (s, 1H), 8.79 (s, 1H), 8.70 (d, J = 4.3 Hz, 1H), 8.19 (d, J = 7.7 Hz, 1H), 8.12 (m, 1H), 7.75 (m, 1H), 7.67 (d, J = 11.1 Hz, 2H), 7.46 (m, 2H), 6.50 (s, 1H), 3.50 (s, 2H), 2.96 (m, 4H), 2.68 (m, 4H).
MS (ESI-MS): m/z calcd for $C_{22}H_{22}F_3N_4O_2$ [MH]$^+$ 431.16, found 431.20

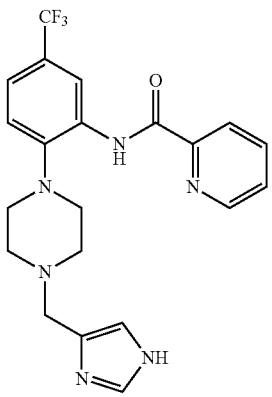 [SMILES: O=C(Nc1cc(C(F)(F)F)ccc1N1CCN(Cc2c[nH]cn2)CC1)c1ccccn1]

Compound 73:
N-(2-(4-(1H-imidazol-4-ylmethyl)piperazin-1-yl)-5-(trifluoromethyl)phenyl)picolinamide
1H NMR (400 MHz, DMSO) δ 10.97 (s, 1H), 8.79 (s, 1H), 8.70 (s, 1H), 8.20 (d, J = 7.0 Hz, 1H), 8.14 (d, J = 6.9 Hz, 1H), 7.76 (m, 2H), 7.45 (d, J = 9.8 Hz, 2H), 7.06 (s, 1H), 3.70 (s, 2H), 2.98 (m, 4H), 2.79 (m, 4H).
MS (ESI-MS): m/z calcd for $C_{21}H_{21}F_3N_6O$ [MH]$^+$ 431.17, found 431.20.

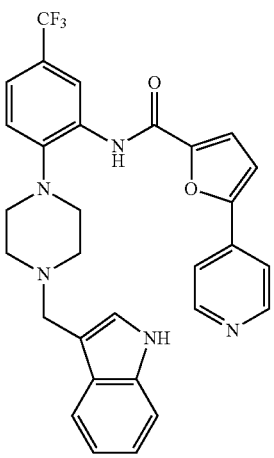 [SMILES: O=C(Nc1cc(C(F)(F)F)ccc1N1CCN(Cc2c[nH]c3ccccc23)CC1)c1ccc(-c2ccncc2)o1]

Compound 74:
N-(2-(4-((1H-indol-3-yl)methyl)piperazin-1-yl)-5-(trifluoromethyl)-phenyl)-5-(pyridin-4-yl)furan-2-carboxamide
$^1$H NMR (300 MHz; CDCl$_3$) δ 2.82 (br s, 4H), 2.97 (t, J = 4.6 Hz, 4H), 3.82 (s, 2H), 7.06 (d, J = 3.7 Hz, 1H), 7.08-7.13 (m, 2H), 7.17-7.23 (m, 1H), 7.30 (d, J = 8.2 Hz, 1H), 7.35-7.40 (m ,3H), 7.72 (d, J = 8.0 Hz, 1H), 7.75-7.77 (m, 2H), 8.30 (s, 1H), 8.78-8.80 (m, 2H), 8.86 (d, J = 1.8 Hz, 1H), 9.68 (s, 1H)
HRMS (ESI-MS): m/z calcd for $C_{30}H_{27}F_3N_5O_2$ (M$^+$ + H) 546.2117, found 546.2101

TABLE 3-continued

Analytical data for synthesized compounds

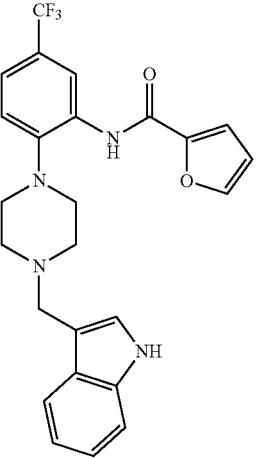 [SMILES: O=C(Nc1cc(C(F)(F)F)ccc1N1CCN(Cc2c[nH]c3ccccc23)CC1)c1ccco1]

Compound 75:
N-(2-(4-((1H-indol-3-yl)methyl)piperazin-1-yl)-5-(trifluoromethyl)phenyl)furan-2-carboxamide
1H NMR (400 MHz, DMSO) δ 10.98 (s, 1H), 9.41 (s, 1H), 8.52 (s, 1H), 7.79 (d, J = 0.9 Hz, 1H), 7.69 (d, J = 7.8 Hz, 1H), 7.45 (m, 2H), 7.37 (d, J = 8.0 Hz, 1H), 7.30 (m, 2H), 7.09 (m, 1H), 7.01 (m, 1H), 6.76 (m, 1H), 3.78 (s, 2H), 2.92 (m, 4H), 2.67 (m, 4H).
MS (ESI-MS): m/z calcd for $C_{25}H_{23}F_3N_4O_2Na$ [M − Na]+ 491.17, found 491.20

REFERENCES

Bressler, S., Bressler, N. M., Clemons, T., Ferris, F. L., Milton, R. C., Klien, R., Klien, B. and Age-Related Eye Dis Study, G. (2004) 'Ocular risk factors for developing neovascular AMD in the fellow eyes of patients with unilateral neovascular AMD', Investigative Ophthalmology & Visual Science, 45, U924-U924.

Ferris, F. L., Fine, S. L. and Hyman, L. (1984) 'Age-related macular degeneration and blindness due to neovascular maculopathy', Archives of Ophthalmology, 102(11), 1640-1642.

Patz, A., Fine, S. L., Finkelstein, D. and Yassur, Y. (1977) 'Diseases of macula—diagnosis and management of choroidal neovascularization', Transactions American Academy of Ophthalmology and Otolaryngology, 83(3), 468-475.

Fine, S. L., Berger, J. W., Maguire, M. G. and Ho, A. C. (2000) 'Drug therapy: Age-related macular degeneration', New England Journal of Medicine, 342(7), 483-492.

Campochiaro, P. A., Nguyen, Q. D., Shah, S. M., Klein, M. L., Holz, E., Frank, R. N., Saperstein, D. A., Gupta, A., Stout, J. T., Macko, J., DiBartolomeo, R. and Wei, L. L. (2006) 'Adenoviral vector-delivered pigment epithelium-derived factor for neovascular age-related macular degeneration: Results of a phase I clinical trial', Human Gene Therapy, 17(2), 167-176.

Dvorak, H. F., Brown, L. F., Detmar, M. and Dvorak, A. M. (1995) 'Vascular-permeability factor vascular endothelial growth-factor, microvascular hyperpermeability, and angiogenesis', American Journal of Pathology, 146(5), 1029-1039.

D'Amore, P. A., Shima, D. T., Adamis, A. P., Yeo, K. T., Yeo, T. K., Allende, R. and Folkman, J. (1994) 'differential regulation of VEGF/VPF and basic FGF by hypoxia', Faseb Journal, 8(4), A116-A116.

Spilsbury, K., Garrett, K. L., Shen, W. Y., Constable, I. J. and Rakoczy, P. E. (2000) 'Overexpression of vascular endothelial growth factor (VEGF) in the retinal pigment epithelium leads to the development of choroidal neovascularization', American Journal of Pathology, 157(1), 135-144.

Anderson, D. H., Mullins, R. F., Hageman, G. S. and Johnson, L. V. (2002) 'Perspective—A role for local inflammation in the formation of drusen in the aging eye', American Journal of Ophthalmology, 134(3), 411-431.

Das, A., Fanslow, W., Cerretti, D., Warren, E., Talarico, N. and McGuire, P. (2003) 'Angiopoietin/Tek interactions regulate MMP-9 expression and retinal neovascularization', Laboratory Investigation, 83(11), 1637-1645.

Leung, D. W., Cachianes, G., Kuang, W. J., Goeddel, D. V. and Ferrara, N. (1989) 'Vascular endothelial growth-factor is a secreted angiogenic mitogen', Science, 246 (4935), 1306-1309.

Jingjing, L., Xue, Y., Agarwal, N. and Roque, R. S. (1999) 'Human Muller cells express VEGF183, a novel spliced variant of vascular endothelial growth factor', Joys, 40(3), 752-759.

Houck, K. A., Ferrara, N., Winer, J., Cachianes, G., Li, B. and Leung, D. W. (1991) 'The vascular endothelial growth-factor family—identification of a 4th molecular-species and characterization of alternative splicing of rna', Molecular Endocrinology, 5(12), 1806-1814.

Mineur, P., Colige, A. C., Deroanne, C. F., Dubail, J., Kesteloot, F., Habraken, Y., Noel, A., Voo, S., Waltenberger, J., Lapiere, C. M., Nusgens, B. V. and Lambert, C. A. (2007) 'Newly identified biologically active and proteolysis-resistant VEGF-A isoform VEGF111 is induced by genotoxic agents', Journal of Cell Biology, 179(6), 1261-1273.

Tischer, E., Gospodarowicz, D., Mitchell, R., Silva, M., Schilling, J., Lau, K., Crisp, T., Fiddes, J. C. and Abraham, J. A. (1989) 'Vascular endothelial growth-factor—a new member of the platelet-derived growth-factor gene family', Biochemical and Biophysical Research Communications, 165(3), 1198-1206.

Neufeld, G., Cohen, T., Gengrinovitch, S. and Poltorak, Z. (1999) 'Vascular endothelial growth factor (VEGF) and its receptors', Faseb Journal, 13(1), 9-22.

Bates, D. O., Cui, T. G., Doughty, J. M., Winkler, M., Sugiono, M., Shields, J. D., Peat, D., Gillatt, D. and Harper, S. J. (2002) 'VEGF(165)b, an inhibitory splice variant of vascular endothelial growth factor, is down-regulated in renal cell carcinoma', Cancer Research, 62(14), 4123-4131.

Woolard, J., Wang, W. Y., Bevan, H. S., Qiu, Y., Morbidelli, L., Pritchard-Jones, R. O., Cui, T. G., Sugiono, M., Waine, E., Perrin, R., Foster, R., Digby-Bell, J., Shields, J. D., Whittles, C. E., Mushens, R. E., Gillatt, D. A., Ziche, M., Harper, S. J. and Bates, D. O. (2004) 'VEGF(165)b, an inhibitory vascular endothelial growth factor splice variant: Mechanism of action, in vivo effect on angiogenesis and endogenous protein expression', *Cancer Research*, 64(21), 7822-7835.

Perrin, R. M., Konopatskaya, O., Qiu, Y., Harper, S., Bates, D. O. and Churchill, A. J. (2005) 'Diabetic retinopathy is associated with a switch in splicing from anti- to pro-angiogenic isoforms of vascular endothelial growth factor', *Diabetologia*, 48(11), 2422-2427.

Varey, A. H. R., Rennel, E. S., Qiu, Y., Bevan, H. S., Perrin, R. M., Raffy, S., Dixon, A. R., Paraskeva, C., Zaccheo, O., Hassan, A. B., Harper, S. J. and Bates, D. O. (2008) 'VEGF(165)b, an antiangiogenic VEGF-A isoform, binds and inhibits bevacizumab treatment in experimental colorectal carcinoma: balance of pro- and antiangiogenic VEGF-A isoforms has implications for therapy', *British Journal of Cancer*, 98(8), 1366-1379.

Pritchard-Jones, R. O., Dunn, D. B. A., Qiu, Y., Varey, A. H. R., Orlando, A., Rigby, H., Harper, S. J. and Bates, D. O. (2007) 'Expression of VEGF(xxx)b, the inhibitory isoforms of VEGF, in malignant melanoma', *British Journal of Cancer*, 97(2), 223-230.

Hua, J., Spee, C., Kase, S., Rennel, E. S., Magnussen, A. L., Qiu, Y., Varey, A., Dhayade, S., Churchill, A. J., Harper, S. J., Bates, D. O. and Hinton, D. R. (2010) 'Recombinant Human VEGF(165)b Inhibits Experimental Choroidal Neovascularization', *Investigative Ophthalmology & Visual Science*, 51(8), 4282-4288.

Magnussen, A. L., Rennel, E. S., Hua, J., Bevan, H. S., Long, N. B., Lehrling, C., Gammons, M., Floege, J., Harper, S. J., Agostini, H. T., Bates, D. O. and Churchill, A. J. (2010) 'VEGF-A(165)b Is Cytoprotective and Antiangiogenic in the Retina', *Investigative Ophthalmology & Visual Science*, 51(8), 4273-4281.

Rosenfeld, P. J., Rich, R. M. and Lalwani, G. A. (2006) 'Ranibizumab: Phase III clinical trial results', *Ophthalmology clinics of North America*, 19(3), 361-72.

Brown, D. M., Kaiser, P. K., Michels, M., Soubrane, G., Heier, J. S., Kim, R. Y., Sy, J. P., Schneider, S. and Grp, A. S. (2006) 'Ranibizumab versus verteporfin for neovascular age-related macular degeneration', *New England Journal of Medicine*, 355(14), 1432-1444.

Brown, D. M., Michels, M., Kaiser, P. K., Heier, J. S., Sy, J. P. and Ianchulev, T. (2009) 'Ranibizumab versus Verteporfin Photodynamic Therapy for Neovascular Age-Related Macular Degeneration: Two-Year Results of the ANCHOR Study', *Ophthalmology*, 116(1), 57-65.

Schmidt-Erfurth, U., Eldem, B., Guymer, R., Korobelnik, J.-F., Schlingemann, R. O., Axer-Siegel, R., Wiedemann, P., Simader, C., Gekkieva, M., Weichselberger, A. and Grp, E. S. (2011) 'Efficacy and Safety of Monthly versus Quarterly Ranibizumab Treatment in Neovascular Age-related Macular Degeneration: The EXCITE Study', *Ophthalmology*, 118(5).

Good, T. J. and Kahook, M. Y. (2010) 'The role of endothelin in the pathophysiology of glaucoma', *Expert Opinion on Therapeutic Targets*, 14(6), 647-654.

Jager, R. D., Aiello, L. P., Patel, S. C. and Cunningham, E. T. (2004) 'Risks of intravitreous injection: A comprehensive review', *Retina-the Journal of Retinal and Vitreous Diseases*, 24(5), 676-698.

Nowak, D. G., Amin, E. M., Rennel, E. S., Hoareau-Aveilla, C., Gammons, M., Damodoran, G., Hagiwara, M., Harper, S. J., Woolard, J., Ladomery, M. R. and Bates, D. O. (2010) 'Regulation of Vascular Endothelial Growth Factor (VEGF) Splicing from Pro-angiogenic to Anti-angiogenic Isoforms a novel therapeutic strategy for angiogenesis', *Journal of Biological Chemistry*, 285(8), 5532-5540.

Amin, E. M., Oltean, S., Hua, J., Gammons, M. V. R., Hamdollah-Zadeh, M., Welsh, G. I., Cheung, M.-K., Ni, L., Kase, S., Renne, E. S., Symonds, K. E., Nowak, D. G., Royer-Pokora, B., Saleem, M. A., Hagiwara, M., Schumacher, V. A., Harper, S. J., Hinton, D. R., Bates, D. O. and Ladomery, M. R. (2011) 'WT1 Mutants Reveal SRPK1 to Be a Downstream Angiogenesis Target by Altering VEGF Splicing', *Cancer Cell*, 20(6), 768-780.

Sanford, J. R., Ellis, J. D., Cazalla, D. and Caceres, J. F. (2005a) 'Reversible phosphorylation differentially affects nuclear and cytoplasmic functons of splicing factor 2/alternative splicing factor', *Proceedings of the National Academy of Sciences of the United States of America*, 102(42), 15042-15047.

Nowak, D. G., Woolard, J., Amin, E. M., Konopatskaya, O., Saleem, M. A., Churchill, A. J., Ladomery, M. R., Harper, S. J. and Bates, D. O. (2008) 'Expression of pro- and anti-angiogenic isoforms of VEGF is differentially regulated by splicing and growth factors', *Journal of Cell Science*, 121(20), 3487-3495.

Doukas, J., Mahesh, S., Umeda, N., Kachi, S., Akiyama, H., Yokoi, K., Cao, J., Chen, Z., Dellamary, L., Tam, B., Racanelli-Layton, A., Hood, J., Martin, M., Noronha, G., Soll, R. and Campochiaro, P. A. (2008) 'Topical administration of a multi-targeted kinase inhibitor suppresses choroidal neovascularization and retinal edema', *Journal of Cellular Physiology*, 216(1), 29-37.

Fukuhara, T., Hosoya, T., Shimizu, S., Sumi, K., Oshiro, T., Yoshinaka, Y., Suzuki, M., Yamamoto, N., Herzenberg, L. A. and Hagiwara, M. (2006) 'Utilization of host SR protein kinases and RNA-splicing machinery during viral replication', *Proceedings of the National Academy of Sciences of the United States of America*, 103(30), 11329-11333.

Rennel, E. S., Regula, J. T., Harper, S. J., Thomas, M., Klein, C. and Bates, D. O. (2011) 'A Human Neutralizing Antibody Specific to Ang-2 Inhibits Ocular Angiogenesis', *Microcirculation*, 18(7).

Aubol, B. E., Chakrabarti, S., Ngo, J., Shaffer, J., Nolen, B., Fu, X. D., Ghosh, G. and Adams, J. A. (2003) 'Processive phosphorylation of alternative splicing factor/splicing factor 2', *Proceedings of the National Academy of Sciences of the United States of America*, 100(22), 12601-12606.

Velazquez-Dones, A., Hagopian, J. C., Ma, C. T., Zhong, X. Y., Zhou, H. L., Ghosh, G., Fu, X. D. and Adams, J. A. (2005) 'Mass spectrometric and kinetic analysis of ASF/SF2 phosphorylation by SRPK1 and Clk/Sty', *Journal of Biological Chemistry*, 280(50), 41761-41768.

Ngo, J. C. K., Chakrabarti, S., Ding, J. H., Velazquez-Dones, A., Nolen, B., Aubol, B. E., Adams, J. A., Fu, X. D. and Ghosh, G. (2005) 'Interplay between SRPK and Clk/Sty kinases in phosphorylation of the splicing factor ASF/SF2 is regulated by a docking motif in ASF/SF2', *Molecular Cell*, 20(1), 77-89.

Xu, J., Dou, T., Liu, C., Fu, M., Huang, Y., Gu, S., Zhou, Y. and Xie, Y. (2011) 'The evolution of alternative splicing exons in vascular endothelial growth factor A', *Gene*, 487 (2).

Caines, K. C., de Avila, J. M., Cupp, A. S. and McLean, D. J. (2012) 'VEGFA Family Isoforms Regulate Spermatogonial Stem Cell Homeostasis in Vivo', *Endocrinology*, 153(2).

Zhao, M., Shi, X., Liang, J., Miao, Y., Xie, W., Zhang, Y. and Li, X. (2011) 'Expression of pro- and anti-angiogenic isoforms of VEGF in the mouse model of oxygen-induced retinopathy', *Experimental Eye Research,* 93(6), 921-926.

Harris, S., Craze, M., Newton, J., Fisher, M., Shima, D. T., Tozer, G. M. and Kanthou, C. (2012) 'Do Anti-Angiogenic VEGF (VEGF$_{xxx}$b) Isoforms Exist? A Cautionary Tale', *Plos One,* 7(5).

McFee, R. M., Rozell, T. G. and Cupp, A. S. (2012) 'The balance of proangiogenic and antiangiogenic VEGFA isoforms regulate follicle development', *Cell and Tissue Research,* 349(3).

Ishida, S., Usui, T., Yamashiro, K., Kaji, Y., Amano, S., Ogura, Y., Hida, T., Oguchi, Y., Ambati, J., Miller, J. W., Gragoudas, E. S., Ng, Y. S., D'Amore, P. A., Shima, D. T. and Adamis, A. P. (2003) 'VEGF$_{164}$-mediated inflammation is required for pathological, but not physiological, ischemia-induced retinal neovascularization', *Journal of Experimental Medicine,* 198(3), 483-489.

Geroski, D. H. and Edelhauser, H. F. (2000) 'Drug delivery for posterior segment eye disease', *Investigative Ophthalmology & Visual Science,* 41(5), 961-964.

Keyt, B. A., Nguyen, H. V., Berleau, L. T., Duarte, C. M., Park, J., Chen, H. and Ferrara, N. (1996) 'Identification of vascular endothelial growth factor determinants for binding KDR and FLT-1 receptors—Generation of receptor-selective VEGF variants by site-directed mutagenesis', *Journal of Biological Chemistry,* 271(10), 5638-5646.

Stalmans, I., Ng, Y. S., Rohan, R., Fruttiger, M., Bouche, A., Yuce, A., Fujisawa, H., Hermans, B., Shani, M., Jansen, S., Hicklin, D., Anderson, D. J., Gardiner, T., Hammes, H. P., Moons, L., Dewerchin, M., Collen, D., Carmeliet, P. and D'Amore, P. A. (2002) 'Arteriolar and venular patterning in retinas of mice selectively expressing VEGF isoforms', *Journal of Clinical Investigation,* 109(3).

Gammons, M. V., Dick, A. D., Harper, S. J., Bates, D. O. (2013) SRPK1 Inhibition Modulates VEGF Splicing to Reduce Pathological Neovascularization in a Rat Model of Retinopathy of Prematurity *Invest. Ophthalmol. Vis. Sci.* vol. 54(8) 5797-5806.

Gammons, M. V., Fedorov, O., Ivison, D., Du, C., Clark, T., Hopkins, C., Hagiwara, M., Dick, A. D., Cox, R., Harper, S. J., Hancox, J. C. and Bates, D. O. (2013) Topical Antiangiogenic SRPK1 Inhibitors Reduce Choroidal Neovascularization in Rodent Models of Exudative AMD *Invest. Ophthalmol. Vis. Sci.* 54(9) 6052-6062.

Federov O, Niesen F H, Knapp S. Kinase Inhibitor Selectivity Profiling Using Differential Scanning Fluorimetry. In: Kuster B, ed. Kinase Inhibitors: Methods and Protocols: Springer, 2011: 109-18.

Carter J G, Gammons M V, Damodaran G, Churchill A J, Harper S J, Bates D O. (2015) The carboxyl terminus of VEGF-A is a potential target for anti-angiogenic therapy. *Angiogenesis* 18(1), 23-30.

Chomczynski, P., and Sacchi, N. Single-step method of RNA isolation by acid quanidinium thiocyanate phenol chloroform extraction. *Anal. Biochem.,* 162: 156-159, 1987.

The invention claimed is:

1. A compound of Formula (I):

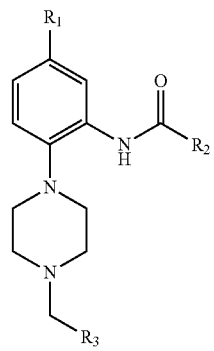

(I)

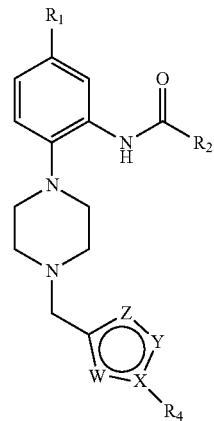

(Ia)

or a pharmaceutically acceptable salt, solvate, hydrate or prodrug, wherein:

$R_1$ is $CF_3$, methyl, $CHF_2$, Cl, or cyclopropyl; and either
$R_2$ is methyl, a 5- or 6-membered aromatic heterocycle, phenyl, or a condensed aromatic heterocycle, each of which may optionally have one or more substituent; and
$R_3$ is a 5-membered aromatic heterocycle which may optionally have one or more substituent; or
$R_2$ is methyl, a 6-membered aromatic heterocycle, phenyl, or a condensed aromatic heterocycle, each of which may optionally have one or more substituent; and
$R_3$ is a condensed aromatic heterocycle, which may optionally have one or more substituent.

2. A compound according to claim 1, wherein the compound is of Formula (Ia):

or a pharmaceutically acceptable salt, solvate, hydrate or prodrug thereof; wherein:

$R_1$ is $CF_3$, methyl, $CHF_2$, Cl, or cyclopropyl;

$R_2$ is methyl, a 5- or 6-membered aromatic heterocycle or a condensed aromatic heterocycle, each of which may optionally have one or more substituent;

$R_4$ is hydrogen, or a $C_{1-6}$ alkyl group which may optionally have one or more substituent;

W is CH, O, N or S;

X is C or N;

Y is CH, O, N or S; and

Z is CH, N or S.

3. A compound according to claim 2, wherein $R_2$ is selected from the group consisting of:

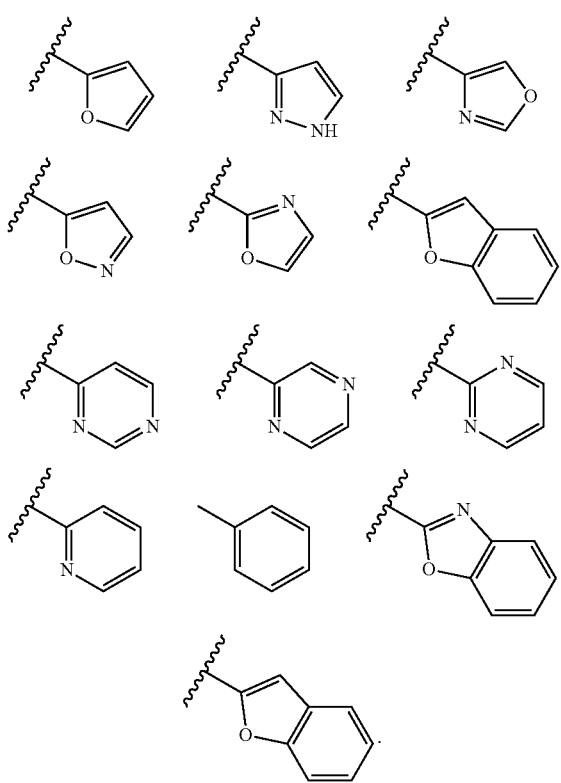

4. A compound according to claim 2, wherein Z=CH or N.

5. A compound according to claim 2, wherein W, X, Y and Z are selected such that the 5-membered aromatic heterocycle is selected from the group consisting of:

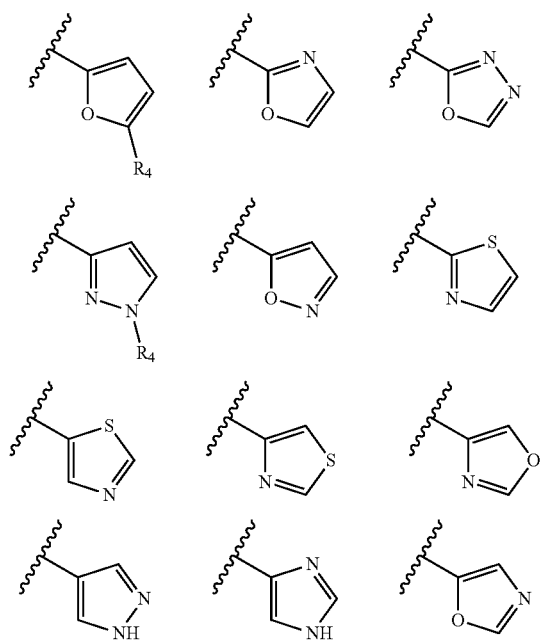

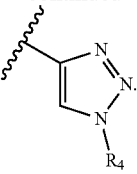

6. A compound according to claim 2, wherein $R_4$ is hydrogen.

7. A compound according to claim 2 wherein $R_4$ is a methyl group, which may have a substituent.

8. A compound according to claim 7, wherein $R_4$ is a methyl group substituted with phenyl or a 5- or 6-membered aromatic heterocycle.

9. A compound according to claim 1, wherein:
$R_1$ is $CF_3$, methyl, $CHF_2$, Cl, or cyclopropyl;
$R_2$ is methyl, a 6-membered aromatic heterocycle, phenyl, or a condensed aromatic heterocycle, each of which may optionally have one or more substituent; and
$R_3$ is a condensed aromatic heterocycle, which may optionally have one or more substituent.

10. A compound according to claim 9, wherein $R_3$ is an indolyl group, an isoindolyl group, a benzoxazolyl group, a benzimidazolyl group, a coumarinyl group, a quinolyl group or an isoquinolyl group.

11. A compound according to claim 1, wherein $R_1$ is $CF_3$ or Cl.

12. A compound according to claim 1, wherein $R_2$ is an indolyl group, an isoindolyl group, a benzoxazolyl group, a benzimidazolyl group, a coumarinyl group, a quinolyl group or an isoquinolyl group.

13. A pharmaceutical composition comprising a compound of claim 1, optionally one or more other active ingredients and a pharmaceutically acceptable carrier.

14. A pharmaceutical composition comprising a compound of claim 1, optionally one or more other active ingredients and a pharmaceutically acceptable carrier, in a form suitable for intraocular injection.

15. A pharmaceutical composition comprising a compound of claim 1, optionally one or more other active ingredients and a pharmaceutically acceptable carrier, in a form suitable for topical administration to the eye.

16. A compound according to claim 1, wherein $R_2$ is a furan-2-yl group or a pyridin-2-yl group, each of which may optionally have one or more substituent.

17. A method of treating ocular neovascularisation comprising administering a therapeutically effective amount of a compound according to claim 1 to a subject in need of treatment.

18. The method of claim 17, wherein said treatment of ocular neovascularisation comprises treatment of age-related macular degeneration.

19. A method of inhibiting SRPK1 to thereby treat a disease or condition in a subject in need thereof, said method comprising administering a therapeutically effective amount of a SRPK1-specific inhibitor compound according to claim 1 to said subject.

20. The method of claim 19, wherein said disease or condition is selected from the group consisting of abnormal angiogenesis, over-production of pro-angiogenic VEGF isoforms in a mammalian subject, microvascular hyperpermeability, fibrosis, cancer, neurodegeneration, neuropathy, and pain.

21. A compound according to claim 1, wherein $R_2$ is a furan-2-yl group having a methyl substituent, a tetrahydropyranyl substituent, or a pyridinyl substituent.

* * * * *